US010501518B2

(12) United States Patent
Gellman et al.

(10) Patent No.: US 10,501,518 B2
(45) Date of Patent: Dec. 10, 2019

(54) ALPHA-/BETA-POLYPEPTIDE ANALOGS OF PARATHYROID HORMONE (PTH) AND METHOD OF USING SAME

(71) Applicants: WISCONSIN ALUMNI RESEARCH FOUNDATION, Madison, WI (US); The General Hospital Corporation, Boston, MA (US)

(72) Inventors: Samuel H. Gellman, Madison, WI (US); Ross W. Cheloha, Madison, WI (US); Thomas J. Gardella, Needham, MA (US)

(73) Assignees: Wisconsin Alumni Research Foundation, Madison, WI (US); General Hospital Corporation, Boston, MA (US)

( * ) Notice: Subject to any disclaimer, the term of this patent is extended or adjusted under 35 U.S.C. 154(b) by 77 days.

(21) Appl. No.: 14/312,012

(22) Filed: Jun. 23, 2014

(65) Prior Publication Data
US 2014/0378382 A1 Dec. 25, 2014

Related U.S. Application Data

(60) Provisional application No. 61/940,124, filed on Feb. 14, 2014, provisional application No. 61/838,307, filed on Jun. 23, 2013.

(51) Int. Cl.
*A61K 38/29* (2006.01)
*A61P 5/18* (2006.01)
*C07K 14/635* (2006.01)
*A61K 38/00* (2006.01)
*C07K 5/00* (2006.01)
*C07K 7/00* (2006.01)
*C07K 16/00* (2006.01)
*C07K 17/00* (2006.01)

(52) U.S. Cl.
CPC ............ *C07K 14/635* (2013.01); *A61K 38/00* (2013.01)

(58) Field of Classification Search
CPC ................................ C07K 14/635; A61K 38/29
See application file for complete search history.

(56) References Cited

U.S. PATENT DOCUMENTS

| 2002/0025929 | A1 | 2/2002 | Sato | |
| 2005/0026839 | A1 | 2/2005 | Gardella | |
| 2006/0058230 | A1* | 3/2006 | Chorev et al. | 514/12 |
| 2010/0099185 | A1* | 4/2010 | Horne et al. | 435/366 |
| 2013/0096050 | A1 | 4/2013 | Shandler | |

OTHER PUBLICATIONS

Peggion et al. "Structure-Function Studies of Analogues of Parathyroid Hormone (PTH)-1-34 Containing Beta-Amino Acid Residues in Positions 11-13" Biochemistry 41:8162-8175. Published Jun. 1, 2002.*
Schievano et al. "Conformational and Biological Characterization of Human Parathyroid Hormone hPTH(1-34) Analogues Containing Beta-Amino Acid Residues in Positions 17-19" Biopolymers 70:534-547. (Year: 2003).*
Berlot, C.H. A highly effective dominant negative $\alpha_s$ construct containing mutations that affect distinct functions inhibits multiple $G_s$-coupled receptor signaling pathways. *J. Biol. Chem.* 277, 21080-21085 (2002).
Binkowski, B.F. et al. A Luminescent Biosensor with Increased Dynamic Range for Intracellular cAMP. *ACS Chem. Biol.* 6, 1193-1197 (2011).
Boersma, M.D. et al. Evaluation of Diverse alpha/beta-Backbone Patterns for Functional α-Helix Mimicry: Analogs of the Bim BH3 Domain. *J. Am. Chem. Soc.* 134, 315-323 (2012).
Dean, T. et al. Mechanisms of ligand binding to the parathyroid hormone (PTH)/PTH-related protein receptor: Selectivity of a modified PTH(1-15) Radioligand for $G\alpha_s$-coupled receptor conformations. *Mol Endocrinol.* 20, 931-943 (2006).
Dean et al., Altered selectivity of parathyroid hormone (PTH) and PTH-Related protein (PTHrP) for distinct conformations of the PTH/PTHrP receptor. *Mol. Endocrinol.* 22, 156-166 (2008).
Feinstein et al. Retromer terminates the generation of cAMP by internalized PTH receptors. *Nat. Chem. Biol.* 7, 278-284 (2011).
Gardella et al., Analysis of Parathyroid Hormone's Principal Receptor-binding Region by Site-directed Mutagenesis and Analog, *Endocrinology* 132, 2024-2030 (1993).
Gill et al., Calculation of protein extinction coefficients from amino-acid sequence data. *Analytical Biochemistry* 182, 319-326 (1989).
Hoare et al., Measurement of agonist and antagonist ligand-binding parameters at the human parathyroid hormone type 1 receptor: Evaluation of receptor states and modulation by guanine nucleotide. *J. Pharmacol. Exp. Ther.* 289, 1323-1333 (1999).
Hoare et al., Evaluating the signal transduction mechanism of the parathyroid hormone 1 receptor—Effect of receptor-G-protein interaction on the ligand binding mechanism and receptor conformation. *J. Biol. Chem.* 276, 7741-7753 (2001).
Horne et al., Sequence-based design of α/β-peptide foldamers that mimic BH3 domains. *Angew. Chem. Int. Ed.* 47, 2853-2856 (2008).
Horne et al. Structural and biological mimicry of protein surface recognition by α/β-peptide foldamers. *Proc. Natl. Acad. Sci. U.S.A.* 106, 14751-14756 (2009).
Kenakin et al., A. Signaling bias in new drug discovery: detection, quantification and therapeutic impact. *Nat. Rev. Drug Discovery* 12, 205 (2013).

(Continued)

Primary Examiner — Christina Bradley
Assistant Examiner — Zachary J Miknis
(74) Attorney, Agent, or Firm — Joseph T. Leone, Esq.; DeWitt LLP

(57) ABSTRACT

Described are polypeptide analogs of parathyroid hormone (PTH) that include at least two non-adjacent β-amino acid residues in place of a naturally occurring α-amino acid residues. Also described are pharmaceutical compositions useful for treating hypoparathyroidism that contain the analogs and methods of using the analogs to treat hypoparathyroidism.

12 Claims, 16 Drawing Sheets

Specification includes a Sequence Listing.

(56) References Cited

OTHER PUBLICATIONS

King et al., A cleavage method which minimizes side reactions following FMOC solid-phase peptide-synthesis, *International Journal of Peptide and Protein Research* 36, 255-266 (1990).

Kostenuik et al. Infrequent delivery of a long-acting PTH-Fc fusion protein has potent anabolic effects on cortical and cancellous bone. *Journal of Bone and Mineral Research* 22, 1534-1547 (2007).

Koth et al. Molecular basis for negative regulation of the glucagon receptor. *Proc. Natl. Acad. Sci. U.S.A.* 109, 14393-14398 (2012).

Lagerstrom et al., Structural diversity of G protein-coupled receptors and significance for drug discovery. *Nat. Rev. Drug Discovery* 7, 339-357 (2008).

Maeda et al. Critical role of parathyroid hormone (PTH) receptor-1 phosphorylation in regulating acute responses to PTH. *Proc. Natl. Acad. Sci. U.S.A.* 110, 5864-5869 (2013).

Neer et al. Effect of parathyroid hormone (1-34) on fractures and bone mineral density in postmenopausal women with osteoporosis. *N. Engl. J. Med.* 344, 1434-1441 (2001).

Okazaki et al. Prolonged signaling at the parathyroid hormone receptor by peptide ligands targeted to a specific receptor conformation. *Proc. Natl. Acad. Sci. U.S.A.* 105, 16525-16530 (2008).

Pal et al., Structure and mechanism for recognition of peptide hormones by Class B G-protein-coupled receptors. *Acta Pharmacol. Sin.* 33, 300-311 (2012).

Parthier et al., Passing the baton in class B GPCRs: peptide hormone activation via helix induction? *Trends Biochem. Sci.* 34, 303-310 (2009).

Pioszak et al., Molecular recognition of parathyroid hormone by its G protein-coupled receptor. *Proc. Natl. Acad. Sci. U.S.A.* 105, 5034-5039 (2008).

Piserchio et al., Residue 19 of the parathyroid hormone: Structural consequences. *Biochemistry* 41, 13217-13223 (2002).

Qin et al., Parathyroid hormone: a double-edged sword for bone metabolism. *Trends in Endocrinology and Metabolism* 15, 60-65 (2004).

Rajagopal et al., Teaching old receptors new tricks: biasing seven-transmembrane receptors. *Nat. Rev. Drug Discovery* 9, 373-386 (2010).

Rajagopal et al. Quantifying Ligand Bias at Seven-Transmembrane Receptors. *Mol. Pharmacol.* 80, 367-377 (2011).

Rasmussen et al. Crystal structure of the $\beta_2$ adrenergic receptor-Gs protein complex. *Nature* 477, 549-U311 (2011).

Schievano et al. Conformational and biological characterization of human parathyroid hormone hPTH(1-34) analogs containing beta-amino acid residues in positions 17-19. *Biopolymers* 70, 534-547 (2003).

Shimizu et al., Minimization of parathyroid hormone—Novel amino-terminal parathyroid hormone fragments with enhanced potency in activating the type-1 parathyroid hormone receptor. *J. Biol. Chem.* 275, 21836-21843 (2000).

Serada et al. The role of the liver and kidneys in the pharmacokinetics of subcutaneously administered teriparatide acetate in rats. *Xenobiotica* 42, 398-407 (2012).

Uzawa et al., Comparison of the Effects of Intermittent and Continuous Administration of Human Parathyroid Hormone(1-34) on Rat Bone. *Bone* 16, 477-484 (1995).

Venkatakrishnan et al. Molecular signatures of G-protein-coupled receptors. *Nature* 494, 185-194 (2013).

Vilardaga et al., Molecular basis of parathyroid hormone receptor signaling and trafficking: a family B GPCR paradigm. *Cell. Mol. Life Sci.* 68, 1-13 (2011).

\* cited by examiner

FIG. 2

```
A3: SVSEIQLMHNLGKHLNSMERVEWLRKKLQDVHNF-NH₂   (SEQ. ID. NO: 1)
B3: SVSEIQLMHNLGKHLNSMERVEWLRKKLQDVQNF-NH₂   (SEQ. ID. NO: 2)
C3: SVSEIQLMHNLGKHLNSMERVEWLRKKLQDVHNF-NH₂   (SEQ. ID. NO: 3)
D3: SVSEIQLMHNLGKHLNSMERVEWLRKKLQDVHNF-NH₂   (SEQ. ID. NO: 4)
A5: SVSEIQLMHNLGKHLRSMERVEWLRKKLQDVHNF-NH₂   (SEQ. ID. NO: 5)
B5: SVSEIQLMHNLGKHLNSMERVEWLRKKLQDVHNF-NH₂   (SEQ. ID. NO: 6)
C5: SVSEIQLMHNLGKHLNSMERVEWLRKKLQDVQNF-NH₂   (SEQ. ID. NO: 7)
D5: SVSEIQLMHNLGKHLNSMERVEWLRKKLQDVHNF-NH₂   (SEQ. ID. NO: 8)
D6: SVSEIQLMHNLGKHLNSMERVEWLRKKLQDVHNF-NH₂   (SEQ. ID. NO: 9)
D7: SVSEIQLMHNLGKWLNSMERVEWLRKKLQDVHNF-NH₂   (SEQ. ID. NO: 10)
``` bold, underlined residues indicate β³ residues having the side chain of the α residue indicated by the letter. All other residues are conventional, single-letter codes designating proteinogenic α residues.

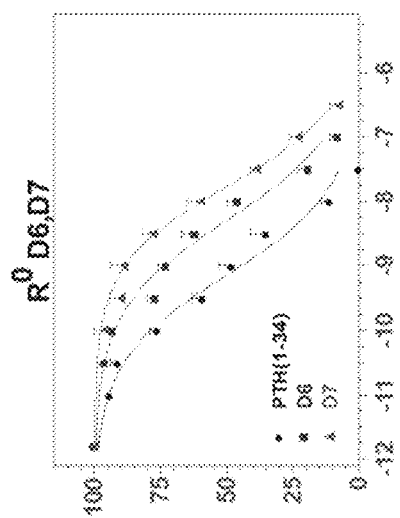
FIG. 7A
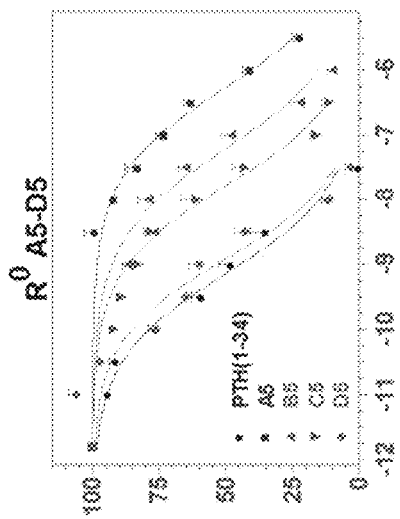</br>FIG. 7B
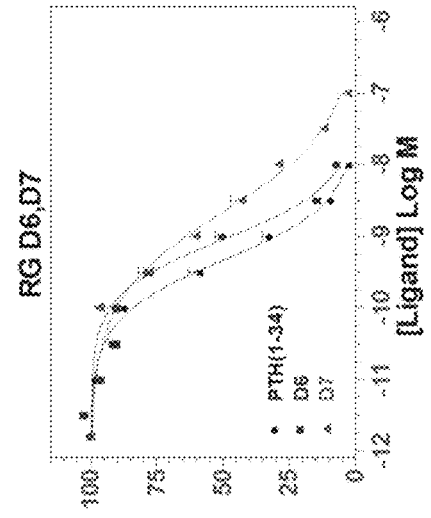
FIG. 7C
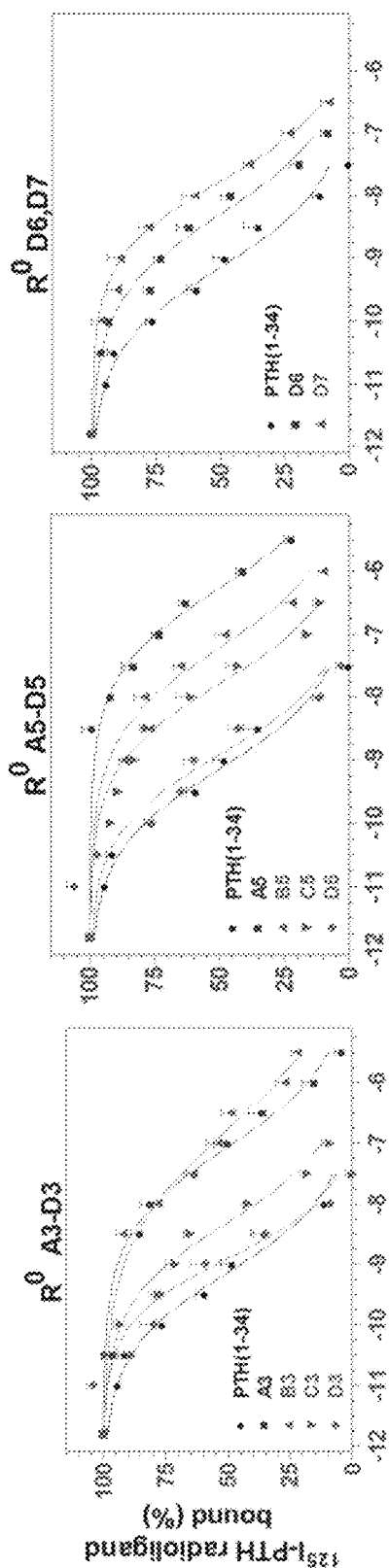
FIG. 7D
FIG. 7E
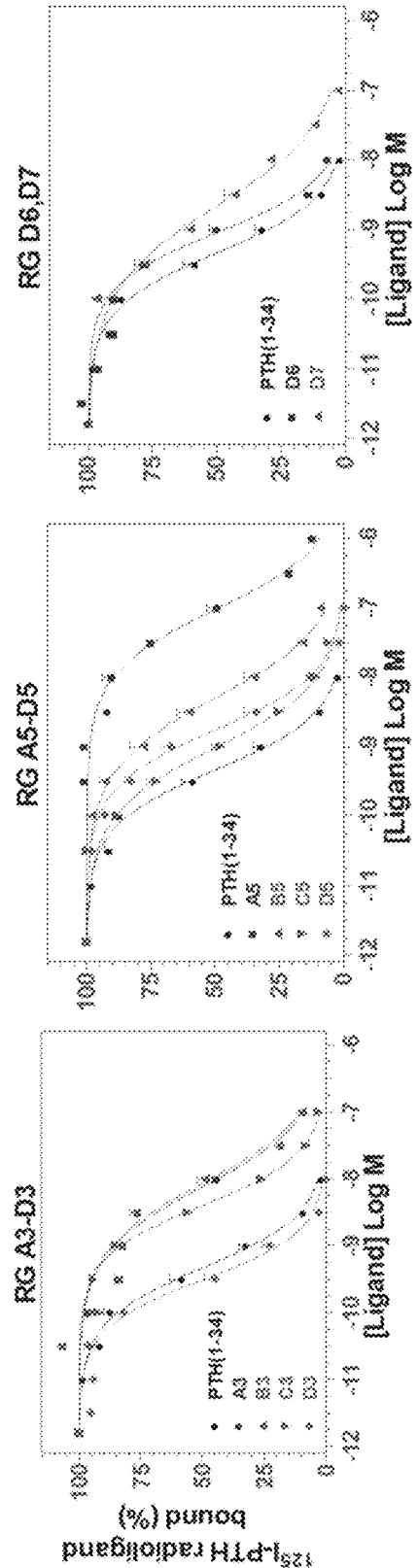
FIG. 7F

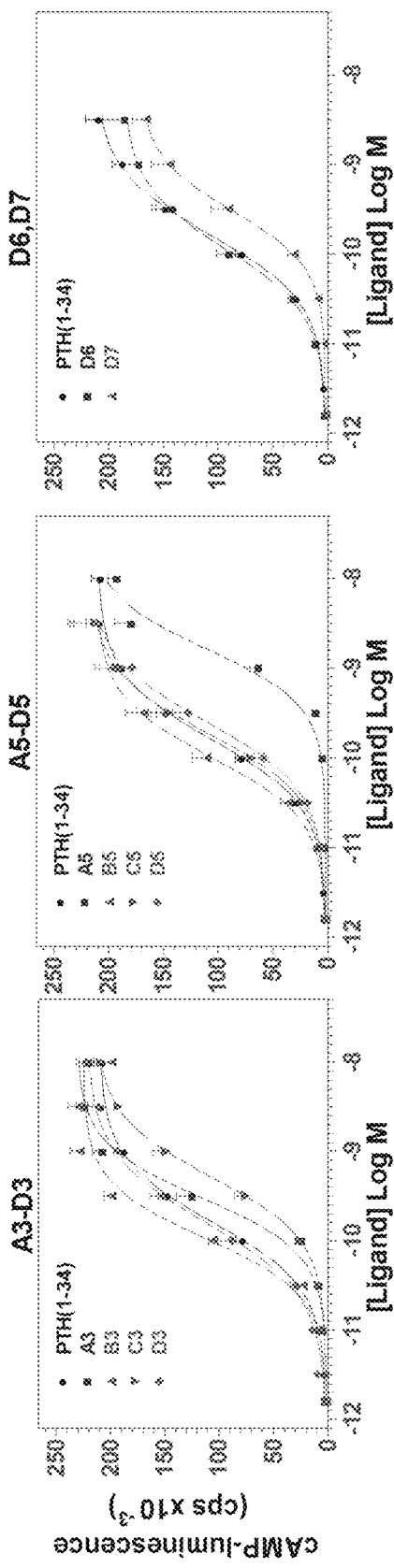
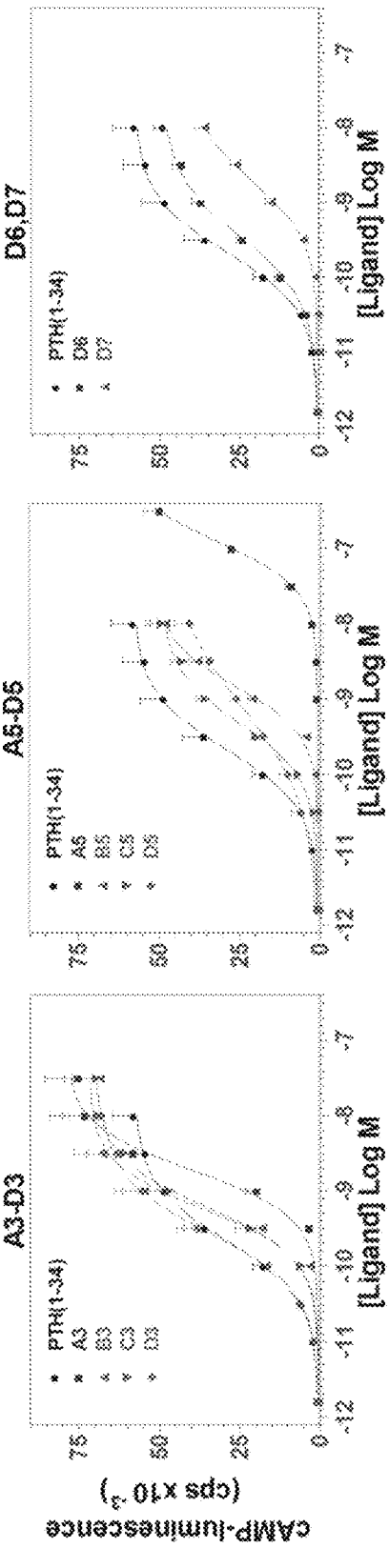
FIG. 8A FIG. 8B FIG. 8C
FIG. 9A FIG. 9B FIG. 9C

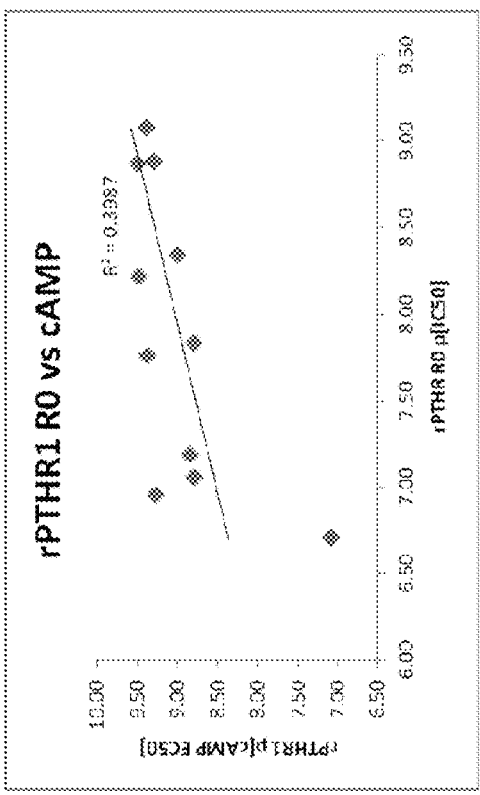
FIG. 10A
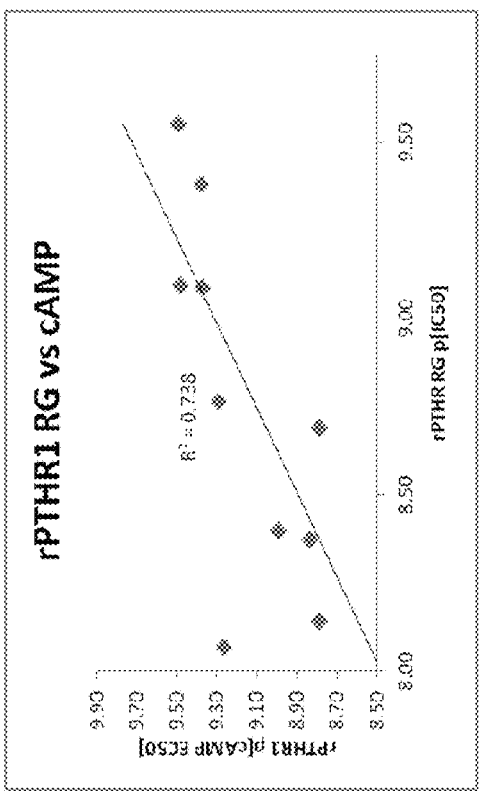
FIG. 10B
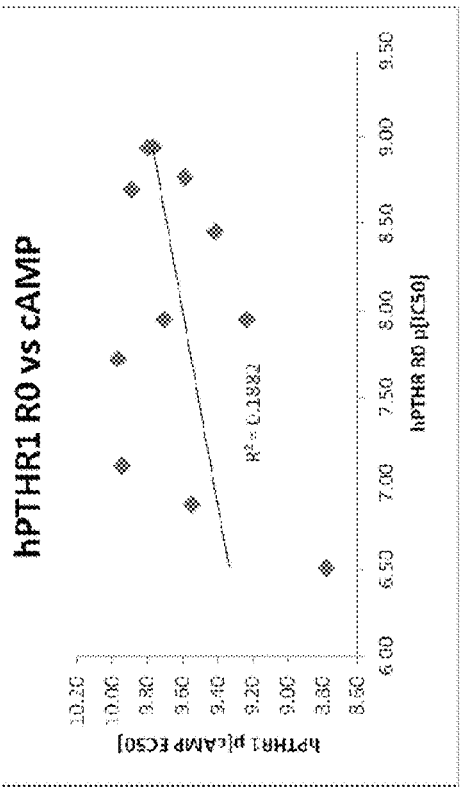
FIG. 10C
FIG. 10D

ALPHA-/BETA-POLYPEPTIDE ANALOGS OF PARATHYROID HORMONE (PTH) AND METHOD OF USING SAME

CROSS-REFERENCE TO RELATED APPLICATIONS

Priority is hereby claimed to provisional application Ser. No. 61/940,124, filed Feb. 14, 2014, and to provisional application Ser. No. 61/838,307, filed Jun. 23, 2013, both of which are incorporated herein by reference.

FEDERAL FUNDING STATEMENT

This invention was made with government support under GM056414 and DK011794 awarded by the National Institutes of Health. The government has certain rights in the invention.

BACKGROUND

Proper function of individual cells and entire organisms depends upon information transfer from the extracellular environment to the cytoplasm. Most signals must be transduced via proteins that span cellular membranes. Many receptor proteins do not act as simple, binary "toggle switches," with only signaling-active and signaling-inactive states. Rather, they behave in vivo as nuanced interpreters of molecular information. This behavior enables the transmission of diverse messages based on variations in agonist structure. "Biased agonism" is one widely-studied manifestation of this complexity that has been documented for multiple G protein-coupled receptors (GPCRs).[1,2] Signal transduction via these GPCRs involves multiple intracellular partners, only some of which are G proteins. A natural agonist activates these alternative signaling pathways in a given proportion, for a given cell type and environment. Other agonists are designated as biased relative to this benchmark if they lead to a different balance of signal intensities among the available pathways.[3] These differences in signal transduction pattern can arise from subtle agonist-dependent variations in receptor conformation.[4]

The biased agonism paradigm is not the only mechanism by which diversity in GPCR signaling can arise from variations in agonist-bound receptor conformation. The parathyroid hormone receptor-1 (PTHR-1), for example, has two distinct functional states. These are depicted schematically in FIG. 1. The RG functional state, shown to the right in FIG. 1, forms when the intracellular portion contacts a given G protein (designated $G\alpha_{ND}$ in FIG. 1). In contrast, the $R^0$ functional state, shown to the left in FIG. 1, forms independent of G protein association.[5,6] An agonist's affinity for the RG state is predicted to correlate with PTHR-1 activation potency, while an agonist's $R^0$ affinity correlates with the duration of some in vivo responses.[7,8] Natural agonists for PTHR-1 include parathyroid hormone (PTH) and parathyroid hormone-related protein (PTHrP), which display similar affinity for the RG state but differ in their affinity for the $R^0$ state.[7] This behavior cannot be described as biased agonism because PTH and PTHrP seem to activate the same intracellular signaling mechanisms,[9] but there is a clear mechanistic parallel to the bias paradigm in that agonists with different receptor-state selectivities cause different biological effects.[7,8,10]

Receptor state-selective agonists are highly prized because these molecules can serve as powerful tools for elucidating signal-transduction mechanisms, and they may give rise to therapeutic agents with minimal deleterious side effects.[1,2] At present, there is no way to design such agonists via rational methods.

In terms of mammalian disease states, including humans, the umbrella term hypoparathyroidism is used to designate any decreased function of the parathyroid glands with concomitant underproduction of PTH. This then leads to low levels of calcium in the blood. The main symptoms of hypoparathyroidism are the result of the low blood calcium level, which interferes with normal muscle contraction and nerve conduction. As a result, people with hypoparathyroidism experience a number of unsettling symptoms, including paresthesia (an unpleasant tingling sensation around the mouth and in the hands and feet), muscle cramps, and tetany (severe spasms that affect the hands and feet). Many subjects suffering from hypoparathyroidism also report somewhat vague but pervasive symptoms such as fatigue, headaches, bone pain and insomnia. Chronic hypoparathyroidism is conventionally treated with vitamin D analogs and calcium supplementation. However, such treatments are contra-indicated in many patients due to potential renal damage. The N-terminal fragment of parathyroid hormone, PTH (1-34), has full biological activity. Teriparatide (marketed in the U.S. by Eli Lilly & Co. under the trademark "Forteo") is a recombinant form of PTH approved for use in the treatment of osteoporosis.

SUMMARY OF THE INVENTION

G protein-coupled receptors (GPCRs), the targets of many current therapeutic agents, can adopt multiple activated states, and there is increasing interest in synthetic molecules that display altered receptor-state selectivity patterns relative to natural agonists. Disclosed herein are backbone-modified analogs of a well-known peptide agonist, PTH(1-34). The analogs were generated via systematic replacement of selected α-amino acid residues with homologous β-amino acid residues. Two distinct states of PTHR-1 with high agonist affinity are known, and this system was used to assess the impact of backbone modification on binding preferences for the alternative receptor conformations. The results show that diverse binding profiles can be achieved via this strategy. The resulting variations in agonist properties can give rise to distinct behaviors in vivo.

Thus, disclosed herein is a method to make unnatural PTHR-1 peptide agonists. The method comprises determining or acquiring the α-amino acid sequence of a first PTHR-1 peptide agonist that comprises α-amino acid residues, and then fabricating an analog of the first PTHR-1 peptide agonist in which at least two non-adjacent α-amino acid residues are replaced with β-amino acid residues. The at least two non-adjacent α-amino acid residue may optionally be replaced with β-amino acid residues having the same side-chain as the α-amino acid residue it replaces. Alternatively, at least one of the at least two non-adjacent α-amino acid residue may optionally be replaced with a cyclically constrained β-amino acid residue. The replacement β-amino acid residues are non-adjacent as well (because the α-amino acids they replace are non-adjacent). The β-amino acid residues may appear in any pattern, so long as they are non-adjacent to one another. For example, the β-amino acid residues may optionally appear in a pattern comprising αβαβ, ααβααβ, αααβαααβ, and ααβαααβ.

Also disclosed herein are the resulting unnatural, isolated peptide analogs. Thus, disclosed herein are unnatural, isolated peptide analogs comprising PTH, a parathyroid hormone receptor (PTHR-1, PTHR-2) agonist- or antagonist- or inverse agonist effective fragment of PTH, a parathyroid hormone related protein (PTHrP), a PTHR-1 or PTHR-2 agonist-, antagonist-, or inverse agonist-effective fragment of PTHrP, M-PTH, a PTHR-1 or PTHR-2 agonist-, antagonist-, or inverse agonist-effective fragment of M-PTH, BA058, or a PTHR-1 or PTHR-2 agonist-, antagonist-, or inverse agonist-effective fragment of BA058, in which at least two non-adjacent α-amino acid residues are replaced with β-amino acid residues. Salts of the foregoing peptide analogs are also within the scope of this disclosure.

In other PTH analogs disclosed herein, at least three, at least four, or at least five non-adjacent α-amino acid residues are replaced with β-amino acid residues. Again, the at least three, four or five α-amino acid residues may optionally be replaced with a corresponding number of β-amino acid residues having the same side-chain as the α-amino acid residues they replace. Or at least one of the at least three, four or five α-amino acid residues may optionally be replaced with a cyclically constrained β-amino acid residue. When at least three β-amino acids appear, the at least three β-amino acid residues may optionally appear in a pattern comprising αβαβαβ, ααβααβααβ, αααβαααβαααβ, and ααβαααβααβ. When at least five β-amino acids appear in the PTH analog, the at least five β-amino acid residues may optionally appear in a pattern comprising αβαβαβαβαβ, ααβααβααβααβααβ, αααβαααβαααβαααβαααβ, and ααβαααβααβαααβααβ.

In another version, the PTH analogs comprise thirty four (34) N-terminal residues of a mammalian parathyroid hormone, PTH(1-34), in which at least three non-adjacent α-amino acid residues are replaced with a β-amino acid residues. Again, the at least three α-amino acid residues may optionally be replaced with three β-amino acid residues having the same side-chain as the α-amino acid residues they replace. Optionally, at least one of the at least three non-adjacent α-amino acid residues may be replaced with a cyclically constrained β-amino acid residue. The β-amino acid residues may appear in any pattern, so long as they are non-adjacent, including the patterns noted earlier.

Specific PTH analogs disclosed herein include:

```
                                         (SEQ. ID. NO: 1)
A3: SVSEIQLMHNLGKHLNSMERVEWLRKKLQDVHNF-NH2, (SEQ. ID. NO: 2)
B3: SVSEIQLMHNLGKHLNSMERVEWLRKKLQDVQNF-NH2, (SEQ. ID. NO: 3)
C3: SVSEIQLMHNLGKHLNSMERVEWLRKKLQDVHNF-NH2, (SEQ. ID. NO: 4)
D3: SVSEIQLMHNLGKHLNSMERVEWLRKKLQDVHNF-NH2, (SEQ. ID. NO: 5)
A5: SVSEIQLMHNLGKHLNSMERVEWLRKKLQDVHNF-NH2, (SEQ. ID. NO: 6)
B5: SVSEIQLMHNLGKHLNSMERVEWLRKKLQDVQNF-NH2, (SEQ. ID. NO: 7)
C5: SVSEIQLMHNLGKHLNSMERVEWLRKKLQDVHNF-NH2, (SEQ. ID. NO: 8)
D5: SVSEIQLMHNLGKHLNSMERVEWLRKKLQDVHNF-NH2, (SEQ. ID. NO: 9)
D6: SVSEIQLMHNLGKWLNSMERVEWLRKKLQDVHNF-NH2,
and
                                         (SEQ. ID. NO: 10)
D7: SVSEIQLMHNLGKWLNSMERVEWLRKKLQDVHNF-NH2
``` wherein bold, underlined residues designate β³ residues having the side chain of the α residue indicated by the letter, and salts thereof.

The PTH analogs disclosed herein may be agonists of parathyroid hormone receptor-1. Alternatively, other PTH analogs disclosed herein may be antagonists of parathyroid hormone receptor-1

Also disclosed herein are pharmaceutical compositions for treating hypoparathyroidism. The composition comprises a parathyroid hormone receptor agonist-effective amount of a compound or salt thereof as disclosed herein in combination with a pharmaceutically suitable carrier. Also disclosed herein is a method of treating hypoparathyroidism in a mammalian subject, including a human subject. The method comprising administering to the subject a parathyroid hormone receptor agonist-effective amount of a pharmaceutical composition as described herein.

BRIEF DESCRIPTION OF THE DRAWINGS

FIG. 2 presents the sequences of the α/β-peptides used in the Examples. The conventional single-letter code is used to indicate proteinogenic a residues. Bold indicate the positions of β³ residues, which have the side chain of the α residue indicated by the letter. All oligomers contained the native α residues ($H_2$N-SVSEIQLMH) at the first nine positions. In α/β-peptides B3 and B5, β³-hGln is used in place of histidine-32; in D6 and D7, β³-hTrp is used in place of histidine-14

FIG. 3A shows the effects of PTH(1-34), B5 and D6 on blood $Ca^{2+}$ levels in mice. C57BL/6 mice (n=5 per compound), were injected subcutaneously with vehicle or vehicle containing PTH(1-34), B5 or D6 at 20 nmol/kg body weight. Blood was withdrawn just prior to injection (t=0) or at times thereafter. * $p<0.05$ vs. vehicle, # $p<0.05$ vs. PTH(1-34). FIG. 3B shows concentrations of PTH(1-34) or α/β-peptide B5 or D6 in plasma from blood withdrawn from mice (n=3 per compound) at times indicated following subcutaneous injection at the dose described for FIG. 3A. Compound concentrations were determined by submitting plasma to a cAMP GloSensor assay, quantification of luminescence readout, and conversion to peptide concentration via standard curve. (See Examples for complete details). * $p<0.05$ vs. vehicle, # $p<0.05$ vs. PTH(1-34) using −log [compound] concentrations. See also FIGS. 12A, 12B and 12C.

FIG. 6A depicts results for A3-D3 binding to $R^O$; FIG. 6B depicts results for A5-D5 binding to $R^O$; FIG. 6C depicts results for D6 and D7 binding to $R^O$; FIG. 6D depicts results for A3-D3 binding to RG; FIG. 6E depicts results for A5-D5 binding to RG; and FIG. 6F depicts results for D6 and D7 binding to RG. The PTH-derived α/β-peptides indicated in the legends were assessed by radio-ligand competition methods for binding to the $R^O$ (FIGS. 6A, 6B, and 6C) and RG (FIGS. 6D, 6E, 6F) forms of the human PTHR-1. Assays were performed in membranes prepared from COS-7 cells transfected to express PTHR-1; for RG assays the cells were co-transfected with a high affinity $G_{\alpha}s$ mutant.[7] $R^O$ assays used $^{125}$I-PTH(1-34) radio-ligand and contained an excess of GTPγS.[8] RG assays used $^{125}$I-M-PTH(1-15) radio-ligand. Data are means (±SEM) of n≥4 experiments, each performed in duplicate.

FIGS. 7A, 7B, 7C, 7D, 7E, and 7F constitute a series of graphs depicting binding of various analogs to the $R^O$ and RG forms of rat PTHR-1. FIG. 7A depicts results for A3-D3 binding to $R^O$; FIG. 7B depicts results for A5-D5 binding to $R^O$; FIG. 7C depicts results for D6 and D7 binding to $R^O$; FIG. 7D depicts results for A3-D3 binding to RG; FIG. 7E depicts results for A5-D5 binding to RG; and FIG. 7F depicts results for D6 and D7 binding to RG. The PTH-derived α/β-peptides indicated in the legends were assessed by radio-ligand competition methods for binding to the $R^O$ (FIGS. 7A, 7B, and 7C) and RG (FIGS. 7D, 7E, 7F) forms of the rat PTHR-1. Assays were performed in membranes prepared from COS-7 cells transfected to express PTHR-1; for RG assays the cells were co-transfected with a high affinity $G_{\alpha}s$ mutant.[8] $R^O$ assays used $^{125}$I-PTH(1-34) radio-ligand and contained an excess of GTPγS.[8] RG assays used $^{125}$I-M-PTH(1-15) radio-ligand. Data are means (±SEM) of n≥4 experiments, each performed in duplicate.

FIGS. 8A, 8B, and 8C constitute a series of graphs depicting cAMP responses in GP-2.3 cells expressing wild-type human parathyroid hormone receptor 1 (PTHR-1-WT). FIG. 8A depicts results for cells treated with α/β-peptides A3-D3; FIG. 8B depicts results for cells treated with α/β-peptides A5-D5; FIG. 8C depicts results for cells treated with α/β-peptides D6 and D7. HEK-293 cells stably transfected to express the GloSensor™-brand cAMP reporter (Promega, Fitchburg, Wis.) and human PTHR-1(GP-2.3 cells) were treated with varying concentrations of the indicated PTH-based α/β-peptide for 12-14 minutes, and intracellular cAMP was assessed as luciferase-derived luminescence. Data are means (±SEM) of n>4 experiments, each performed in duplicate.

FIGS. 9A, 9B, and 9C constitute a series of graphs depicting cAMP responses in GR-35 cells expressing rat PTHR-1-WT. FIG. 9A depicts results for cells treated with α/β-peptides A3-D3; FIG. 9B depicts results for cells treated with α/β-peptides A5-D5; FIG. 9C depicts results for cells treated with α/β-peptides D6 and D7. HEK-293 cells stably transfected to express the Glosensor cAMP reporter, and rat PTHR-1 (GR-35 cells) were treated with varying concentrations of the indicated PTH-based α/β-peptide for 12-14 minutes, and intracellular cAMP was assessed as luciferase-derived luminescence. Data are means (±SEM) of n>4 experiments, each performed in duplicate. See also Tables 6 and 7 in the Examples.

FIGS. 10A, 10B, 10C, and 10D constitute a series of graphs correlating $R^O$/RG data. Negative log [$R^O$ or RG $IC_{50}$] values were plotted against negative log [$EC_{50}$] values. Degree of correlation was judged by the quality of the fit ($R^2$) of a linear model applied to the data. FIG. 10A depicts the correlation data for human PTHR-1 $R^O$ vs. cAMP; FIG. 10B depicts the correlation data for rat PTHR-1 $R^O$ vs. cAMP; FIG. 10C depicts the correlation data for human PTHR-1 RG vs. cAMP; FIG. 10D depicts the correlation data for rat PTHR-1 RG vs. cAMP. This analysis shows that affinity for the RG form of human or rat PTHR-1 correlates reasonably well with agonist potency, as judged by cAMP production.

FIG. 11A depicts data for the accumulation of cAMP in the presence of vehicle, PTH(1-34) (0.3 nM), α/β-peptide B5 (3 nM), α/β-peptide D6 (0.3 nM), or M-PTH(1-34) (0.3 nM). Ligand was applied and luminescence was recorded for 14 minutes thereafter. FIG. 11B depicts data for the accumulation of cAMP following ligand wash-out in cells expressing the rPTHR-1. The cells from FIG. 11A were removed from the plate reader at the end of the 14-min "ligand-on" phase, rinsed twice to remove unbound ligand, treated with fresh medium containing luciferin, and luminescence was again recorded for an additional 120 min of "wash-out." Luminescence was recorded using a PerkinElmer Envision plate reader; cells were preloaded with luciferin for 30 min before ligand addition.

FIG. 12A presents the data for bioavailability over a time course assessed using the raw luminescence response following application of 2 μL of plasma from mice injected with PTH(1-34) or α/β-peptide-peptide B5 or D6 to GP2.3 cells. FIG. 12 B is a magnification of FIG. 12A to highlight the data from early time points. FIG. 12 C is a dose-response curve used to convert the raw luminescence time course found in FIG. 12A to the peptide concentration time course found in FIG. 3B. This curve was generated from a single assay run immediately before assessing the raw luminescence time course. Each data point is the average of duplicate conditions with error bars representing S.E.M. * p<0.05 vs. vehicle, # p<0.05 vs. PTH(1-34) based on log(relative luminescence) concentrations.

DETAILED DESCRIPTION

Abbreviations and Definitions

Figure 1:
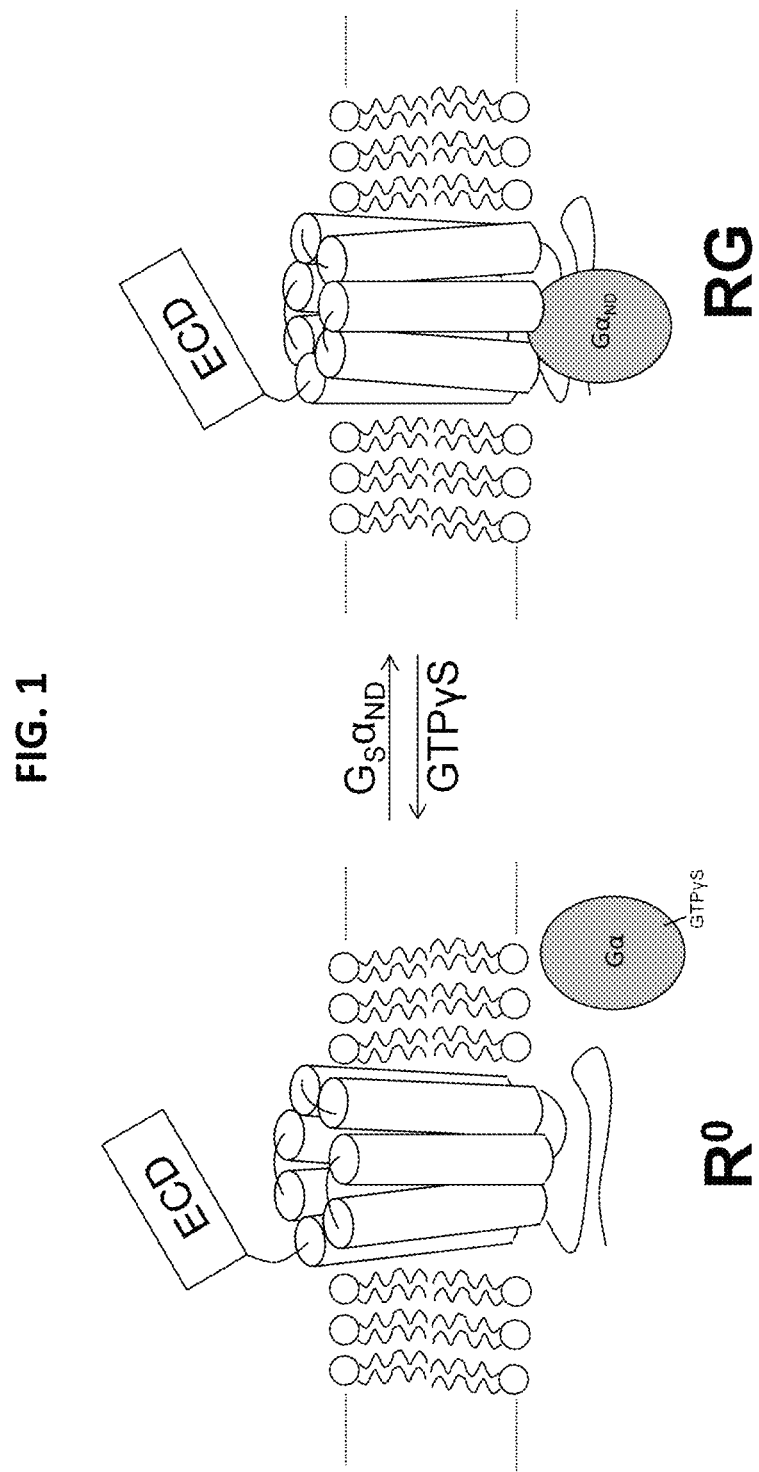
FIG. 1 is a schematic diagram of the G-protein uncoupled ($R^0$) and coupled (RG) conformational states of PTHR-1. "ECD" is extracellular domain.

ACPC=2-aminocyclopentane carboxylic acid.

Agonist, Antagonist, Inverse Agonist: An inverse agonist is an agent that binds to the same receptor as an agonist but induces a pharmacological response opposite to that agonist. A prerequisite for an inverse agonist response is that the receptor must have a constitutive level of activity in the absence of any ligand. An agonist increases the activity of a receptor above its basal level, whereas an inverse agonist decreases the activity below the basal level. An antagonist binds to the receptor and blocks the activity of both agonists and inverse agonists.

APC=2-aminopyrrolidine-4-carboxylic acid.

"Cyclically constrained" when referring to a β-amino acid or β-amino acid residue means a β-amino acid or β-amino acid residue in which the α-position and β-position carbon atoms in the backbone of the β-amino acid are incorporated into a substituted or unsubstituted $C_4$ to $C_{10}$ cycloalkyl, cycloalkenyl, or heterocycle moiety, wherein heterocycle moieties may have 1, 2, or 3 heteroatoms selected from the group consisting of N, S, and O. Generally preferred cyclically constrained β-amino acids have the α-position and β-position carbon atoms in the backbone incorporated into a substituted or unsubstituted $C_5$ to $C_8$ cycloalkyl, cycloalkenyl, or heterocycle moiety having one or more N, S, or O atoms as the heteroatom. Within any given PTH analog, the cyclically constrained β-amino acid residues may be the same or different.

DIEA=N,N-diisopropylethylamine.
DMF=dimethylformamide.
GPCR=G protein-coupled receptor.
HBTU=2-(1H-benzotriazole-1-yl)-1,1,3,3-tetramethyluronium hexafluorophosphate.
HOBt=N-hydroxybenzotriazole.
MALDI-TOF-MS=matrix-assisted laser desorption/ionization time-of-flight mass spectrometry.
PTH=mammalian parathyroid hormone (including human PTH), its proprotein, its preproprotein, and any PTHR-1 agonist-effective fragment thereof. In humans, the corresponding PTH gene encodes and expresses a preproprotein comprising the amino acid sequence:

(SEQ. ID. NO: 11)
MIPAKDMAKVMIVMLAICFLTKSDGKSVKKRSVSEIQLMHNLGKHLNSME

RVEWLRKKLQDVHNFVALGAPLAPRDAGSQRPRKKEDNVLVESHEKSLGE

ADKADVNVLTKAKSQ.

After post-translational processing, human PTH comprises the amino acid sequence (SEQ. ID. NO: 12)
SVSEIQLMHNLGKHLNSMERVEWLRKKLQDVHNFVALGAPLAPRDAGSQR

PRKKEDNVLVESHEKSLGEADKADVNVLTKAKSQ.

See U.S. National Center for Biotechnology Information (NCBI) reference sequence NP_000306 (online at http://www.ncbi.nlm.nih.gov/protein/NP_000306.1).

PTHR-1=parathyroid hormone receptor 1. hPTHR-1 designates the human version of the receptor; rPTHR-1 designates the rat version of the receptor. The prefix or suffix WT in combination with either designates "wild-type."
PTHrP=parathyroid hormone-related protein.
TFA=trifluoroacetic acid.
TBS=tris-buffered saline (i.e., tris(hydroxymethyl)aminomethane).
WT=wild-type.

The amino acid residues in the compounds disclosed herein may either be present in their D or their L configuration. The terms "peptide" and "polypeptide" are used synonymously and refer to a polymer of amino acids which are linked via amide linkages. β-amino acid residues may be linear, unsubstituted, or substituted at the α- or β-position carbon atoms of the backbone (i.e., at the $β^2$ or $β^3$ carbon atoms) or may be conformationally constrained by a cyclic group encompassing the α and β backbone carbon atoms of the inserted β-amino acid residue. While not required, it is preferred that the β-amino acid residues are corresponding $β^3$ versions of the α-amino acid residues they replace. That is, the side-chain on the β-position carbon (the $β^3$ carbon) in the β-amino acid residue is the same as the side-chain on the α-amino acid residue it replaces and the α-position carbon (the $β^2$ carbon) in the β-amino acid residue is unsubstituted.

"Pharmaceutically suitable salts" means salts formed with acids or bases the addition of which does not have undesirable effects when administered to mammals, including humans. Preferred are the salts with acids or bases listed in the U.S. Pharmacopoeia (or any other generally recognized pharmacopoeia) for use in humans. A host of pharmaceutically-suitable salts are well known in the art. For basic active ingredients, all acid addition salts are useful as sources of the free base form even if the particular salt, per se, is desired only as an intermediate product as, for example, when the salt is formed only for purposes of purification, and identification, or when it is used as intermediate in preparing a pharmaceutically-suitable salt by ion exchange procedures. Pharmaceutically-suitable salts include, without limitation, those derived from mineral acids and organic acids, explicitly including hydrohalides, e.g., hydrochlorides and hydrobromides, sulphates, phosphates, nitrates, sulphamates, acetates, citrates, lactates, tartrates, malonates, oxalates, salicylates, propionates, succinates, fumarates, maleates, methylene bis b hydroxynaphthoates, gentisates, isethionates, di p toluoyltartrates, methane sulphonates, ethanesulphonates, benzenesulphonates, p toluenesulphonates, cyclohexylsulphamates, quinates, and the like. Base addition salts include those derived from alkali or alkaline earth metal bases or conventional organic bases, such as triethylamine, pyridine, piperidine, morpholine, N methylmorpholine, and the like. Other suitable salts are found in, for example, Handbook of Pharmaceutical Salts, P. H. Stahl and C. G. Wermuch, Eds., © 2002, Verlag Helvitica Chemica Acta (Zurich, Switzerland) and S. M. Berge, et al., "Pharmaceutical Salts," *J. Pharm. Sci.*, 66: p. 1-19 (January 1977), both of which are incorporated herein by reference.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods, compounds and compositions of the present invention can comprise, consist of, or consist essentially of the essential elements and limitations of the method described herein, as well as any additional or optional ingredients, components, or limitations described herein or otherwise useful in synthetic organic chemistry, pharmacy, pharmacology, and the like.

Overview:

Alternative activated conformations of a receptor protein are likely to differ from one another in subtle ways.[4] Thus, making subtle modifications to a natural agonist could be fruitful for making compounds with diverse selectivities among functional receptor states. In the present invention, an unconventional strategy was used in which the backbone of a natural PTHR-1 agonist was altered, rather than the side-chain complement. The results show that backbone-modification can rapidly identify potent agonists with divergent receptor state selectivity patterns relative to a prototype peptide.

Design of PTH(1-34) Analogs:

PTH is an 84-residue protein that controls key physiological processes, including the maintenance of extracellular levels of calcium and phosphate.[9] The N-terminal fragment PTH(1-34) matches full-length PTH in potency and efficacy at PTHR-1 and is the active ingredient in the osteoporosis drug teriparatide.[11] A crystal structure of the human PTHR-1 extracellular domain (ECD) bound to PTH(15-34) reveals that this segment forms an α-helix upon association with the receptor.[12] The bioactive conformation of the N-terminal portion of PTH is unknown. PTH(1-34) analogs containing a regular αααβ pattern in the C-terminal region were fabricated and their in vivo activity as PTHR-1 agonists explored. Exemplary α/β-peptide analogs according to the present invention (working examples) are shown in FIG. 2. Native α residues in the wild-type PTH were replaced with $\beta^3$ homologs. Thus, in the exemplary compounds the natural side chain sequence was maintained in the resulting α/β-peptides, but the backbone contained additional $CH_2$ units.

Isomers A3, B3, C3 and D3 represent the four possible ways in which three $\alpha \rightarrow \beta^3$ replacements can be made closest to the C-terminus following the αααβ pattern. These α/β-peptides were prepared via conventional solid-phase synthesis. Protected forms of many $\beta^3$ amino acids are commercially available, but not $\beta^3$-homohistidine. Therefore a $\beta^3$-homoglutamine was placed at position 32 of B3. The His32→Ala variant of PTH(1-34) exhibits full affinity for PTHR-1 ECD[12], which suggests that the side chain at this position does not play a critical role in binding to hPTHR-1.

Receptor Binding and Activation:

Well-established radio-ligand-displacement assays[5-7] were used to determine whether the $\alpha \rightarrow \beta^3$ replacements in A3-D3 lead to variations in affinities for the $R^0$ or RG state of hPTHR-1 relative to the prototype α-peptide PTH(1-34) See Table 1 and Table 4 in the Examples.[14,15] Agonist activity was determined by monitoring cAMP production in HEK293 cells that stably express PTHR-1 and the GloSensor-brand cAMP reporter and PTHR-1.[16] Quite unexpectedly, all of the α/β-peptides A3, B3, C3, and D3 all proved to be full agonists of hPTHR-1 (maximum cAMP response comparable to that of PTH(1-34); see Table 1 and Table 6 in the Examples).

TABLE 1

Binding and signaling properties of PTH analogs for hPTHR-1[a]

| | Binding (hPTHR-1)[b-d] | | cAMP (hPTHR-1)[e] | |
|---|---|---|---|---|
| | $R^0$ $IC_{50}$, nM | RG $IC_{50}$, nM | $EC_{50}$, nM | Max[f] |
| PTH (1-34) | 1.1 | 0.10 | 0.17 | 1.00 |
| A3 | 130 | 0.36 | 0.29 | 1.07 |
| B3 | 80 | 0.13 | 0.11 | 1.08 |
| C3 | 11 | 0.42 | 0.58 | 1.03 |
| D3 | 1.1 | 0.11 | 0.16 | 1.04 |
| A5 | 310 | 2.71 | 1.66 | 1.12 |
| B5 | 19 | 0.086 | 0.11 | 0.98 |
| C5 | 11 | 0.40 | 0.20 | 1.01 |
| D5 | 1.7 | 0.28 | 0.26 | 1.03 |
| D6 | 2.0 | 0.065 | 0.13 | 0.87 |
| D7 | 3.5 | 0.24 | 0.39 | 0.85 |

[a]Values are means of n ≥4 experiments, each performed in duplicate. See Tables 4 and 6 in the Examples for uncertainties associated with each parameter.
[b]Assays were performed in membranes prepared from COS-7 cells transiently transfected to express WT hPTHR-1.
[c]$R^0$ assays used $^{125}$I-PTH(1-34) tracer and contained GTPγS (1 × 10$^{-5}$M).
[d]RG assays used $^{125}$I-M-PTH(1-15) tracer and membranes from cells co-transfected to express a high affinity $G_{\alpha}s$ mutant.
[e]Assays were performed in GP-2.3 cells expressing hPTHR-1-WT and the luciferase-based, Glosensor cAMP reporter.
[f]Values are luminescence counts per second relative to PTH(1-34) observed 12-16 minutes after ligand addition.

The results of the binding and activity assays support the hypothesis that subtle modification of a prototype α-peptide via multiple $\alpha \rightarrow \beta^3$ replacements enables the discovery of agonists with variations in receptor-state affinity profile relative to the α-peptide itself. α/β-Peptides A3-D3 are very similar to PTH(1-34) in terms of affinity for the RG state of hPTHR-1, but the affinities of A3-D3 for the $R^0$ state of hPTHR-1 vary considerably. For example, D3 matches PTH(1-34) in $R^0$ affinity, while A3 binds >100-fold less strongly to the $R^0$ state. These two α/β-peptides differ only in the locations of the three added —$CH_2$— units within the backbone. All four α/β-peptides are potent agonists of hPTHR-1. Their $EC_{50}$ values are comparable to that of PTH(1-34), while the value for C3 is modestly higher.

Second-Generation Analogs:

The α/β-Peptides A5, B5, C5 and D5 maintain the αααβ backbone patterns of A3-D3 and contain two additional $\alpha \rightarrow \beta^3$ replacements. The $\beta^3$ residues in A5-D5 are distributed throughout the segment present in the PTH(15-34)+ECD co-crystal structure; PTH(15-34) is fully α-helical in this complex.[12] α/β-Peptides B5-D5 are similar to their counterparts among B3-D3 in terms of affinities for the $R^0$ and RG states of hPTHR-1 and in terms of agonist efficacy and potency. Relative to A3, A5 shows somewhat diminished affinity for $R^0$ and RG and somewhat lower potency, suggesting that the additional $\alpha \rightarrow \beta^3$ replacements exert a modestly deleterious impact on recognition by hPTHR-1 in this case. Position 19 is Glu in A3 but $\beta^3$-hGlu in A5; side chain modification at this position in conventional PTH analogs (exclusively α residues) can influence binding to and activation of hPTHR-1.[17] Moreover, replacing Glu19 with β-hGly (no side chain) diminished agonist potency.[18] Thus, it is possible that the differences between A3 and A5 as hPTHR-1 agonists arise from the backbone modification at position 19 in the latter. The results for B3 and B5, however, show that $\alpha \rightarrow \beta^3$ replacement is not intrinsically problematic for interfacial residues. The side chains of Arg20, Leu24 and Leu28 of PTH(15-34) all make contacts with the ECD,[12] but α→β³ replacement at all of these positions, as in B5, does not erode agonist potency or RG binding affinity.

α/β-Peptide D5 is very similar to PTH(1-34) in terms of affinity for the hPTHR-1 $R^0$ and RG states as well as agonist efficacy and potency. Therefore this ααaβ pattern was extended to generate D6 and D7. Both of these α/β-peptides displayed affinity and activity profiles similar to that of PTH(1-34). D6 and D7 contain β³-hTrp at position 14, but PTH(1-34) has His at this position. Previous studies of PTH α-peptide analogs indicate that replacing the native His with Trp at this site may modestly improve agonist activity.[19] For the full set of α/β-peptides (Table 1), the trend among $IC_{50}$ values for the RG state correlates well with the trend in $EC_{50}$ values as has previously been observed among α-peptide analogs of PTH.[8] See also the Examples and FIGS. 10A-10D. This similarity suggests that the RG conformation of hPTHR-1 is close to the receptor conformation required to induce Ga to exchange bound GDP for GTP.

Calcemic Effects in Mice:

α/β-Peptides B5 and D6 were selected for comparison with PTH(1-34) in vivo. These two compounds incorporate a substantial complement of β residues but are indistinguishable from PTH(1-34) in terms of potency as agonists of hPTHR-1. PTH(1-34), B5 and D6 are similar in terms of affinity for the hPTHR-1 RG state, but the two α/β-peptides diverge significantly in terms of affinity for the $R^0$ state, with D6 binding comparably to PTH(1-34), but B5 binding an order of magnitude more weakly. Because the in vivo assessment involves mice, the in vitro studies involving human PTHR-1 (Table 1) were performed along with analogous measurements based on rat PTHR-1 (rPTHR-1) (Table 2; Examples, Table 4). The rat and mouse receptors have 98% sequence identity, while the human and mouse receptors have only 90% sequence identity. As observed for hPTHR-1, B5 displays significantly weaker affinity for the $R^0$ state of rPTHR-1 relative to D6 or PTH(1-34); however, B5 also exhibits moderately weaker affinity for RG and slightly weaker potency relative to PTH(1-34). D6 is comparable to PTH(1-34) in terms of RG affinity and agonist potency for rPTHR-1, but D6 shows somewhat weaker affinity for the $R^0$ state relative to PTH(1-34).

TABLE 2

Binding and signaling properties of PTH analogs for rPTHR-1[a]

| | Binding (rPTHR-1)[b-d] | | cAMP (rPTHR-1)[e] | |
|---|---|---|---|---|
| | $R^0$ $IC_{50}$, nM | RG $IC_{50}$, nM | $EC_{50}$, nM | Max[f] |
| PTH(1-34) | 0.8 | 0.42 | 0.42 | 1.00 |
| B5 | 65 | 4.2 | 1.45 | 0.78 |
| D6 | 6.1 | 0.81 | 0.33 | 0.76 |

[a]Values are means of n ≥ 4 experiments, each performed in duplicate. See SI tables S2 + S4 for uncertainties associated with each parameter.
[b]Assays were performed in membranes prepared from COS-7 cells transiently transfected to express WT rPTHR-1.
[c]$R^0$ assays used $^{125}$I-PTH(1-34) tracer and contained GTPγS (1 × $10^{-5}$M).
[d]RG assays used $^{125}$I-M-PTH(1-15) tracer and membranes from cells co-transfected to express a high affinity $G_{\alpha S}$ mutant.
[e]Assays were performed in GP-2.3 cells expressing rPTHR-1-WT and the luciferase-based, Glosensor cAMP reporter.
[f]Values are luminescence counts per second relative to PTH(1-34) observed 12-16 minutes after ligand addition.

Figure 3A:
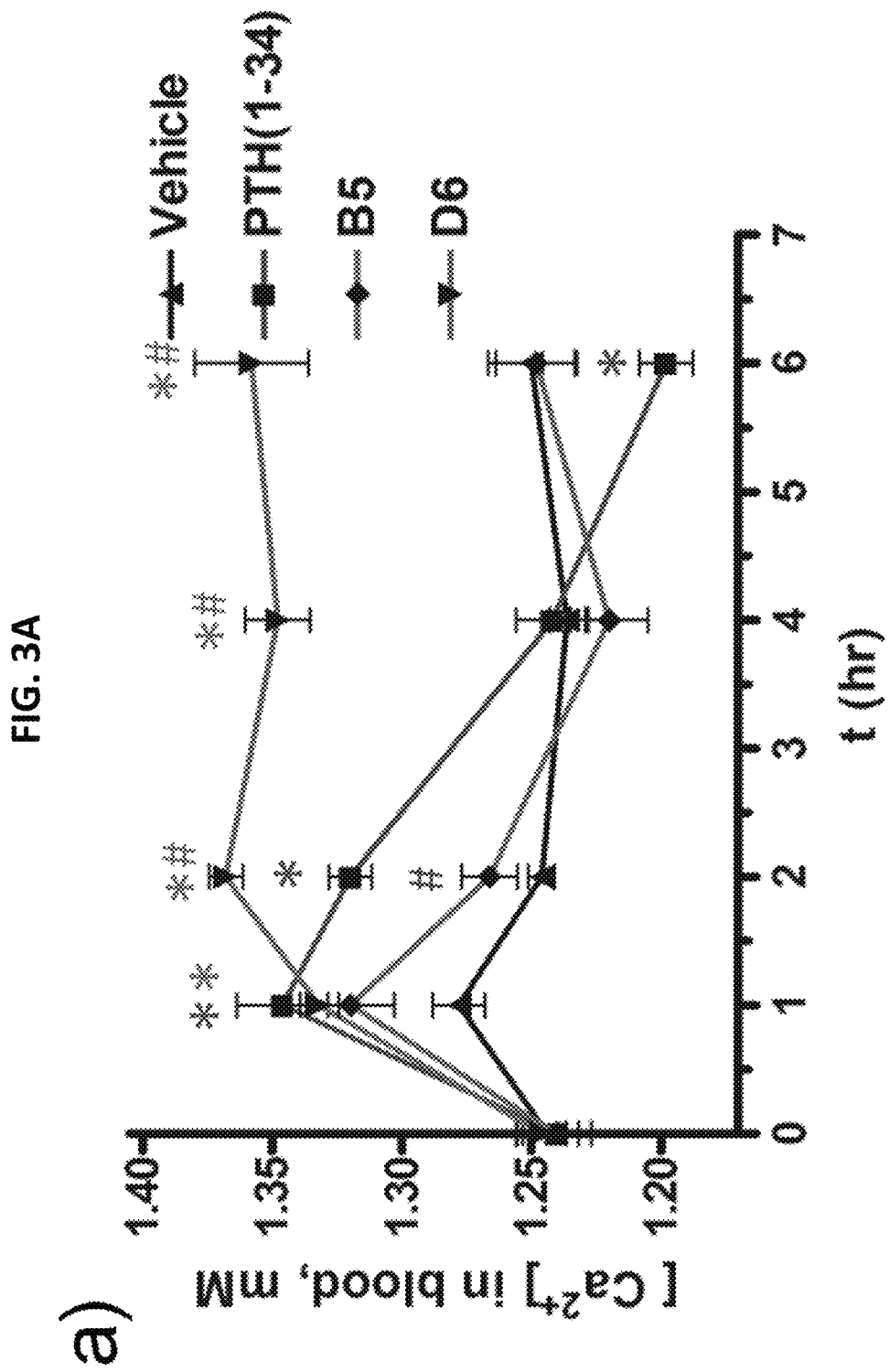
FIGS. 3A and 3B are graphs depicting in vivo properties of PTH(1-34) or α/β-peptide analogs B5 and D6.

The calcemic responses of mice vary considerably upon subcutaneous injection of PTH(1-34), B5 or D6. See FIG. 3A. PTH(1-34) causes a transient rise in the blood concentration of $Ca^{2+}$, which peaks after about one hour.[8] α/β-Peptide B5 causes a more transient rise in $Ca^{2+}$ concentration relative to PTH(1-34), while the $Ca^{2+}$ rise caused by D6 is sustained, with no diminution six hours after injection.

Figure 3B:
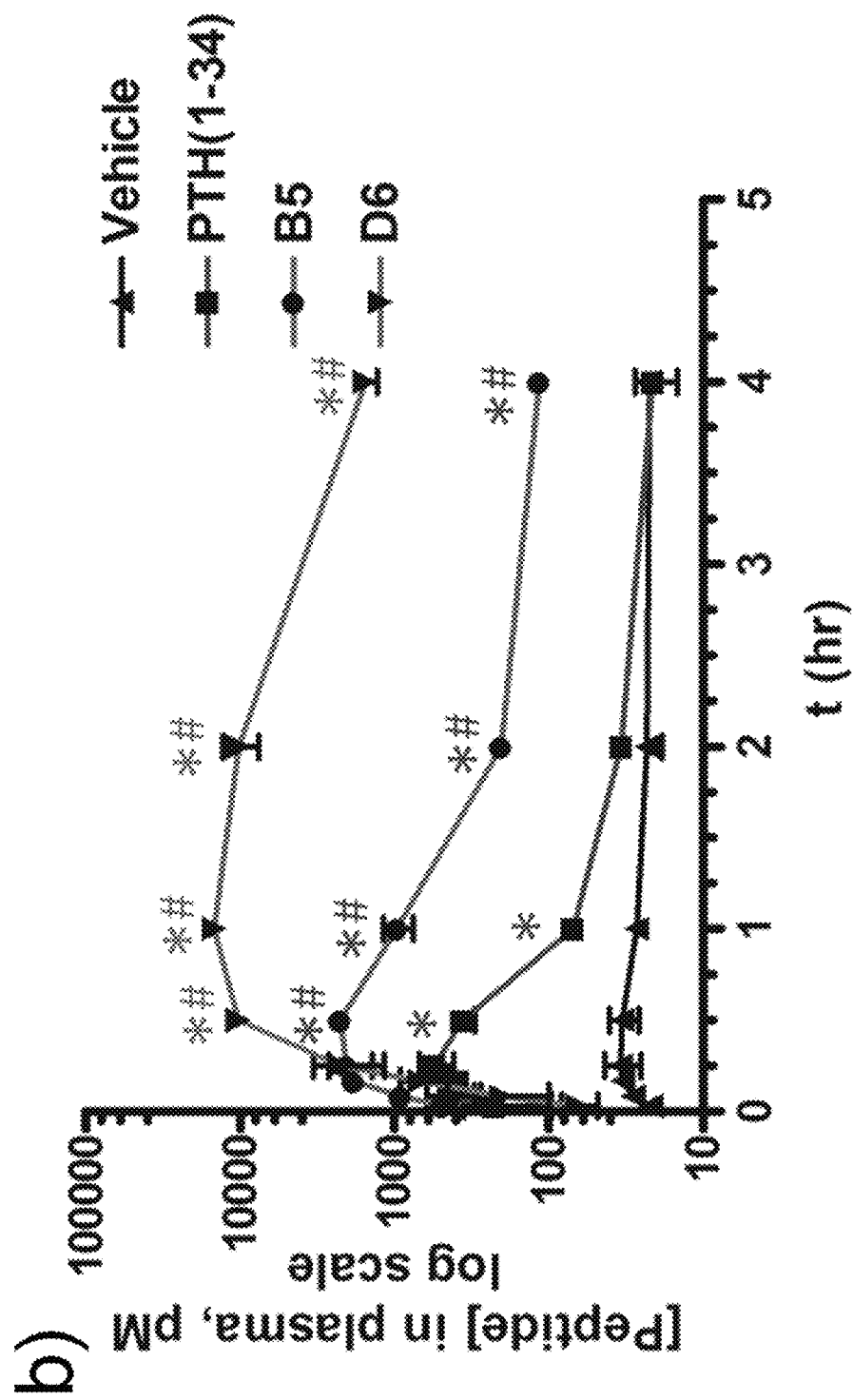
Figure 4A:
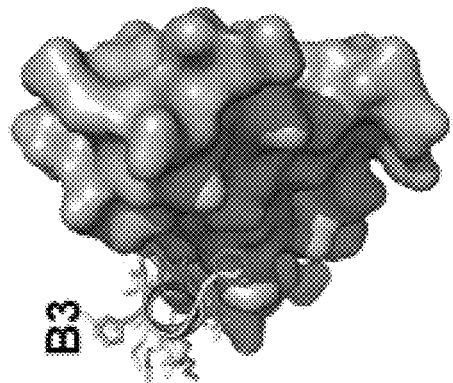
FIGS. 4A, 4B, 4C, and 4D Positions of the α→β modification sites in α/β-peptides A3 (FIG. 4A), B3 (FIG. 4B), C3 (FIG. 4C) and D3 (FIG. 4D) as indicated on the crystal structure of PTH(15-34) bound to the extracellular domain of PTHR-1, PDB 3C4M (ref. 12). The ECD is shown as a gray surface, and the peptide ligand is shown in yellow, with sites of α→β modification for each α/β-peptide shown in blue. ECD residues not interacting with PTH (residues 155-175) have been hidden to enable visualization of the PTH-PTHR-1 interaction. The perspective coincides with the α-helical axis of PTH(15-34). The four images are identical except for the location of the blue residues in the helical ligand.
Figure 4B:
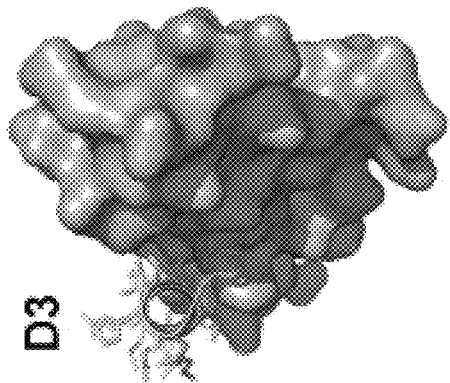
Figure 4C:
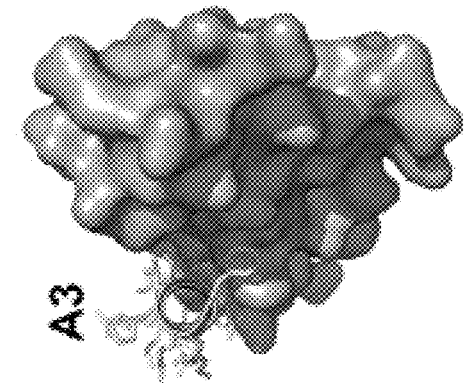
Figure 4D:
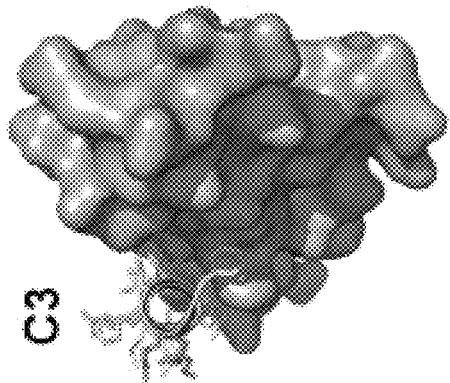

FIG. 3B shows how the concentrations of PTH(1-34), B5 and D6 vary in the mouse bloodstream. The differences in calcemic effect duration (FIG. 3A) cannot be explained simply in terms of the pharmacokinetics data (FIG. 3B), because PTH(1-34) causes a longer-lasting elevation of $Ca^{2+}$ concentration than does B5, but the level of PTH(1-34) in the bloodstream is consistently lower than the level of B5. α/β-Peptide D6 persists even longer in the bloodstream than does B5.

Okazaki et al. have proposed that the calcemic effect duration resulting from injection of a PTHR-1 agonist is controlled, at least in part, by affinity for the $R^0$ state of the receptor.[8] According to this hypothesis, agonists with high $R^0$ affinity can remain bound to the receptor through multiple cycles of $G_\alpha$ binding and release, which should induce prolonged signaling.[7] The increased calcemic effect duration observed for PTH(1-34) relative to B5 can be explained in terms of this hypothesis, because PTH(1-34) has a substantially higher affinity for the $R^0$ state of rPTHR-1 than does B5. The slight diminution in rPTHR-1 agonist potency of B5 relative to PTH(1-34) may also contribute to the weaker in vivo response induced by B5 relative to PTH(1-34). However, the proposed correlation between $R^0$ affinity and signaling duration cannot explain the prolonged calcemic effect observed for α/β-peptide D6 relative to PTH(1-34), because D6 has weaker affinity than PTH(1-34) for the $R^0$ state of rPTHR-1. Without being limited to any underlying biological mechanism, it is thought that the prolonged signaling manifested by D6 arises from pharmacokinetics: D6 persists much longer in the mouse bloodstream than does PTH(1-34). This difference seems likely to stem from resistance to proteolysis conferred by the β residues in D6. Indeed, in vitro studies with an isolated protease that cleaves in the C-terminal region of PTH(1-34) show that α/β-peptide D6 is a poorer substrate than is the α-peptide. See FIGS. 5A, 5B, and 5C. The pathways by which PTH is removed from circulation have not been fully elucidated, but enzymatic degradation probably contributes to the rapid disappearance of PTH(1-34) in vivo.[20] The behavior of B5, however, shows that simply increasing persistence in the bloodstream is not sufficient to achieve prolonged signaling via PTHR; instead, the calcemic effect duration appears to depend on an interplay between affinity for the receptor $R^0$ state and agonist pharmacokinetics.

Figures 11A, 11B:
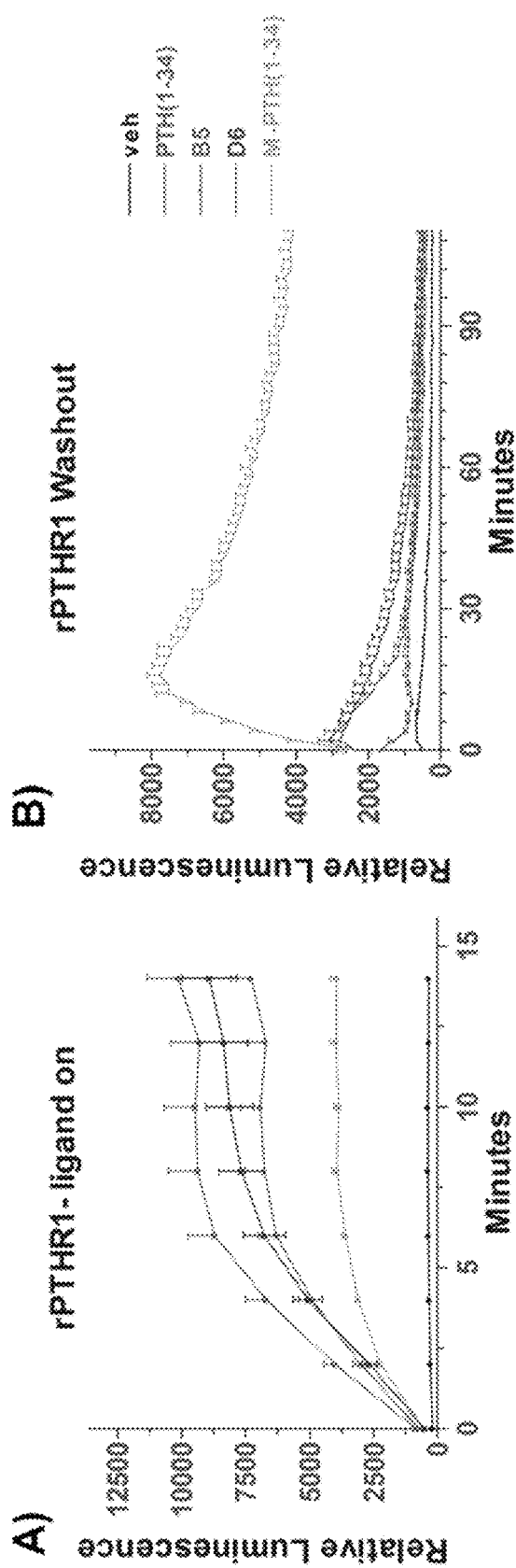
FIGS. 11A and 11B present the results of rPTHR-1 washout experiments. Assays of cAMP accumulation were performed using HEK-293-derived cell lines stably transfected to express the luciferase-based cAMP GloSensor™-brand protein along with WT-rPTHR-1 (GR-35 cells). Data are means (±SEM) of n=3 (M-PTH) or n=5 experiments, each performed in quadruplicate.

Washout Assays of Receptor Activation:

Additional cell-based assays were pursued to elucidate the variation among in vivo responses observed for PTH(1-34), B5 and D6. These "washout assays"[7,8,21] assess the ability of PTH(1-34), B5 and D6 to form stable ligand-receptor complexes capable of stimulating prolonged cAMP responses. See the Examples at Table 7 and in FIGS. 11A and 11B. The ability of a peptide to elicit prolonged cAMP responses via PTHR-1 following washout typically correlates with the affinity of that peptide for the $R^0$ state.[7,8,21] As expected for an agonist showing weak rPTHR-1 $R^0$ affinity, B5 stimulates a short-lived cAMP response in rPTHR-1-expressing cells following washout, relative to PTH(1-34). See Examples. In contrast, D6 stimulates a cAMP response comparable to that of PTH(1-34) following washout. Combined, these results suggest that B5 forms a relatively transient complex with rPTHR-1, while D6 binds to rPTHR-1 in a more durable manner, which is comparable to the binding of PTH(1-34). These observations support the hypothesis that the weak calcemic response induced by B5 arises from weak affinity for the $R^0$ state of PTHR-1. The washout results do not explain the prolonged in vivo response induced by D6 relative to PTH(1-34), which is consistent with the hypothesis that pharmacokinetic factors, arising from resistance of the α/β-peptide to proteolysis, contribute to the long-lasting calcemic effect induced by D6 in mice.

DISCUSSION

The data show that potent PTH analogs with diverse activity profiles can be generated by replacing subsets of native α-amino acid residues with β-amino acid residues, especially homologous $\beta^3$ residues. The latter type of replacement retains the native side chain, but the backbone is extended by one —$CH_2$— unit. Comprehensive examination of αααβ backbone patterns in the α-helical C-terminal portion of PTH(1-34) reveals that altering the $\alpha \rightarrow \beta^3$ replacement sites leads to substantial variation in the relative affinities of the α/β-peptides for the RG and $R^0$ states of PTHR-1.

The contrast between the large impact of $\alpha \rightarrow \beta^3$ location on α/β-peptide affinity for the $R^0$ state of hPTHR-1 and the small impact of $\alpha \rightarrow \beta^3$ location on affinity for the RG state is intriguing from a mechanistic perspective. PTHR-1 is a member of the B-family of GPCRs, which are distinguished from most other GPCRs by the presence of large N-terminal extracellular domains.[22] The natural agonists for B-family GPCRs are long polypeptides, such as PTH and PTHrP, and the ECDs make extensive contacts with these large ligands.[23] It is widely believed that the role of the ECD is limited to enhancing affinity for agonists. Signal transduction is thought to result from ligand-induced conformational changes in the transmembrane domain, which are induced exclusively by interactions between the N-terminus of the peptide agonist and the transmembrane domain.[24] Recent results, however, indicate that direct contact between the ECD and the transmembrane domain can influence B-family GPCR signaling.[25]

The results suggest that the contribution of the ECD to overall ligand affinity can vary substantially between different conformations of a B-family GPCR. Trends among α/β-peptides A3-D3 are particularly instructive in this regard because the $\alpha \rightarrow \beta^3$ replacement sites are well within the region that is engaged by the hPTHR-1-ECD.[12] FIGS. 4A, 4B, 4C, and 4D compare the four αααβ patterns among A3-D3 in the context of the PTH(15-34)+ECD co-crystal structure.[12] The images show how the locations of the $\alpha \rightarrow \beta^3$ replacement sites vary relative to the peptide-ECD interface. The variation in $\beta^3$ residue placement among A3-D3 correlates with large differences in α/β-peptide affinity for the $R^0$ state, but all four analogs bind with similar affinities to the RG state (Table 1). This situation could arise if engagement of the G protein causes a conformational change in the transmembrane domain of PTHR-1 that tightens contacts with the N-terminal portion of an agonist but does not influence contacts between the C-terminal portion of the agonist and the ECD. Partial support for this hypothesis is found in recent structural data for an A-family GPCR, the $\beta_2$ adrenergic receptor, which show that interaction with $G_\alpha$ causes a conformational change that results in tighter agonist binding.[26] The small-molecule agonist for this A-family GPCR corresponds to the N-terminus of a polypeptide agonist for a B-family GPCR. G protein association-induced enhancement of interactions between the transmembrane domain of PTHR-1 and the N-terminal portion of agonist α/β-peptides, but not between the ECD and the C-terminal portion of agonists, could explain the very small influence on RG affinity resulting from the variation in C-terminal backbone modifications among A3-D3. Notably, the α/β-peptides A3-D3 all bind more tightly to $R^0$ than do optimized PTH(1-15) analogs[6], which indicates that $\alpha \rightarrow \beta^3$ replacements in the C-terminal portion of PTH(1-34) analogs do not abrogate favorable interactions with PTHR-1 ECD.

The variations in pharmacokinetic and pharmacodynamic properties that result from alternative $\alpha \rightarrow \beta^3$ replacement patterns among PTH(1-34) analogs indicates that the backbone modification approach described herein yields compounds of biomedical utility. The working examples shown in FIG. 2 are useful to treat any type of hypoparathyroidism in mammals, including humans, which can be eliminated, reduced, or ameliorated by administering an agonist of PTHR-1 to the mammal. The prolonged bioavailability and corresponding enhanced signal duration manifested by D6 relative to PTH(1-34), for example, leads to less frequent dosing for forms of hypoparathyroidism that currently require twice-daily PTH(1-34) injections.[8] An ideal PTH-based therapeutic agent for osteoporosis stimulates robust bone growth without hypercalcemia. The high hPTHR-1 activation potency, prolonged bioavailability and weak in vivo calcemic mobilization activity demonstrated by, for example, B5 represent favorable characteristics in this regard.

The data in the Examples show that a large signal-bearing polypeptide can give rise to a family of analogs with diverse and valuable properties via application of a readily-implemented backbone-modification strategy. Particularly significant is the finding that periodic $\alpha \rightarrow \beta^3$ replacement can identify agonists with unique selectivities between alternative GPCR conformations.

Nutritional Compositions:

The present disclosure includes nutritional compositions. Such compositions include any food or preparation for human consumption (including for enteral or parenteral consumption) which when taken into the body (a) serve to nourish or build up tissues or supply energy and/or (b) maintain, restore or support adequate nutritional status or metabolic function.

The nutritional composition comprises at least one PTH analog as described herein and may either be in a solid or liquid form. Additionally, the composition may include edible macronutrients, vitamins and minerals in amounts desired for a particular use. The amount of such ingredients will vary depending on whether the composition is intended for use with normal, healthy infants, children or adults having specialized needs such as those which accompany hyperglycemic metabolic conditions.

Examples of macronutrients which may be added to the composition include but are not limited to edible fats, carbohydrates and proteins. Examples of such edible fats include but are not limited to coconut oil, soy oil, and mono- and diglycerides. Examples of such carbohydrates include but are not limited to glucose, edible lactose and hydrolyzed starch. Additionally, examples of proteins which may be utilized in the nutritional composition include but are not limited to soy proteins, electrodialysed whey, electrodialysed skim milk, milk whey, or the hydrolysates of these proteins.

With respect to vitamins and minerals, the following may be added to the nutritional compositions described herein: calcium, phosphorus, potassium, sodium, chloride, magnesium, manganese, iron, copper, zinc, selenium, iodine, and Vitamins A, E, D, C, and the B complex. Other such vitamins and minerals may also be added.

Examples of nutritional compositions disclosed herein include but are not limited to infant formulas, dietary supplements, dietary substitutes, and rehydration compositions. Nutritional compositions of particular interest include but are not limited to those utilized for enteral and parenteral supplementation for infants, specialist infant formulas, supplements for the elderly, and supplements for those with hyperglycemia.

The nutritional composition of the present invention may also be added to food even when supplementation of the diet is not required. For example, the composition may be added to food of any type including but not limited to margarines, modified butters, cheeses, milk, yoghurt, chocolate, candy, snacks, salad oils, cooking oils, cooking fats, meats, fish and beverages.

In a preferred version, the nutritional composition is an enteral nutritional product, more preferably, an adult or pediatric enteral nutritional product. This composition may be administered to adults or children experiencing stress or having specialized needs due to chronic or acute disease states. The composition may comprise, in addition to PTH (1-34) analogs described herein, macronutrients, vitamins and minerals as described above. The macronutrients may be present in amounts equivalent to those present in human milk or on an energy basis, i.e., on a per calorie basis.

Methods for formulating liquid or solid enteral and parenteral nutritional formulas are well known in the art. An enteral formula, for example, may be sterilized and subsequently utilized on a ready-to-feed (RTF) basis or stored in a concentrated liquid or powder. The powder can be prepared by spray drying the formula prepared as indicated above, and reconstituting it by rehydrating the concentrate. Adult and pediatric nutritional formulas are well known in the art and are commercially available (e.g., Similac®-brand and Ensure®-brand formulas from Ross Products Division, Abbott Laboratories, Columbus, Ohio). A PTH(1-34) analog produced in accordance with the present disclosure may be added to commercial formulas of this type.

The energy density of the nutritional compositions in liquid form may range from about 0.6 Kcal to about 3 Kcal per ml. When in solid or powdered form, the nutritional supplements may contain from about 1.2 to more than 9 Kcals per gram, preferably about 3 to 7 Kcals per gm. In general, the osmolality of a liquid product should be less than 700 mOsm and, more preferably, less than 660 mOsm.

Pharmaceutical Compositions:

Also disclosed herein are pharmaceutical compositions comprising one or more of the PTH analogs or a pharmaceutically suitable salt thereof as described herein. More specifically, the pharmaceutical composition may comprise one or more of the PTH analogs as well as a standard, well-known, non-toxic pharmaceutically suitable carrier, adjuvant or vehicle such as, for example, phosphate buffered saline, water, ethanol, polyols, vegetable oils, a wetting agent or an emulsion such as a water/oil emulsion. The composition may be in either a liquid, solid or semi-solid form. For example, the composition may be in the form of a tablet, capsule, ingestible liquid or powder, injectable, suppository, or topical ointment or cream. Proper fluidity can be maintained, for example, by maintaining appropriate particle size in the case of dispersions and by the use of surfactants. It may also be desirable to include isotonic agents, for example, sugars, sodium chloride, and the like. Besides such inert diluents, the composition may also include adjuvants, such as wetting agents, emulsifying and suspending agents, sweetening agents, flavoring agents, perfuming agents, and the like.

Suspensions, in addition to the active compounds, may comprise suspending agents such as, for example, ethoxylated isostearyl alcohols, polyoxyethylene sorbitol and sorbitan esters, microcrystalline cellulose, aluminum metahydroxide, bentonite, agar-agar and tragacanth or mixtures of these substances.

Solid dosage forms such as tablets and capsules can be prepared using techniques well known in the art of pharmacy. For example, PTH analogs produced as described herein can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant PTH analog.

For intravenous administration, the analogs may be incorporated into commercial formulations such as Intralipid©- brand fat emulsions for intravenous injection. ("Intralipid" is a registered trademark of Fresenius Kabi AB, Uppsalla, Sweden.) Where desired, the individual components of the formulations may be provided individually, in kit form, for single or multiple use. A typical intravenous dosage of a representative PTH analog as described herein is from about 0.1 mg to 100 mg daily and is preferably from 0.5 mg to 20 mg daily. Dosages above and below these stated ranges are specifically within the scope of the claims.

Possible routes of administration of the pharmaceutical compositions include, for example, enteral (e.g., oral and rectal) and parenteral. For example, a liquid preparation may be administered, for example, orally or rectally. Additionally, a homogenous mixture can be completely dispersed in water, admixed under sterile conditions with physiologically acceptable diluents, preservatives, buffers or propellants in order to form a spray or inhalant. The route of administration will, of course, depend upon the desired effect and the medical stated of the subject being treated. The dosage of the composition to be administered to the patient may be determined by one of ordinary skill in the art and depends upon various factors such as weight of the patient, age of the patient, immune status of the patient, etc., and is ultimately at the discretion of the medical professional administering the treatment.

With respect to form, the composition may be, for example, a solution, a dispersion, a suspension, an emulsion or a sterile powder which is then reconstituted. The composition may be administered in a single daily dose or multiple doses.

The present disclosure also includes treating hypoparathyroid disorders in mammals, including humans, by administering an anti-hypoparathyroid-effective and/or PTHR agonist-effective amount of one or more the PTH analogs described herein. In particular, the compositions of the present invention may be used to treat hypoparathyroid conditions of any and all description.

It should be noted that the above-described pharmaceutical and nutritional compositions may be utilized in connection with non-human animals, both domestic and non-domestic, as well as humans.

EXAMPLES

The following Examples are included to provide a more complete description of the invention disclosed and claimed herein. The Examples are not intended to limit the scope of the claims in any fashion.

Peptide Synthesis and Purification:

Peptides were synthesized as C-terminal amides on NovaPEG rink amide resin (EMD-Millipore, Billerica, Mass.) using previously reported microwave-assisted solid-phase conditions based on Fmoc protection of main chain amino groups.[31] Briefly, protected amino acids were activated with 2-(1H-benzotriazole-1-yl)-1,1,3,3-tetramethyluronium hexafluorophosphate (HBTU) and N-hydroxybenzotriazole (HOBt) in the presence of N,N-diisopropylethylamine (DIEA). The growing peptide chain was deprotected using 20% piperidine in DMF. Protected $\beta^3$-homoamino acids were purchased from PepTech Corporation (Bedford, Mass.).

After synthesis, the peptides were cleaved from the resin and side chains were deprotected using reagent K (82.5% TFA, 5% phenol, 5% H$_2$O, 5% thioanisole, 2.5% ethanedithiol)[31] for two hours. The TFA solution was dripped into cold diethyl ether to precipitate the deprotected peptide. Peptides were purified on a prep-C18 column using reverse phase-HPLC. Purity was assessed by analytical RP-HPLC (solvent A: 0.1% TFA in water, solvent B: 0.1% TFA in acetonitrile, C18 analytical column (4.6×250 mm), flow rate 1 mL/min, gradient 10-60% B solvent over 50 minutes). Masses were measured by MALDI-TOF-MS. See Table 3. See also FIG. 2 for sequences.

TABLE 3

Retention time, purity and observed mass of α/β-peptides PTH analogs. Purities were estimated by quantifying the relative area under the curve of the peak corresponding to the desired product in the analytical RP-HPLC chromatograms.

| Analog Name | Retention Time (min) | Purity | $[m + H]_{calc(monoisotopic)}$ | $[m + H]_{obs(mono)}$ |
|---|---|---|---|---|
| A3 | 33.9 | 98.7% | 4157.2 | 4157.6 |
| A5 | 34.4 | 98.6% | 4185.2 | 4185.4 |
| B3 | 30.1 | 92.0% | 4149 | 4149.1 |
| B5 | 30.9 | >99% | 4176.9 | 4176.7 |
| C3 | 31.2 | 95.4% | 4157.2 | 4158.4 |
| C5 | 31.6 | 97.8% | 4185.2 | 4186.5 |
| D3 | 29.1 | >99% | 4157.2 | 4158.3 |
| D5 | 32.8 | >99% | 4185.2 | 4186.5 |
| D6 | 37.6 | >99% | 4248.3 | 4247.4 |
| D7 | 39.6 | >99% | 4262.3 | 4261.4 |

Figure 5A:
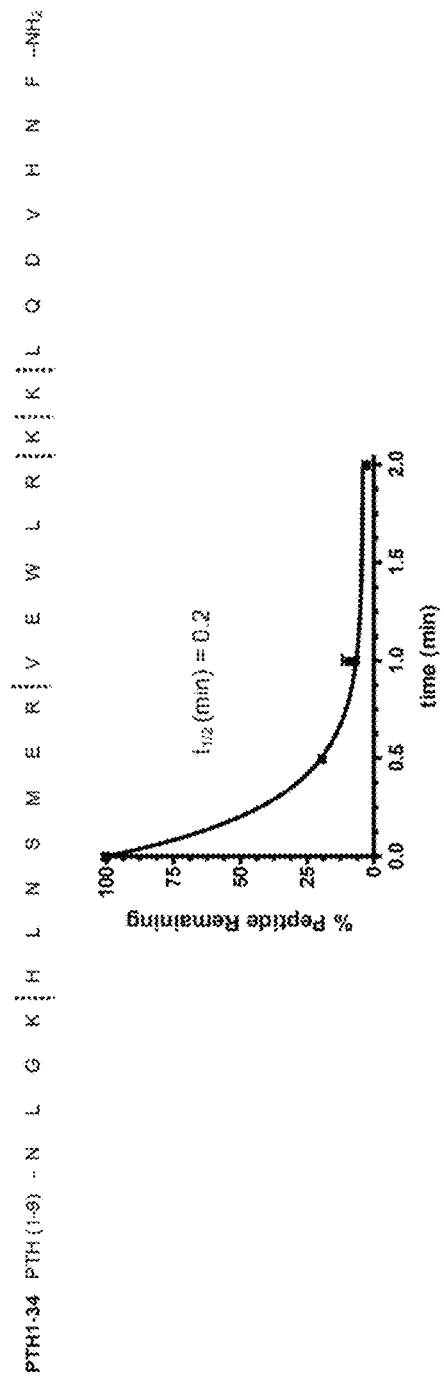
FIGS. 5A, 5B, and 5C are graphs depicting the proteolysis of PTH(1-34) (FIG. 5A), B5 (FIG. 5B), and D6 (FIG. 5C). Locations of β³ residues in B5 and D6 are indicated by highlighted residues. Solutions of 40 μM peptide in TBS were incubated at room temperature with 5 μg/mL trypsin. Vertical lines indicate observation by MALDI-MS of one or both products consistent with hydrolysis of the backbone amide bond between the noted residues. Each corresponding graph shows time-dependent degradation data with curves resulting from fitting of the data to an exponential decay model. Each data point represents the average of measurements from duplicate experiments, with error bars corresponding to the standard deviation.
Figure 5B:
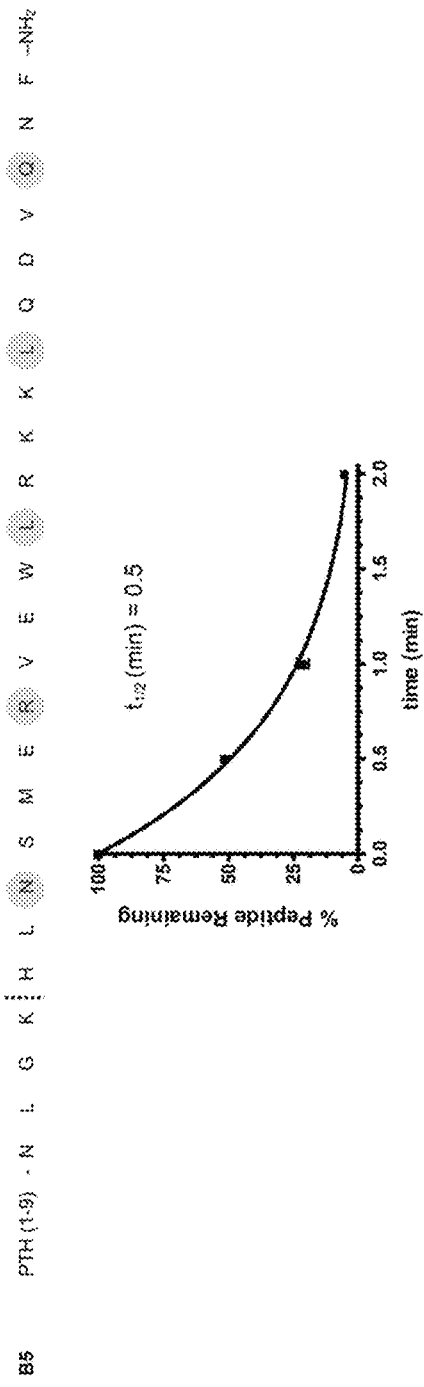
Figure 5C:
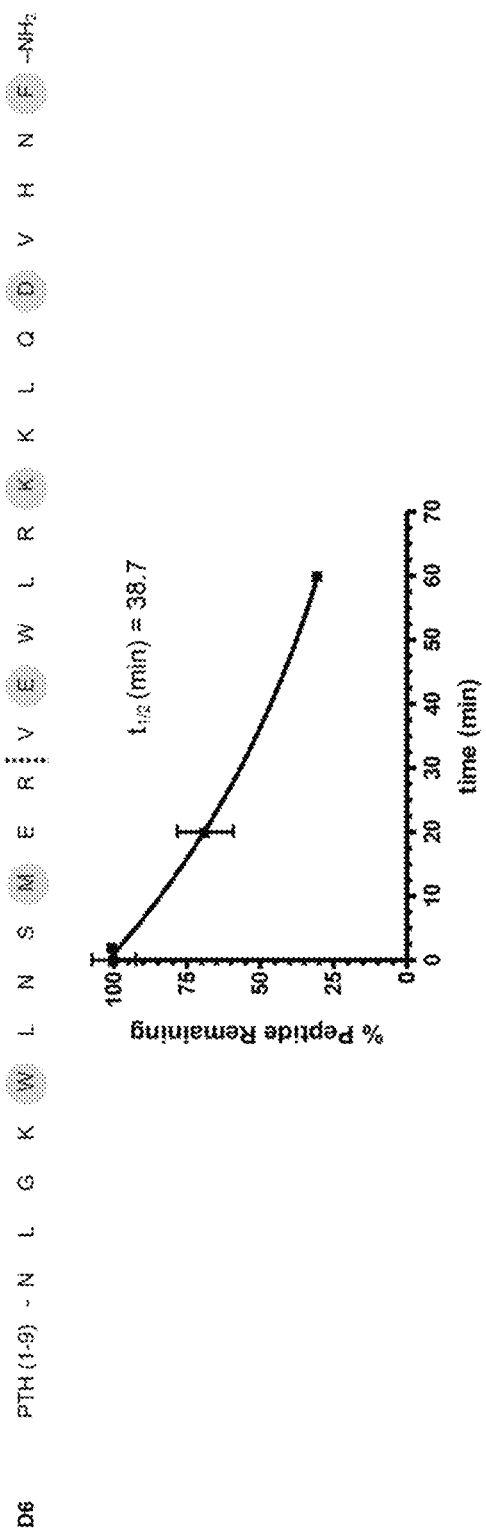
Figures 6A, 6B, 6C, 6D, 6E, 6F:
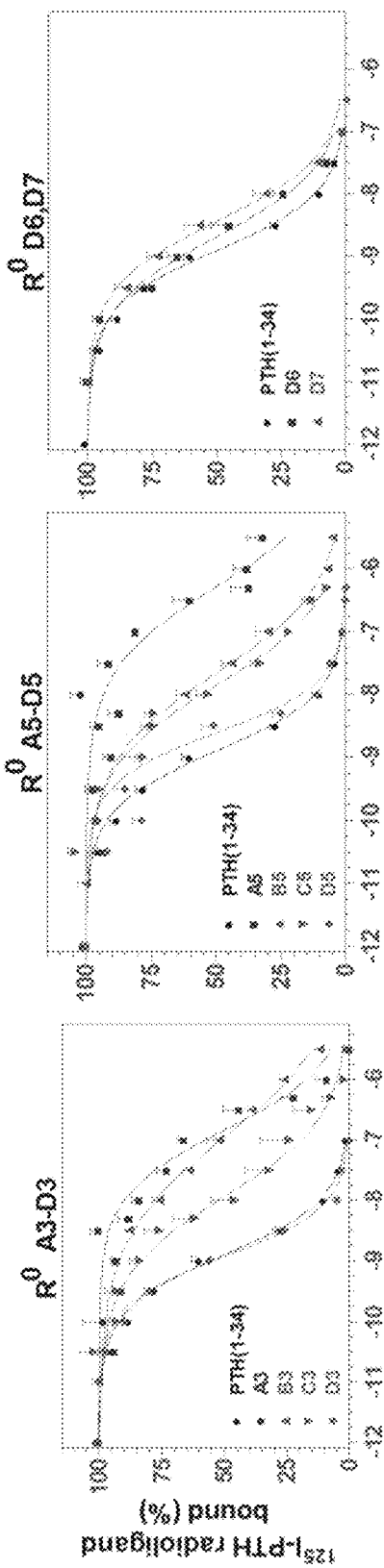
FIGS. 6A, 6B, 6C, 6D, 6E, and 6F constitute a series of graphs depicting binding of various analogs to the $R^O$ and RG forms of human PTHR-1 (hPTHR-1).

Protease Stability:

An HPLC assay was used to assess proteolytic stability.[30, 32] Peptide concentration was determined by UV-Vis spectroscopy (calculated from the UV-vis absorption at 280 nm, $\varepsilon_{280\ nm}$=5,690 M$^{-1}$ cm$^{-1}$ for all peptides except D6 and D7, $\varepsilon_{280\ nm}$=11,380 M$^{-1}$ cm$^{-1}$ based on an extinction coefficient for the tryptophan sidechain chromophore of 5,690 M$^{-1}$ cm$^{-1}$).[33] Peptide stock solutions were prepared in degassed water to a concentration of 200 μM. Sequencing-grade trypsin from bovine pancreas was purchased from Sigma Aldrich (St. Louis, Mo.) and prepared to a stock concentration of 100 μg/mL in 1 mM HCl. The protease reaction was carried out in 0.6 mL Eppendorf tubes at room temperature. The reaction solution was prepared by combining 40 μL of 200 μM peptide (final concentration 40 μM), 20 μL of 10×TBS pH 8.5 (final concentration 15 mM Tris, 150 mM NaCl, or 1×TBS), 130 μL of water, and 10 μL of 100 μg/mL protease (added last, final concentration 5 μg/mL, in a total volume of 200 μL). Each proteolysis experiment was run in duplicate. Following addition of protease, the reaction was timed and quenched by combining a 50 μL aliquot of the proteolysis mixture with 50 μL of 0.1% trifluoroacetic acid in acetonitrile. A portion (75 μL) of the quenched reaction mixture was injected onto an analytical RP-HPLC (see peptide synthesis and purification section above), and peaks were analyzed. The time course of peptide degradation was experimentally determined by integrating the area of the peak corresponding to the non-hydrolyzed peptide in a series of HPLC traces, with duplicate proteolysis reactions being used to generate error bars corresponding to the standard deviation. The final 50 μL of the reaction solution was used to acquire MALDI-TOF mass spectrometry data for identification of peptide fragments resulting from proteolysis. Proteolysis was observed at all predicted trypsin cut sites for PTH(1-34). Shown in FIGS. 5A, 5B, and 5C are time course data for peptide degradation. Exponential decay curves and half-life values were generated using GraphPad Prism version 5.0 (GraphPad Software, La Jolla, Calif.). FIGS. 5A, 5B, and 5C also show the trypsin cleavage sites in each substrate (based on MALDI-TOF-MS data).

Binding and cAMP Dose Response:

Reported IC$_{50}$ and EC$_{50}$ values are the average of ≥4 independent measurements. Each assay comprises ≥7 data points (different concentrations) per α/β-peptide, with each data point representing the average from duplicate wells. Binding to the RG and R$^0$ conformations of the human or rat PTHR-1 was assessed by competition assays performed in 96-well plates by using membranes from transiently transfected COS-7 cells as previously described.[6,7] In brief, binding to R$^0$ was assessed by using $^{125}$I-PTH(1-34) as tracer radio-ligand and including GTPγS in the reaction (1×10$^{-5}$ M). Binding to RG was assessed by using membranes containing a high-affinity, negative-dominant G$_\alpha$S subunit (G$_\alpha$S ND)[15], and $^{125}$I-M-PTH(1-15)[6] as tracer radio-ligand.

cAMP signaling was assessed using HEK-293-derived cell lines that stably express the GloSensor™-brand cAMP reporter (Promega Corp.) along with either the WT human PTHR-1 (GP-2.3 cells) or WT rat PTHR-1 (GR-35 cells). For cAMP dose-response assays, monolayers of confluent HEK 293 cells were pre-incubated with buffer containing d-luciferin (0.5 mM) in 96 well plates at room temperature until a stable baseline level of luminescence was established (30 min). Varying concentrations of agonist were then added, and the time course of luminescence response was recorded using a Perkin Elmer plate reader following α/β-peptide addition. The maximal luminescence response (observed 12-16 min after ligand addition) was used for generating dose response curves. Complete assay results (including EC$_{50}$/IC$_{50}$, standard error of the mean, E$_{max}$, and P values) for R$^0$ and RG binding and cAMP response assays for human and rat PTHR-1 can be found in Tables 4-7. Composite binding curves for R$^0$ and RG binding assays and cAMP response assays for human and rat PTHR-1 can be found in FIGS. 6A-6F, 7A-7F, 8A-8C, and 9A-9C.

TABLE 4

Binding to $R^0$ and RG forms of the human PTHR-1[a] with experimental uncertainty.

|  | $R^{0b}$ | | | $RG^c$ | | | |
| --- | --- | --- | --- | --- | --- | --- | --- |
|  |  | P | n |  | P | n | $R^0/RG$ |
| PTH(1-34) | 8.95 ± 0.09<br>1.1 nM | 1.00 | 9 | 9.99 ± 0.08<br>0.10 nM | 1.00 | 9 | 11 |
| A3 | 6.88 ± 0.14<br>133 nM | 0.00002 | 4 | 9.44 ± 0.18<br>0.36 nM | 0.048 | 4 | 366 |
| B3 | 7.10 ± 0.15<br>80 nM | 0.0001 | 5 | 9.90 ± 0.13<br>0.13 nM | 0.85 | 5 | 631 |
| C3 | 7.95 ± 0.39<br>11 nM | 0.048 | 4 | 9.37 ± 0.26<br>0.42 nM | 0.08 | 4 | 27 |
| D3 | 8.94 ± 0.11<br>1.1 nM | 0.29 | 5 | 9.98 ± 0.08<br>0.11 nM | 0.59 | 5 | 11 |
| A5 | 6.51 ± 0.16<br>310 nM | 0.00002 | 4 | 8.57 ± 0.26<br>2.7 nM | 0.004 | 4 | 114 |
| B5 | 7.72 ± 0.14<br>19 nM | 0.0006 | 5 | 10.07 ± 0.07<br>0.086 nM | 0.15 | 5 | 225 |
| C5 | 7.94 ± 0.12<br>11 nM | 0.0005 | 4 | 9.40 ± 0.20<br>0.40 nM | 0.047 | 4 | 29 |
| D5 | 8.77 ± 0.06<br>1.7 nM | 0.047 | 4 | 9.55 ± 0.21<br>0.28 nM | 0.11 | 4 | 6 |
| D6 | 8.69 ± 0.18<br>2.0 nM | 0.63 | 5 | 10.19 ± 0.24<br>0.065 nM | 0.34 | 5 | 31 |
| D7 | 8.45 ± 0.17<br>3.5 nM | 0.12 | 5 | 9.63 ± 0.06<br>0.24 nM | 0.0048 | 5 | 15 |

Binding inhibition constants are expressed as the -log ($IC_{50}$) and corresponding nanoMolar (nM) values.
Values are means (±SEM) of the number of experiments shown (n), each performed in duplicate.
P vs. PTH(1-34)
[a]Assays were performed in membranes prepared from COS-7 cells transiently transfected to express the rat PTHR1.
[b]$R^0$ assays used $^{125}$I-PTH(1-34) tracer and contained GTPγS (1 × $10^{-5}$ M).
[c]RG assays used $^{125}$I-M-PTH(1-15) tracer and membranes from cells co-transfected to express a high affinity Gαs mutant.

TABLE 5

Binding to $R^0$ and RG forms of the rat PTHR-1 with experimental uncertainty.

|  | $R^{0b}$ | | | $RG^c$ | | | |
| --- | --- | --- | --- | --- | --- | --- | --- |
|  |  | P | n |  | P | n | $R^0/RG$ |
| PTH(1-34) | 9.07 ± 0.13<br>0.8 nM | 1.00 | 4 | 9.38 ± 0.11<br>0.42 nM | 1.00 | 5 | 2 |
| A3 | 7.06 ± 0.25<br>88 nM | 0.00130 | 4 | 8.14 ± 0.06<br>7.2 nM | 0.00004 | 5 | 12 |
| B3 | 6.95 ± 0.22<br>111 nM | 0.0004 | 4 | 8.07 ± 0.06<br>8.6 nM | 0.00002 | 5 | 13 |
| C3 | 8.34 ± 0.07<br>5 nM | 0.006 | 4 | 8.40 ± 0.02<br>4.0 nM | 0.001 | 5 | 1 |
| D3 | 8.86 ± 0.18<br>1.4 nM | 0.39 | 4 | 9.55 ± 0.07<br>0.28 nM | 0.22 | 5 | 5 |
| A5 | 6.71 ± 0.21<br>197 nM | 0.00017 | 4 | 7.06 ± 0.05<br>86 nM | 0.000001 | 5 | 2 |
| B5 | 7.18 ± 0.10<br>65 nM | 0.0000 | 4 | 8.37 ± 0.16<br>4.2 nM | 0.001 | 5 | 15 |
| C5 | 7.76 ± 0.15<br>17 nM | 0.0007 | 4 | 9.09 ± 0.06<br>0.82 nM | 0.050 | 5 | 21 |
| D5 | 8.88 ± 0.10<br>1.3 nM | 0.294 | 4 | 8.76 ± 0.09<br>1.7 nM | 0.002 | 5 | 1 |
| D6 | 8.22 ± 0.14<br>6.1 nM | 0.00 | 4 | 9.09 ± 0.08<br>0.81 nM | 0.06 | 5 | 8 |
| D7 | 7.83 ± 0.12<br>14.8 nM | 0.00 | 4 | 8.69 ± 0.07<br>2.0 nM | 0.0010 | 5 | 7 |

Binding inhibition constants are expressed as the -log (IC50) and corresponding nanoMolar (nM) values.
Values are means (±SEM) of the number of experiments shown (n), each performed in duplicate.
P vs. PTH(1-34)
[a]Assays were performed in membranes prepared from COS-7 cells transiently transfected to express the rat PTHR1.
[b]R0 assays used 125I-PTH(1-34) tracer and contained GTPγS (1 × $10^{-5}$ M)
[c]RG assays used 125I-M-PTH(1-15) tracer and membranes from cells co-transfected to express a high affinity Gαs mutant.

TABLE 6 cAMP-stimulating activity in cells expressing the human PTHR-1[a] with experimental uncertainty.

| | Max[b] | | pEC$_{50}$ EC$_{50}$, nM | | | Fold nM |
|---|---|---|---|---|---|---|
| | | P[c] | | P | n | PTH(1-34) |
| PTH(1-34) | 217 ± 20 | 1.00 | 9.77 ± 0.04 0.17 nM | 1.00 | 9 | 1.00 |
| A3 | 232 ± 15 | 0.26 | 9.54 ± 0.11 0.29 nM | 0.16 | 4 | 1.66 |
| B3 | 234 ± 16 | 0.24 | 9.94 ± 0.04 0.11 nM | 0.029 | 4 | 0.67 |
| C3 | 223 ± 14 | 0.44 | 9.23 ± 0.10 0.58 nM | 0.0091 | 4 | 3.41 |
| D3 | 226 ± 15 | 0.37 | 9.79 ± 0.14 0.16 nM | 0.76 | 4 | 0.94 |
| A5 | 244 ± 32 | 0.70 | 8.78 ± 0.07 1.66 nM | 0.00 | 5 | 9.70 |
| B5 | 212 ± 30 | 0.80 | 9.97 ± 0.09 0.11 nM | 0.129 | 5 | 0.63 |
| C5 | 219 ± 39 | 0.93 | 9.70 ± 0.10 0.20 nM | 0.5448 | 5 | 1.15 |
| D5 | 223 ± 36 | 0.97 | 9.58 ± 0.10 0.26 nM | 0.15 | 5 | 1.52 |
| D6 | 189 ± 29 | 0.47 | 9.89 ± 0.08 0.13 nM | 0.34 | 5 | 0.76 |
| D7 | 184 ± 18 | 0.36 | 9.41 ± 0.13 0.39 nM | 0.042 | 5 | 2.26 |

Data are means (±SEM) of the number of experiments shown (n), each performed in duplicate.
[a]Assays were performed in GP-2.3 cells expressing the human PTHR1-WT and the luiferase-based, glosensor cAMP reporter.
[b]values are luminescence counts per second × 10$^{-3}$ observed at 12-16 minutes after ligand addition; basal values were 1.7 ± 0.2 cps × 10$^{-3}$.
[c]P vs PTH(1-34)

TABLE 7 cAMP-stimulating activity in cells expressing the rat PTHR-1[a] with experimental uncertainty.

| | Max[b] | | pEC50 EC50, nM | | | Fold nM |
|---|---|---|---|---|---|---|
| | | Pc | | P | n | PTH(1-34) |
| PTH(1-34) | 65 ± 31 | 1.00 | 9.38 ± 0.13 0.42 nM | 1.00 | 9 | 1.00 |
| A3 | 74 ± 101 | 0.14 | 8.79 ± 0.11 1.62 nM | 0.04 | 6 | 3.90 |
| B3 | 69 ± 78 | 0.16 | 9.26 ± 0.04 0.55 nM | 0.488 | 6 | 1.31 |
| C3 | 68 ± 77 | 0.20 | 9.00 ± 0.12 1.01 nM | 0.3063 | 6 | 2.43 |
| D3 | 65 ± 62 | 0.22 | 9.49 ± 0.04 0.32 nM | 0.03 | 6 | 0.77 |
| A5 | 54 ± 26 | 0.43 | 7.09 ± 0.13 81.60 nM | 0.00 | 6 | 195.88 |
| B5 | 51 ± 21 | 0.64 | 8.84 ± 0.05 1.45 nM | 0.028 | 6 | 3.49 |
| C5 | 48 ± 17 | 0.88 | 9.37 ± 0.08 0.42 nM | 0.1781 | 6 | 1.02 |
| D5 | 43 ± 17 | 0.66 | 9.29 ± 0.30 0.51 nM | 0.73 | 6 | 1.23 |
| D6 | 50 ± 15 | 0.72 | 9.48 ± 0.13 0.33 nM | 0.10 | 6 | 0.79 |
| D7 | 40 ± 18 | 0.43 | 8.79 ± 0.09 1.62 nM | 0.022 | 6 | 3.89 |

Data are means (±SEM) of the number of experiments shown (n), each performed in duplicate.
[a]Assays were performed in GR-35 cells expressing the rat PTHR1-WT and the luiferase-based, glosensor cAMP reporter.
[b]values are luminescence counts per second × 10-3 observed at 12-16 minutes after ligand addition; basal values were 0.47 ± 0.04 cps × 10-3.
cP vs PTH(1-34)

cAMP-Inducing Potency in Analogs Incorporating Beta-Amino Acid Residues into PTH at Various Positions:

A series of unnatural PTH(1-34) analogs were made in which various beta-amino acid residues were introduced at positions 1-9 of PTH(1-34). The cAMP-inducing potencies of the resulting N-terminally modified polypeptides is presented in Table 8.

TABLE 8 cAMP-Inducing Potencies: N-Terminal Modifications

| Peptide | hPTHR1 EC$_{50}$, nM (Means ± SEM) | Fold PTH, nM | deINT PTHR1 EC$_{50}$, nM (Means ± SEM) | Fold PTH, nM |
|---|---|---|---|---|
| PTH(1-34) | 0.09 ± 0.10 | 1.0 | 62 ± 37 | 1 |
| β$^3$Ala(1) | 0.20 ± 0.09 | 2.2 | 25 ± 1 | 0.4 |
| β$^3$Ser(1) | 0.06 ± 0.08 | 0.7 | 10 ± 6 | 0.2 |
| ACPC(1) | 0.15 ± 0.15 | 1.6 | 500 ± 290 | 8 |
| β$^3$Val(2) | 0.29 ± 0.18 | 3.2 | 5,200 ± 3,000 | 84 |
| ACPC(2) | 0.27 ± 1.34 | 3.0 | 11,000 ± 6,200 | 170 |
| β$^3$Ser(3) | 4.98 ± 0.03 | 54.6 | 340,000 ± 200,000 | 5,500 |
| ACPC(3) | 11.51 ± 0.11 | 126.1 | 7,800 ± 4,500 | 130 |
| β$^3$Glu(4) | 9.84 ± 0.04 | 107.9 | 15,000 ± 8,800 | 250 |
| ACPC(4) | No activity | N/A | 32,000 ± 18,000 | 510 |
| β$^3$Ile(5) | 2.59 ± 0.05 | 28.4 | No activity | N/a |
| ACPC(5) | 0.17 ± 0.08 | 1.9 | 4,100 ± 2,300 | 65 |
| β$^3$Gln(6) | 14.57 ± 0.04 | 159.7 | 6,700 ± 3,900 | 110 |
| ACPC(6) | 0.34 ± 0.05 | 3.7 | 22,000 ± 13,000 | 360 |
| β$^3$Leu(7) | 1.12 ± 0.05 | 12.3 | 67,000 ± 39,000 | 1,100 |
| ACPC(7) | 0.12 ± 0.05 | 1.3 | 4,600 ± 2,700 | 74 |
| β$^3$Met(8) | 18.69 ± 0.06 | 204.9 | 20,000 ± 12,000 | 330 |
| ACPC(8) | 9.74 ± 0.12 | 106.8 | 29,000 ± 17,000 | 480 |
| APC(9) | No activity | N/A | 5,400 ± 3,100 | 87 | n = 3 for each analog with each receptor type, except PTH (n = 6)

α-residue

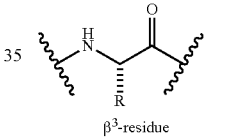

β$^3$-residue

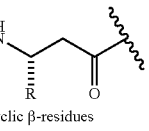

cyclic β-residues

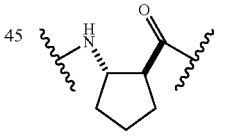

X
ACPC

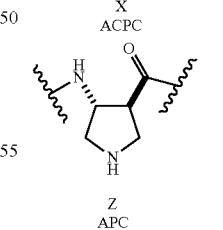

Z
APC

Further assays revealed that introducing selected β$^3$ residues at positions 1, 5, and 7 has no effect on, or only a small diminution of the bioactivity of the resulting compound in full-length hPTHR-1 and a truncated version lacking most (Ala$^{24}$-Arg$^{181}$) of the N domain ("delNT PTHR1"; see Barbier, J. R., Gardella, T. J., Dean, T., MacLean, S., Potetinova, Z., Whitfield, J. F., and Willick, G. E. (2005) *J. Biol. Chem.* 280, 23771-23777). For example, substitution at position 1 with any of $\beta^3$-Ala, $\beta^3$-Ser, and ACPC had zero effect on bioactivity. These modifications were completely tolerated in both hPTHR-1 and delNT PTHR-1. Modifications at position 2 ($\beta^3$-Val or ACPC) had no effect on cAMP potency in hPTHR-1, but did cause slight diminution in potency in delNT PTHR-1. Modifications at positions 5-7 ($\beta^3$-Ile(5), ACPC(5), $\beta^3$-Gln(6), ACPC(6), $\beta^3$-Leu(7) and ACPC(7)) revealed that cyclic $\beta$ residues were tolerated better than $\beta^3$ residues. With the exception of the $\beta^3$-Ile(5) and $\beta^3$-Leu(7) modifications in delNT PTHR-1, these changes caused no diminution or only slight diminution in cAMP-inducing potencies. The $\beta^3$-Ile(5) and $\beta^3$-Leu(7) modifications in delNT PTHR-1 resulted in weak or no potency in the modified, truncated receptor. Modifications at positions 3, 4, 8, and 9 caused significant diminution in potency in both hPTHR-1 and delNT PTHR-1.

Based on these results, the tolerated N-terminal modifications were then combined with C-terminal modifications. The results reveal that cyclic beta residues can be incorporated into the C-terminal portion of PTH(1-34) using the same substitution patterns shown to be useful for $\beta^3$-residue substitutions. In these studies, it was shown that at least three beta-amino acid substitutions can be incorporated into the N-terminus with retention of bioactivity ($EC_{50}$<50 nM). See Table 9:

TABLE 9

Effect of N-Terminal Modifications and Cyclic Constraints on cAMP induction Potency

| Analog | EC50, nM | Fold PTH |
|---|---|---|
| PTH(1-34) | 0.08 ± 0.01 | 1.0 |
| ACPC(1,7) | 0.14 ± 0.03 | 1.7 |
| ACPC(1,5,7) | 2.99 ± 0.56 | 36.7 |
| D6 | 0.17 ± 0.05 | 2.1 |
| cycD6 | 0.10 ± 0.01 | 1.3 |
| FcycD6 | 0.26 ± 0.05 | 3.2 |
| D6_ACPC(1,7) | 1.84 ± 0.11 | 22.6 |
| CycD6_ACPC(1,7) | 0.59 ± 0.07 | 7.3 |
| FcycD6_ACPC(1,7) | 0.71 ± 0.04 | 8.7 |
| D6_ACPC(1,5,7) | 166.8 ± 6.3 | 2,045 |
| CycD6_ACPC(1,5,7) | 21.7 ± 0.9 | 266 |
| FcycD6_ACPC(1,5,7) | 19.1 ± 1.3 | 234 |

Key:

| | |
|---|---|
| PTH (1-34) | SVSEIQLMHNLGKHLNSMERVEWLRKKLQDVHNF-NH$_2$ (SEQ. ID. NO: 14) |
| ACPC (1,7) | XVSEIQXMHNLGKHLNSMERVEWLRKKLQDVHNF-NH$_2$ (SEQ. ID. NO: 15) |
| ACPC(1,5,7) | XVSEXQXMHNLGKHLNSMERVEWLRKKLQDVHNF-NH$_2$ (SEQ. ID. NO: 16) |
| D6 | SVSEIQLMHNLGKWLNSMERVEWLRKKLQDVHNF-NH$_2$ (SEQ. ID. NO: 17) |
| CycD6 | SVSEIQLMHNLGKXLNSXERVEWLRZKLQDVHNX-NH$_2$ (SEQ. ID. NO: 18) |
| FcycD6 | SVSEIQLMHNLGKXLNSXERVZWLRZKLQXVHNX-NH$_2$ (SEQ. ID. NO: 19) |
| D6_ACPC(1,7) | XVSEIQXMHNLGKWLNSMERVEWLRKKLQDVHNF-NH$_2$ (SEQ. ID. NO: 20) |
| CycD6_ACPC(1,7) | XVSEIQXMHNLGKXLNSXERVEWLRZKLQDVHNX-NH$_2$ (SEQ. ID. NO: 21) |
| FcycD6_ACPC(1,7) | XVSEIQXMHNLGKXLNSXERVZWLRZKLQXVHNX-NH$_2$ (SEQ. ID. NO: 22) |
| D6_ACPC(1,5,7) | XVSEXQXMHNLGKWLNSMERVEWLRKKLQDVHNF-NH$_2$ (SEQ. ID. NO: 23) |
| CycD6_ACPC(1,5,7) | XVSEXQXMHNLGKXLNSXERVEWLRZKLQDVHNX-NH$_2$ (SEQ. ID. NO: 24) |

TABLE 9-continued

Effect of N-Terminal Modifications and Cyclic Constraints on cAMP induction Potency FcycD6_ACPC(1,5,7)     XVSEXQXMHNLGKXLNSXERVZWLRZKLQXVHNX-NH$_2$
(SEQ. ID. NO: 25)

Bold, underlined residues designate β$^3$ residues having the side chain of the α residue indicated by the letter. "X" = ACPC. "Y" = APC.

Additionally, the alpha-to-beta residue replacements described above for PTH(1-34) were also applied to a related peptide, M-PTH(1-34), which is also capable of activating PTHR. These results, compiled in Table 10, show that cyclic beta residues ACPC and APC can be incorporated into the C-terminal and N-terminal poritions of M-PTH(1-34) with minimal losses in bioactivity. All of these analogs retained very good biological potencies (EC$_{50}$<2 nM). Additionally, one of these analogs, M-FcycD6_ACPC(1,5,7) shows good stability in simulated gastric fluid, indicating that it has utility and can be used as an orally available PTH analog.

TABLE 10

Effect of N-Terminal Modifications and Cyclic Constraints on M-PTH(1-34) cAMP induction Potency

| Analog | EC50, nM | Fold PTH |
| --- | --- | --- |
| M-PTH(1-34) | 0.34 ± 0.04 | 4.2 |
| M-ACPC(1,7) | 0.52 ± 0.19 | 6.3 |
| M-ACPC(1,5,7) | 0.40 ± 0.11 | 4.9 |
| M-D6 | 0.44 ± 0.10 | 5.4 |
| M-cycD6 | 0.33 ± 0.08 | 4.0 |
| M-FcycD6 | 0.51 ± 0.15 | 6.3 |
| M-D6_ACPC(1,7) | 0.83 ± 0.07 | 10.2 |
| M-FcycD6_ACPC(1,7) | 1.77 ± 0.23 | 21.8 |
| M-X1,5,7-D6 | 0.79 ± 0.25 | 9.7 |
| M-X1,5,7-CycD6 | 0.31 ± 0.05 | 3.8 |
| M-X1,5,7-FcycD6 | 0.78 ± 0.12 | 9.5 |

Key:

M-PTH(1-34)        AVAEIQLMHQ$^h$RAKWLNSMRRVEWLRKKLQDVHNF-NH$_2$
(SEQ. ID. NO: 26)

M-ACPC(1,7)        XVUEIQXMHQ$^h$RAKWLNSMRRVEWLRKKLQDVHNF-NH$_2$
(SEQ. ID. NO: 27)

M-ACPC(1,5,7)      XVUEXQXMHQ$^h$RAKWLNSMRRVEWLRKKLQDVHNF-NH$_2$
(SEQ. ID. NO: 28)

M-D6               AVAEIQXMHQ$^h$RAKWLNSMRRVEWLRKKLQDVHNF-NH$_2$
(SEQ. ID. NO: 29)

M-cycD6            AVAEIQXMHQ$^h$RAKXLNSXRRVEWLRZKLQDVHNX-NH$_2$
(SEQ. ID. NO: 30)

M-FcycD6           AVAEIQXMHQ$^h$RAKXLNSXRRVZWLRZKLQXVHNX-NH$_2$
(SEQ. ID. NO: 31)

M-D6_ACPC(1,7)     XVUEIQXMHQ$^h$RAKWLNSMRRVEWLRKKLQDVHNF-NH$_2$
(SEQ. ID. NO: 32)

X M-cycD6_ACPC(1,7) XVUEIQXMHQ$^h$RAKXLNSXRRVEWLRZKLQDVHNX-NH$_2$
(SEQ. ID. NO: 33)

TABLE 10-continued

Effect of N-Terminal Modifications and Cyclic Constraints
on M-PTH(1-34) cAMP induction Potency

| | |
|---|---|
| M-FcycD6_ACPC(1,7) | XVUEIQXMHQ[h]RAKXLNSXRRVZWLRZKLQXVHNX-NH$_2$ (SEQ. ID. NO: 34) |
| M-X1,5,7-D6 | XVUEXQXMHQ[h]RAKWLNSMRRVEWLRKKLQDVHNF.-NH$_2$ (SEQ. ID. NO: 35) |
| M-X1,5,7-CycD6 | HXVUEXQXMHQ[h]RAKXLNSXRRVEWLRZKLQDVHNX-NH$_2$ (SEQ. ID. NO: 36) |
| M-X1,5,7-FcycD6 | XVUEXQXMHQ[h]RAKXLNSXRRVZWLRZKLQXVHNX--NH$_2$ (SEQ. ID. NO: 37) |

Bold, underlined residues designate β$^3$ residues having the side chain of the α residue indicated by the letter. "X" = ACPC. "Y" = APC. "U" = Aminoisobutyric Acid (Aib). [h]R = homoarginine (i.e., 2-amino-6-guanidinohexanoic acid).

All of the PTH analogs described in Table 10 and the M-PTH analogs described in Table 11 retained strong binding affinities for PTHR-1 (data not shown).

"Washout" Assays:

The duration of PTH analog stimulated cAMP response following removal of the solution containing dissolved peptide from the confluent HEK293 cell monolayers has been shown to be predictive of the duration of in vivo calcemic responses in mice.[8] This parameter of in vitro PTH analog performance shows strong positive correlation with R$^0$ binding affinity (high R$^0$ binding affinity correlates with prolonged cAMP signaling following washout). Washout assays were carried out for PTH(1-34), M-PTH(1-34)[8], and α/β-peptides B5 and D6 to assess the contribution of altered R$^0$ binding affinity to the duration of calcemic responses observed in vivo. M-PTH(1-34), a sidechain-altered PTH analog that has previously been shown to induce prolonged responses following washout and prolonged calcemic response in vivo with native-like bioavailability, was included as a control. HEK293 cell monolayers expressing rat PTHR-1 (GR35 cells) were treated with ligand in for 14 minutes. This buffer was then discarded, and the cell monolayer was rinsed (2×). Buffer containing luciferin was introduced for 120 minutes. Luminescence response was recorded before and after washout, with luminescence readings recorded every 2 minutes. The area under the curve (AUC) for luminescence response curve was determined using GraphPad Prism. See FIGS. 10A-10D for a graphs depicting the average of n=3 (M-PTH) or n=5 washout experiments. See Table 11 for a description of composite data from n=3 or 5 washout experiments.

In Vivo Pharmacology: Calcemic Response:

Mice (C57BL/6, male, age 9-12 weeks) were treated in accordance with the ethical guidelines adopted by Massachusetts General Hospital. Mice (n=5 per compound) were injected subcutaneously with vehicle (10 mM citric acid/150 mM NaCl/0.05% Tween-80, pH 5.0) or vehicle containing PTH(1-34) or α/β-peptide at a dose of 20 nmol/kg body weight. Blood was withdrawn just prior to injection (t=0) or at times thereafter. Tail vein blood was collected and immediately used for analysis. Blood Ca$^{2+}$ concentration was measured with a Chiron Diagnostics model 634 Ca$^{2+}$/pH analyzer.

Figure 13:
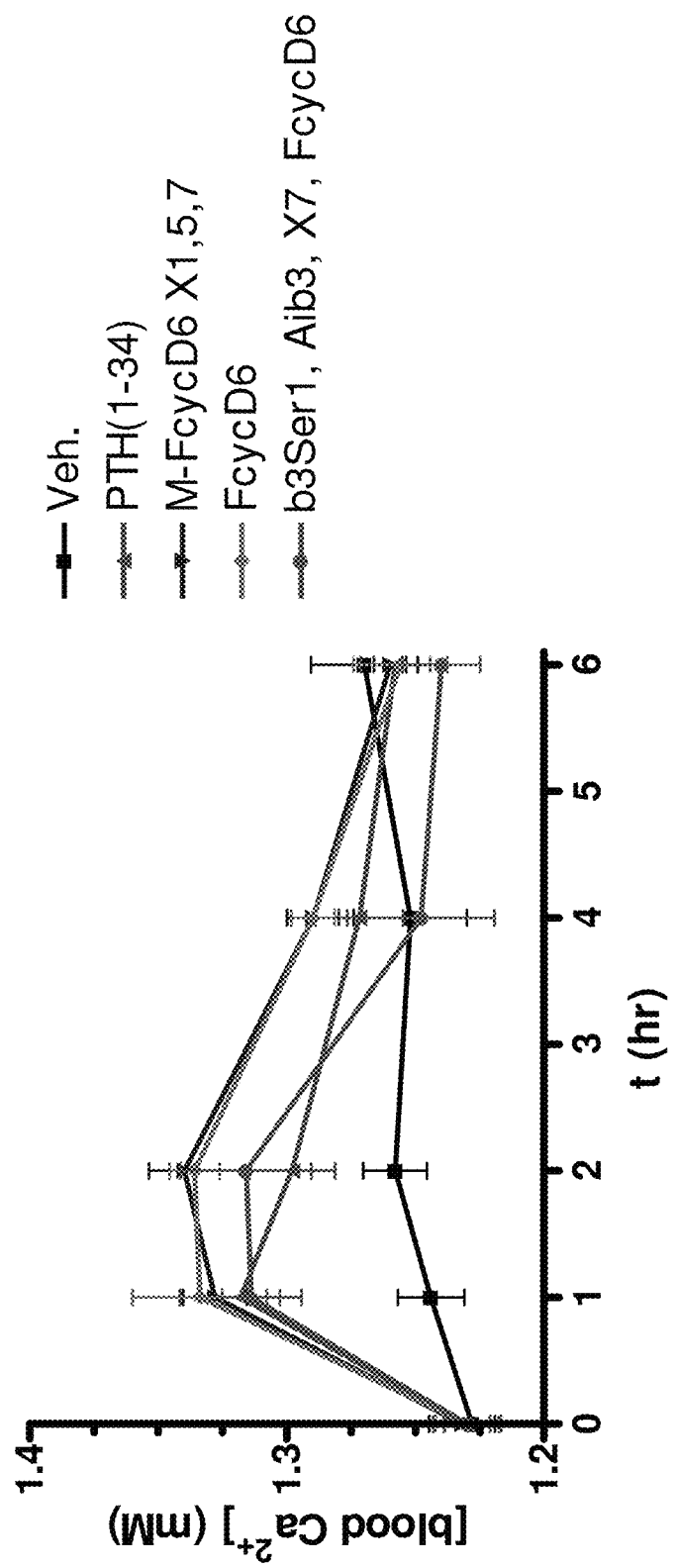
FIG. 13 is a graph depicting the calcemic response in mice following subcutaneous injection of various PTH analogs disclosed herein.

It was found that PTH(1-34) analogs containing cyclic beta-substitutions induce a calcemic response following subcutaneous injection into mice. See FIG. 13. M-FcycD6 X1,5,7 and FcycD6 both showed a very marked activity to increase calcium blood levels in mice.

Non M-PTH Analogs with Stability in Simulated Gastric Fluid:

The M-PTH analogs disclosed herein have prolonged signaling profiles. This is beneficial in some instances and undesirable in others. Highly modified analogs of PTH(1-34) have been synthesized that also have high stability in simulated gastric fluid. See Table 12:

TABLE 12

Non-M-PTH Analogs

| | |
|---|---|
| FcycD6_ACPC(1,5,7) | XVSEXQXMHNLGKXLNSXERVZWLRZKLQ XVHNX-NH$_2$ (SEQ. ID. NO: 25) |

TABLE 11

Statistics from rPTHR-1 washout experiments.

| | AUC-on[a] | AUC-washout[a] | AUC Ratio[b] | P vs PTH(1-34)[c] | n |
|---|---|---|---|---|---|
| PTH(1-34) | 92,000 ± 34,000 | 100,000 ± 25,000 | 1.31 ± 0.22 | 1.00 | 5 |
| M-PTH(1-34) | 43,000 ± 5,400 | 640,000 ± 65,000 | 14.8 ± 0.49 | 0.0002 | 3 |
| B5 | 130,000 ± 50,000 | 84,000 ± 23,000 | 0.80 ± 0.16 | 0.10 | 5 |
| D6 | 100,000 ± 36,000 | 130,000 ± 37,000 | 1.50 ± 0.35 | 0.67 | 5 |

Data are means (±SEM) of the number of experiments shown (n), each performed in duplicate.
[a]Area under the curve (AUC) is calculated using GraphPad Prism. AUC-on or AUC-washout refer to AUC values recorded in the 14 minutes before or the 120 minutes following washout, respectively
[b]AUC ratio refers to the ratio of AUC-washout to AUC-on
[c]Result of t-test of the AUC ratio of the indicated analog vs PTH(1-34) using a two-tailed t-test assuming unequal variance

TABLE 12-continued

Non-M-PTH Analogs

| | |
|---|---|
| FcycD6_β3Ser(1), ACPC(5,7) | SVSEXQXMHNLGKXLNSXERVZWLRZKLQ XVHNX-NH$_2$ (SEQ. ID. NO: 38) |
| FcycD6_β3Ser(1), Aib(3), ACPC (7) | SVUEIQXMHNLGKXLNSXERVZWLRZKLQ XVHNX-NH$_2$ (SEQ. ID. NO: 39) |

Bold, underlined residues designate β$^3$ residues having the side chain of the α residue indicated by the letter. "X" = ACPC. "Y" = APC. "U" = Aminoisobutyric Acid (Aib).

cAMP potency and binding affinities are presented in Table 13:

TABLE 13

| Analog (non M-PTH) | cAMP, EC$_{50}$ nM ± SEM | R$^0$ binding, IC$_{50}$ (GP2.3 memb.) nM ± SEM | RG binding, IC$_{50}$ nM ± SEM |
|---|---|---|---|
| PTH(1-34) | 0.08 ± 0.01 | 0.84 ± 0.45 | 0.43 ± 0.08 |
| FcycD6_ACPC(1, 5, 7) | 25.9 | | |
| FcycD6_β$^3$Ser1, ACPC(5, 7 | 0.79 | 89.38 ± 11.16 | |
| FcycD6_β$^3$Ser1, Aib3, ACPC7 | 0.21 | 1.54 ± 0.44 | |

Beta-amino acid substitutions tolerated in the C-terminal portion (at positions 14,18,22,26,30, and 34) and N-terminal portions (positions 1,5, and 7) of PTH(1-34) are also tolerated, to varying extents, in the N-terminal fragment human parathyroid related-protein (hPTHrP 1-34) and BA058. See Table 14:

TABLE 14 cAMP potencies, GP2.3 cells, BA058 analogs:

| Analog | cAMP EC50, nM | Stdev |
|---|---|---|
| hPTH(1-34) | 0.1 | 0.01 |
| BA058 | 0.03 | 0.02 |
| D6 BA058 | 4.13 | 0.27 |
| CycD6 BA058 | 0.18 | 0.01 |
| BA058 ACPC(1,7) | 4.69 | 0.21 |
| D6 BA058 ACPC(1,7) | 140.57 | 14.96 |
| CycD6 BA058 ACPC(1,7) | 18.88 | n.d. |
| BA058 ACPC(1,5,7) | 0.26 | 0.12 |
| D6 BA058 ACPC(1,5,7) | n.d. | |
| CycD6 BA058 ACPC(1,5,7) | 0.65 | 0.39 |

Key:

| | |
|---|---|
| BA058 | AVSEHQLLHDKGKSIQDLRRRELLEKLLUKLHTA-NH$_2$ (SEQ. ID. NO: 40) |
| D6 BA058 | AVSEHQLLHDKGKSIQDLRRRELLEKLLUKLHA-NH$_2$ (SEQ. ID. NO: 41) |
| cycD6 BA058 | AVSEHQLLHDKGKXIQDXRRRZLLEZLLUXLHTX-NH$_2$ (SEQ. ID. NO: 42) |
| BA058 ACPC(1,7) | XVSEHQXLHDKGKSIQDLRRRELLEKLLUKLHTA-NH$_2$ (SEQ. ID. NO: 43) |
| D6 BA058 ACPC(1,7) | XVSEHQXLHDKGKSIQDLRRRELLEKLLUKLHTX-NH$_2$ (SEQ. ID. NO: 44) |
| cycD6 BA058 ACPC(1,7) | XVSEHQXLHDKGKXIQDXRRRZLLEZLLUXLHTX-NH$_2$ (SEQ. ID. NO: 45) |
| BA058 ACPC (1,5,7) | XVSEXQXLHDKGKSIQDLRRRELLEKLLUKLHTA-NH$_2$ (SEQ. ID. NO: 46) |
| D6 BA058 ACPC (1,5,7) | XVSEXQXLHDKGKSIQDLRRRELLEKLLUKLHTX-NH$_2$ (SEQ. ID. NO: 47) |
| cycD6 BA058 ACPC (1,5,7) | XVSEXQXLHDKGKXIQDXRRRZLLEZLLUXLHTX-NH$_2$ (SEQ. ID. NO: 48) |

Bold, underlined residues designate β$^3$ residues having the side chain of the α residue indicated by the letter. "X" = ACPC. "Y" = APC. "U" = Aminoisobutyric Acid (Aib). n.d. = not determined.

Beta-amino acid substitutions tolerated in the C-terminal portion (at positions 14, 18, 22, 26, 30, and 34) and N-terminal portions (positions 1, 5, and 7) of PTH(1-34) are also tolerated, to varying extents, in the N-terminal fragment human parathyroid related-protein (hPTHrP 1-34) and BA058. See Table 15;

TABLE 15 cAMP potencies, GP2.3 cells, hPTHrP analogs:

| Analog | cAMP EC50, nM | Stdev |
|---|---|---|
| hPTH(1-34) | 0.1 | 0.01 |
| hPTHrP(1-34) | 0.10 | n.d. |
| D6 hPTHrP(1-34) | 0.32 | 0.15 |
| CycD6 hPTHrP(1-34) | 0.65 | 0.19 |
| D6 hPTHrP(1-34) ACPC(1,5,7) | 1.03 | 0.15 |
| CycD6 hPTHrP(1-34) ACPC(1,5,7) | 1.08 | 0.01 |

Key:

| | |
|---|---|
| hPTH(1-34) | SVSEIQLMHNLGKHLNSMERVEWLRKKLQDVHNF-NH$_2$ (SEQ. ID. NO: 49) |
| hPTHrP (1-34) | AVSEHQLLHDKGKSIQDLRRRFFLHHLIAEIHTA-NH$_2$ (SEQ. ID. NO: 50) |
| D6 hPTHrP(1-34) | AVSEHQLLHDKGKSIQDLRRRFFLHKLIAEIHTA-NH$_2$ (SEQ. ID. NO: 51) |
| CycD6 hPTHrP(1-34) | AVSEHQLLHDKGKXIQDXRRRZFLHZLIAXIHTX-NH$_2$ (SEQ. ID. NO: 52) |
| D6 hPTHrP(1-34) ACPC (1,5,7) | XVSEXQXLHDKGKSIQDLRRRFFLHKLIAEIHTA-NH$_2$ (SEQ. ID. NO: 53) |
| CycD6 hPTHrP(1-34) ACPC (1,5,7) | XVSEXQXLHDKGKXIQDXRRRZFLHZLIAXIHTX-NH$_2$ (SEQ. ID. NO: 54) |

Bold, underlined residues designate β$^3$ residues having the side chain of the α residue indicated by the letter. "X" = ACPC. "Y" = APC. "U" = Aminoisobutyric Acid (Aib). n.d. = not determined.

Beta-amino acid substitutions alter PTH(1-34) so that these analogs selectively signal using the parathyroid hormone receptor-1 or parathyroid hormone receptor-2. Natural PTH(1-34) is a potent agonist of both PTHR-1 and PTHR-2. Selected analogs containing beta-amino acid substitutions selectively signal through one or the other of the two receptors. Without being bound to any underling biological phenomenon or mechanism, PTHR-2 likely serves an alternative function to PTHR-1 as it is highly expressed in the central nervous system. In contrast, PTHR-1 is highly expressed in bone and kidney, but not in the CNS. The analogs disclosed herein are thus useful as therapeutic compounds that a specific agonists or antagonists of PTHR-1 and PTHR-2. See Tables 16 and 17:

TABLE 16

| cAMP response PTH2R/PTH1R (most selective) | |
|---|---|
| hTIP(1-39) | 165 |
| β3Gln(6) PTH(1-34) | 133 |
| FcycD6 ACPC(1,5,7) PTH(1-34) | 45 |
| ACPC(1, 5, 7) PTH(1-34) | 11 |
| hPTH(1-34) | 1.1 |
| hPTHrP(1-36) | 0.04 |

TABLE 17

| cAMP response PTH1R/PTH2R (most selective) | |
|---|---|
| ACPC(7) PTH(1-34) | 44 |
| B5 PTH(1-34) | 43 |

TABLE 17-continued

| cAMP response PTH1R/PTH2R (most selective) | |
|---|---|
| D6 PTH(1-34) | 33 |
| hPTHrP(1-36) | 27 |
| hPTH(1-34) | 0.9 |
| hTIP(1-39) | 0.01 |

The analogs are also useful as probes for for pinpointing differences in ligand recognition by PTH1R and PTH2R.

Additionally, beta-amino acid substitutions can be incorporated into bPTH(7-34) dTrp12 to provide stabilized analogs. These analogs serve as inhibitors of PTH-induced PTHR1 signaling and as inverse agonists of basal cAMP signaling in mutant PTH receptors that show high levels of constitutive activity. Inhibiting PTHR1 signaling is useful in treating hypercalcemia resulting from overproduction of PTH or PTHrP, which occurs in some cancers. Inverse agonism of constitutively-active receptor mutants is useful for treating patients expressing these mutant receptors. See Table 18:

TABLE 18

| [Inhibitor] = 1 μM | EC50, nM | EC50 $_{(+)\,inhibitor}$/EC50 $_{(-)\,inhibitor}$ |
|---|---|---|
| No inhibitor | 0.16 | 1.00 |
| hPTH(7-34) | 0.25 | 1.60 |
| bPTH(7-34)dTrp12 | 9.47 | 60.12 |
| D6 bPTH(7-34) dTrp12 | 2.60 | 16.49 |
| D6 bPTH(7-34) dTrp12 ACPC7 | 0.69 | 4.38 |
| FCycD6 bPTH(7-34) dTrp12 ACPC7 | 0.55 | 3.50 |

Key:

| | |
|---|---|
| PTH(7-34) | LMHNLGKHLNSMERVEWLRKKLQDVHNF-NH$_2$ (SEQ. ID. NO: 55) |
| bPTH(7-34) | FMHNLGKHLSSMERVEWLRKKLQDVHNF-NH$_2$ (SEQ. ID. NO: 56) |
| bPTH(7-34) dTrp12 | FMHNLWKHLSSMERVEWLRKKLQDVHNF-NH$_2$ (SEQ. ID. NO: 57) |
| D6 bPTH(7-34) dTrp12 | FMHNLWKWLSSMERVEWLRKKLQDVHNF-NH$_2$ (SEQ. ID. NO: 58) |
| D6 bPTH(7-34) dTrp12_X7 | XMHNLWKWLSSMERVEWLRKKLQDVHNF-NH$_2$ (SEQ. ID. NO: 59) |
| CycD6 bPTH(7-34) dTrp12_X7 | XMHNLWKXLSSXERVZWLRZKLQXVHNX-NH$_2$ (SEQ. ID. NO: 60) |

As shown in Table 18, α/β-bPTH(7-34) dTrp12 analogs act as inhibitors of PTH(1-34) signaling. These analogs also exhibit PTH1R binding comparable to corresponding α-peptides (data not shown).

Figure 14:
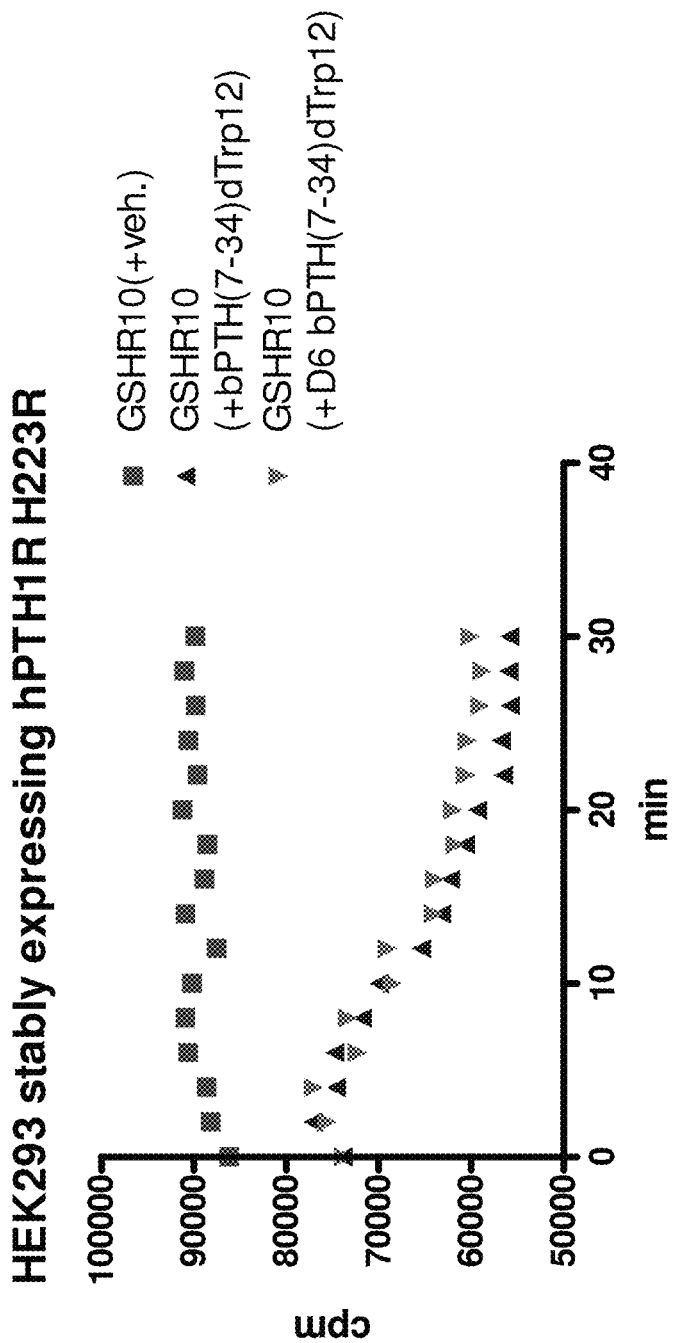
FIG. 14 is a graph depicting results of cells treated with 0.5 mM luciferin and 2 mM IBMX in $CO_2$ independent media for 30 minutes before treatment with bPTH(7-34) analogs added at 1 μM dose (at 0 min.).
Figure 15:
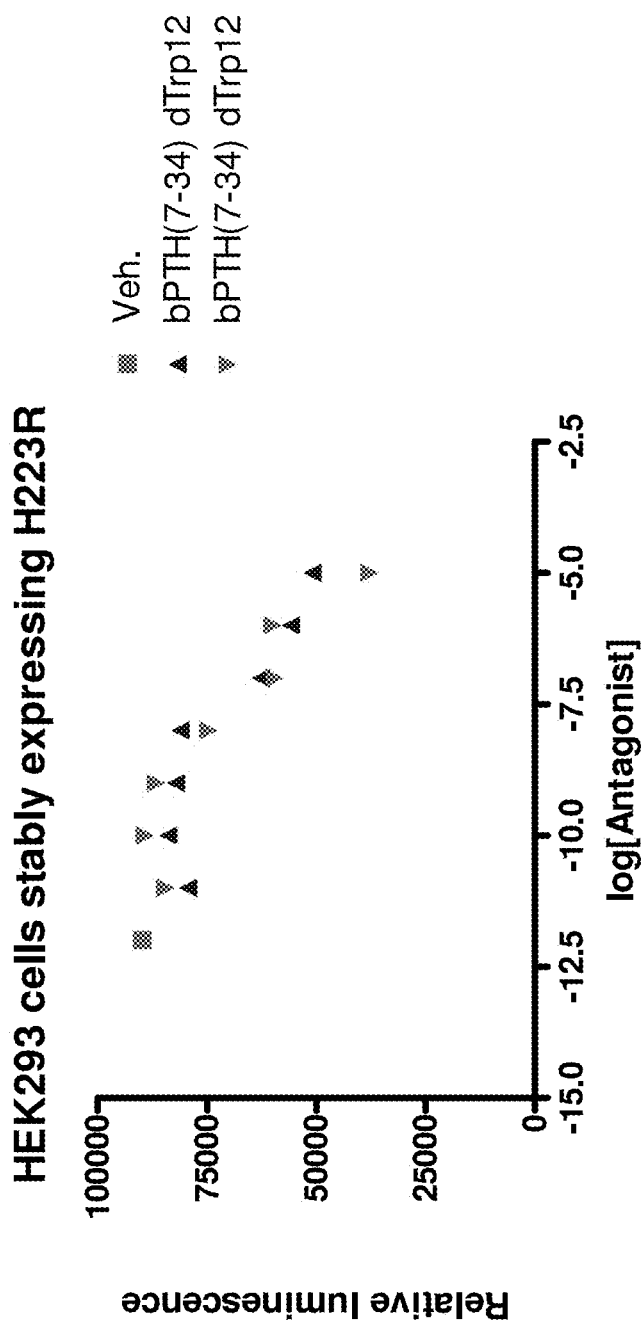
FIG. 15 is a graph depicting cells treated with 0.5 mM luciferin and 2 mM IBMX in $CO_2$ independent media for 30 minutes before treatment with bPTH(7-34) analogs. Luminescence response recorded 30 minutes after addition of inverse agonists (or vehicle).

The data presented in FIGS. 14 and 15 show that selected α/β-peptides disclosed herein do function as PTH1R inverse agonists. In both figures, HEK293 cells stably expressing hPTH1R H223R were treated with 0.5 mM luciferin and 2 mM IBMX in CO$_2$ independent media for 30 minutes before treatment with the noted bPTH(7-34) analogs added at 1 μM dose (at 0 min). In both figures, luminescence response was recorded 30 minutes after addition of the test compound (or vehicle). Both figures clearly show a time-dependent response when the test compounds were administered.

Figure 12A:
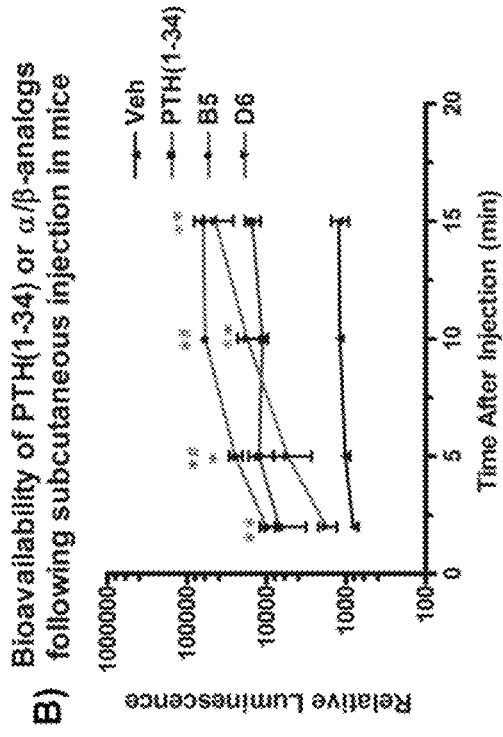
FIGS. 12A, 12B, and 12C constitute a series of graphs depicting raw luminescence traces and standard curves for assessing PTH(1-34) and α/β-peptide bioavailability.
Figure 12B:
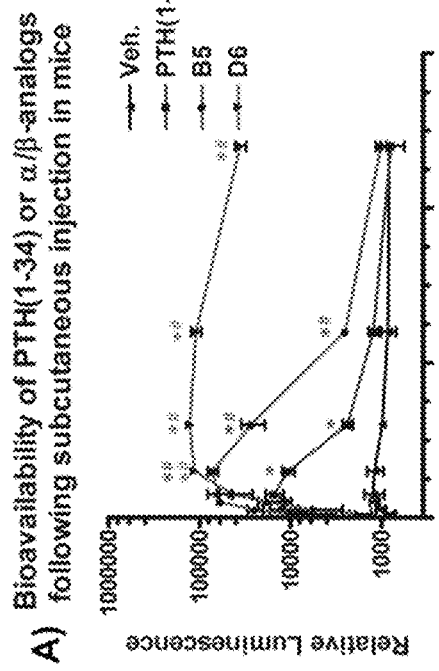
Figure 12C:
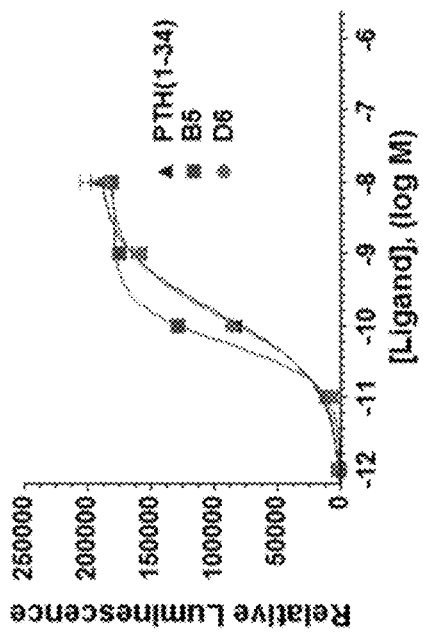

In Vivo Pharmacokinetics:

Blood content of PTH(1-34) or α/β-peptide analog was assessed in plasma from mice (n=3) injected with vehicle or vehicle containing PTH(1-34) or an α/β-peptide at a dose of 20 nmol/kg body weight in an experiment performed separately from the calcemic response assays described above. Blood was withdrawn just prior to injection (t=0) or at times thereafter. Tail vein blood was collected and treated with protease inhibitors (aprotinin, leupeptin, EDTA), centrifuged to remove blood cells, mixed with cAMP response assay buffer, and administered to GP2.3 cells. The raw luminescence readouts recorded in this assay were converted to blood peptide concentrations through use of a standard curve relating luminescence response to known peptide concentrations under identical assay conditions. See FIGS. 12A, 12B, and 12C. Previous work has demonstrated this cAMP response-based method for quantifying the blood concentrations of PTHR-1 agonists yields results similar to those from an ELISA-based method.[8] GP2.3 cells exposed to plasma from mice injected with vehicle showed negligible luminescence responses, indicating that observed cAMP responses were dependent on the presence of a PTHR-1 agonist.

Data Calculations:

Data were processed by using the Microsoft Excel and GraphPad Prism 4.0 software packages. Data from binding and cAMP dose-response assays were analyzed using a sigmoidal dose-response model with variable slope. Washout responses were assessed by quantifying the area under the luminescence response curve (AUC) following washout. Post-washout AUC was normalized by dividing the post-washout AUC by the pre-washout AUC. Paired data sets were statistically compared by using Student's t test (two-tailed) assuming unequal variances for the two sets.

REFERENCES CITED

The following documents are incorporated herein by reference.

1. Rajagopal, S., Rajagopal, K. & Lefkowitz, R. J. Teaching old receptors new tricks: biasing seven-transmembrane receptors. Nat. Rev. Drug Discovery 9, 373-386 (2010).
2. Kenakin, T. & Christopoulos, A. Signaling bias in new drug discovery: detection, quantification and therapeutic impact. Nat. Rev. Drug Discovery 12, 205 (2013).
3. Rajagopal, S. et al. Quantifying Ligand Bias at Seven-Transmembrane Receptors. Mol. Pharmacol. 80, 367-377 (2011).
4. Venkatakrishnan, A. J. et al. Molecular signatures of G-protein-coupled receptors. Nature 494, 185-194 (2013).
5. Hoare, S. R. J., Gardella, T. J. & Usdin, T. B. Evaluating the signal transduction mechanism of the parathyroid hormone 1 receptor—Effect of receptor-G-protein interaction on the ligand binding mechanism and receptor conformation. J. Biol. Chem. 276, 7741-7753 (2001).
6. Dean, T. et al. Mechanisms of ligand binding to the parathyroid hormone (PTH)/PTH-related protein receptor: Selectivity of a modified PTH(1-15) Radioligand for Gα$_s$-coupled receptor conformations. *Mol. Endocrinol.* 20, 931-943 (2006).
7. Dean, T., Vilardaga, J. P., Potts, J. T. & Gardella, T. J. Altered selectivity of parathyroid hormone (PTH) and PTH-Related protein (PTHrP) for distinct conformations of the PTH/PTHrP receptor. *Mol. Endocrinol.* 22, 156-166 (2008).
8. Okazaki, M. et al. Prolonged signaling at the parathyroid hormone receptor by peptide ligands targeted to a specific receptor conformation. *Proc. Natl. Acad. Sci. U.S.A.* 105, 16525-16530 (2008).
9. Vilardaga, J. P., Romero, G., Friedman, P. A. & Gardella, T. J. Molecular basis of parathyroid hormone receptor signaling and trafficking: a family B GPCR paradigm. *Cell. Mol. Life Sci.* 68, 1-13 (2011).
10. Feinstein, T. N. et al. Retromer terminates the generation of cAMP by internalized PTH receptors. *Nat. Chem. Biol.* 7, 278-284 (2011).
11. Neer, R. M. et al. Effect of parathyroid hormone (1-34) on fractures and bone mineral density in postmenopausal women with osteoporosis. *N. Engl. J. Med.* 344, 1434-1441 (2001).
12. Pioszak, A. A. & Xu, H. E. Molecular recognition of parathyroid hormone by its G protein-coupled receptor. *Proc. Natl. Acad. Sci. U.S.A.* 105, 5034-5039 (2008).
13. Boersma, M. D. et al. Evaluation of Diverse alpha/beta-Backbone Patterns for Functional α-Helix Mimicry: Analogs of the Bim BH3 Domain. *J. Am. Chem. Soc.* 134, 315-323 (2012).
14. Hoare, S. R. J., De Vries, G. & Usdin, T. B. Measurement of agonist and antagonist ligand-binding parameters at the human parathyroid hormone type 1 receptor: Evaluation of receptor states and modulation by guanine nucleotide. *J. Pharmacol. Exp. Ther.* 289, 1323-1333 (1999).
15. Berlot, C. H. A highly effective dominant negative α$_s$ construct containing mutations that affect distinct functions inhibits multiple G$_s$-coupled receptor signaling pathways. *J. Biol. Chem.* 277, 21080-21085 (2002).
16. Binkowski, B. F. et al. A Luminescent Biosensor with Increased Dynamic Range for Intracellular cAMP. *ACS Chem. Biol.* 6, 1193-1197 (2011).
17. Piserchio, A., Shimizu, N., Gardella, T. J. & Mierke, D. F. Residue 19 of the parathyroid hormone: Structural consequences. *Biochemistry* 41, 13217-13223 (2002).
18. Schievano, E. et al. Conformational and biological characterization of human parathyroid hormone hPTH(1-34) analogs containing beta-amino acid residues in positions 17-19. *Biopolymers* 70, 534-547 (2003).
19. Shimizu, M., Potts, J. T. & Gardella, T. J. Minimization of parathyroid hormone—Novel amino-terminal parathyroid hormone fragments with enhanced potency in activating the type-1 parathyroid hormone receptor. *J. Biol. Chem.* 275, 21836-21843 (2000).
20. Serada, M. et al. The role of the liver and kidneys in the pharmacokinetics of subcutaneously administered teriparatide acetate in rats. *Xenobiotica* 42, 398-407 (2012).
21. Maeda, A., et al. Critical role of parathyroid hormone (PTH) receptor-1 phosphorylation in regulating acute responses to PTH. *Proc. Natl. Acad. Sci. U.S.A.* 110, 5864-5869 (2013).
22. Lagerstrom, M. C. & Schioth, H. B. Structural diversity of G protein-coupled receptors and significance for drug discovery. *Nat. Rev. Drug Discovery* 7, 339-357 (2008).
23. Pal, K., Melcher, K. & Xu, H. E. Structure and mechanism for recognition of peptide hormones by Class B G-protein-coupled receptors. *Acta Pharmacol. Sin.* 33, 300-311 (2012).
24. Parthier, C., Reedtz-Runge, S., Rudolph, R. & Stubbs, M. T. Passing the baton in class B GPCRs: peptide hormone activation via helix induction? *Trends Biochem. Sci.* 34, 303-310 (2009).
25. Koth, C. M. et al. Molecular basis for negative regulation of the glucagon receptor. *Proc. Natl. Acad. Sci. U.S.A.* 109, 14393-14398 (2012).
26. Rasmussen, S. G. F. et al. Crystal structure of the β$_2$ adrenergic receptor-Gs protein complex. *Nature* 477, 549-U311 (2011).
27. Uzawa, T., Hori, M., Ejiri, S. & Ozawa, H. Comparison of the Effects of Intermittent and Continuous Administration of Human Parathyroid Hormone(1-34) on Rat Bone. *Bone* 16, 477-484 (1995).
28. Qin, L., Raggatt, L. J. & Partridge, N. C. Parathyroid hormone: a double-edged sword for bone metabolism. *Trends in Endocrinology and Metabolism* 15, 60-65 (2004).
29. Kostenuik, P. J. et al. Infrequent delivery of a long-acting PTH-Fc fusion protein has potent anabolic effects on cortical and cancellous bone. *Journal of Bone and Mineral Research* 22, 1534-1547 (2007).
30. Horne, W. S., Boersma, M. D., Windsor, M. A. & Gellman, S. H. Sequence-based design of α/β-peptide foldamers that mimic BH3 domains. *Angew. Chem. Int. Ed.* 47, 2853-2856 (2008).
31. King, D. S., Fields, C. G., and Fields, G. B. A cleavage method which minimizes side reactions following FMOC solid-phase peptide-synthesis, *International Journal of Peptide and Protein Research* 36, 255-266 (1990).
32. Horne, W. S. et al. Structural and biological mimicry of protein surface recognition by α/β-peptide foldamers. *Proc. Natl. Acad. Sci. U.S.A.* 106, 14751-14756 (2009).
33. Gill, S. C. & Vonhippel, P. H. Calculation of protein extinction coefficients from amino-acid sequence data. *Analytical Biochemistry* 182, 319-326 (1989)
34. Gardella, T. J., Wilson, A. K., Keutmann, H. T., Oberstein, R., Potts, J. T., Kronenberg, H. M., and Nussbaum, S. R. Analysis of Parathyroid Hormone's Principal Receptor-binding Region by Site-directed Mutagenesis and Analog, *Endocrinology* 132, 2024-2030 (1993).

What is claimed is:

1. An isolated, unnatural peptide analog comprising:

PTH, a parathyroid hormone receptor (PTHR-1, PTHR-2) agonist- or inverse agonist effective fragment of PTH, a parathyroid hormone related protein (PTHrP), a PTHR-1 or PTHR-2 agonist-, or inverse agonist-effective fragment of PTHrP, M-PTH, a PTHR-1 or PTHR-2 agonist- or inverse agonist-effective fragment of M-PTH, BA058, or a PTHR-1 or PTHR-2 agonist-, or inverse agonist-effective fragment of BA058, in which at least five non-adjacent α-amino acid residues are replaced with β-amino acid residues; and salts thereof.

2. The peptide analog of claim 1, in which the at least five α-amino acid residues are replaced with five β-amino acid residues having the same side-chain as the α-amino acid residues they replace.

3. The peptide analog of claim 1, in which at least one of the at least five non-adjacent α-amino acid residues is replaced with a cyclically constrained β-amino acid residue.

4. The peptide analog of claim 1, in which the at least five β-amino acid residues appear in a pattern comprising αβαβαβαβαβ, ααβααβααβααβααβ, αααβαααβααα-βαααβαααβ, and ααβαααβααβαααβααβ.

5. The peptide analog of claim 1, comprising thirty four (34) N-terminal residues of a mammalian parathyroid hormone, PTH(1-34), in which at least five non-adjacent α-amino acid residues are replaced with a β-amino acid residues.

6. The peptide analog of claim 5, in which the at least five α-amino acid residues are replaced with three β-amino acid residues having the same side-chain as the α-amino acid residues they replace.

7. The peptide analog of claim 5, in which at least one of the at least five non-adjacent α-amino acid residues is replaced with a cyclically constrained β-amino acid residue.

8. The peptide analog of claim 5, in which the at least three β-amino acid residues appear in a pattern comprising αβαβαβαβαβ, ααβααβααβααβααβ, αααβαααβααα-βαααβαααβ, and ααβαααβααβαααβααβ.

9. The peptide analog of claim 1, selected from the group consisting of

A5: SVSEIQLMHNLGKHLNSMERVEWLRKKLQDVHNF-NH$_2$, (SEQ. ID. NO: 5)

B5: SVSEIQLMHNLGKHLNSMERVEWLRKKLQDVQNF-NH$_2$, (SEQ. ID. NO: 6)

C5: SVSEIQLMHNLGKHLNSMERVEWLRKKLQDVHNF-NH$_2$, (SEQ. ID. NO: 7)

D5: SVSEIQLMHNLGKHLNSMERVEWLRKKLQDVHNF-NH$_2$, (SEQ. ID. NO: 8)

D6: SVSEIQLMHNLGKWLNSMERVEWLRKKLQDVHNF-NH$_2$, (SEQ. ID. NO: 9)

and

D7: SVSEIQLMHNLGKWLNSMERVEWLRKKLQDVHNF-NH$_2$ (SEQ. ID. NO: 10)

wherein bold, underlined residues designate β3 residues having a side chain of the α residue indicated by the letter, and salts thereof.

10. The peptide analog of claim 1, which is an agonist of parathyroid hormone receptor-1.

11. A pharmaceutical composition for treating hypoparathyroidism, the composition comprising a parathyroid hormone receptor agonist-effective amount of PTH, a parathyroid hormone receptor (PTHR-1, PTHR-2) agonist-effective fragment of PTH, a parathyroid hormone related protein (PTHrP), a PTHR-1 or PTHR-2 agonist-effective fragment of PTHrP, M-PTH, a PTHR-1 or PTHR-2 agonist-effective fragment of M-PTH, BA058, or a PTHR-1 or PTHR-2 agonist-effective fragment of BA058, in which at least five non-adjacent α-amino acid residues are replaced with β-amino acid residues, in combination with a pharmaceutically suitable carrier.

12. A method of treating hypoparathyroidism in a mammalian subject, including a human subject, the method comprising administering to the subject a parathyroid hormone receptor agonist-effective amount of a pharmaceutical composition as recited in claim 11.

* * * * *

SEQUENCE LISTING

<160> NUMBER OF SEQ ID NOS: 60

<210> SEQ ID NO 1
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:

```
<221> NAME/KEY: MISC_FEATURE
<222> LOCATION: (23)..(23)
<223> OTHER INFORMATION: Xaa is Beta-3 Trp.
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: MISC_FEATURE
<222> LOCATION: (27)..(27)
<223> OTHER INFORMATION: Xaa is Beta-3 Lys
<220> FEATURE:
<221> NAME/KEY: MISC_FEATURE
<222> LOCATION: (31)..(31)
<223> OTHER INFORMATION: Xaa is Beta-3 Val

<400> SEQUENCE: 1

Ser Val Ser Glu Ile Gln Leu Met His Asn Leu Gly Lys His Leu Asn
1               5                   10                  15

Ser Met Glu Arg Val Glu Xaa Leu Arg Xaa Lys Leu Gln Asp Xaa His
            20                  25                  30

Asn Phe

<210> SEQ ID NO 2
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (24)..(24)
<223> OTHER INFORMATION: Xaa is Beta-3 Leu
<220> FEATURE:
<221> NAME/KEY: MISC_FEATURE
<222> LOCATION: (28)..(28)
<223> OTHER INFORMATION: Xaa is Beta-3 Leu
<220> FEATURE:
<221> NAME/KEY: MISC_FEATURE
<222> LOCATION: (32)..(32)
<223> OTHER INFORMATION: Xaa is Beta-3 Glm

<400> SEQUENCE: 2

Ser Val Ser Glu Ile Gln Leu Met His Asn Leu Gly Lys His Leu Asn
1               5                   10                  15

Ser Met Glu Arg Val Glu Trp Xaa Arg Lys Lys Xaa Gln Asp Val Xaa
            20                  25                  30

Asn Phe

<210> SEQ ID NO 3
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (25)..(25)
<223> OTHER INFORMATION: Xaa is Beta-3 Arg
<220> FEATURE:
<221> NAME/KEY: MISC_FEATURE
<222> LOCATION: (29)..(29)
<223> OTHER INFORMATION: Xaa is Beta-3 Gln
<220> FEATURE:
<221> NAME/KEY: MISC_FEATURE
<222> LOCATION: (33)..(33)
<223> OTHER INFORMATION: Xaa is Beta-3 Asn

<400> SEQUENCE: 3

Ser Val Ser Glu Ile Gln Leu Met His Asn Leu Gly Lys His Leu Asn
```

```
                1               5                  10                 15
Ser Met Glu Arg Val Glu Trp Leu Xaa Lys Lys Leu Xaa Asp Val His
                20                 25                    30

Xaa Phe

<210> SEQ ID NO 4
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (26)..(26)
<223> OTHER INFORMATION: Xaa is Beta-3 Lys
<220> FEATURE:
<221> NAME/KEY: MISC_FEATURE
<222> LOCATION: (30)..(30)
<223> OTHER INFORMATION: Xaa is Beta-3 Asp
<220> FEATURE:
<221> NAME/KEY: MISC_FEATURE
<222> LOCATION: (34)..(34)
<223> OTHER INFORMATION: Xaa is Beta-3 Phe

<400> SEQUENCE: 4

Ser Val Ser Glu Ile Gln Leu Met His Asn Leu Gly Lys His Leu Asn
1               5                  10                 15

Ser Met Glu Arg Val Glu Trp Leu Arg Xaa Lys Leu Gln Xaa Val His
                20                 25                    30

Asn Xaa

<210> SEQ ID NO 5
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (15)..(15)
<223> OTHER INFORMATION: Xaa is Beta-3 Leu
<220> FEATURE:
<221> NAME/KEY: MISC_FEATURE
<222> LOCATION: (19)..(19)
<223> OTHER INFORMATION: Xaa is Beta-3 Glu
<220> FEATURE:
<221> NAME/KEY: MISC_FEATURE
<222> LOCATION: (23)..(23)
<223> OTHER INFORMATION: Xaa is Beta-3 Trp
<220> FEATURE:
<221> NAME/KEY: MISC_FEATURE
<222> LOCATION: (27)..(27)
<223> OTHER INFORMATION: Xaa is Beta-3 Lys
<220> FEATURE:
<221> NAME/KEY: MISC_FEATURE
<222> LOCATION: (31)..(31)
<223> OTHER INFORMATION: Xaa is Beta-3 Val

<400> SEQUENCE: 5

Ser Val Ser Glu Ile Gln Leu Met His Asn Leu Gly Lys His Xaa Asn
1               5                  10                 15

Ser Met Xaa Arg Val Glu Xaa Leu Arg Lys Xaa Leu Gln Asp Xaa His
                20                 25                    30

Asn Phe

<210> SEQ ID NO 6
<211> LENGTH: 34
<212> TYPE: PRT
```

```
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (16)..(16)
<223> OTHER INFORMATION: Xaa is Beta-3 Asn
<220> FEATURE:
<221> NAME/KEY: MISC_FEATURE
<222> LOCATION: (20)..(20)
<223> OTHER INFORMATION: Xaa is Beta-3 Arg
<220> FEATURE:
<221> NAME/KEY: MISC_FEATURE
<222> LOCATION: (24)..(24)
<223> OTHER INFORMATION: Xaa is Beta-3 Leu
<220> FEATURE:
<221> NAME/KEY: MISC_FEATURE
<222> LOCATION: (28)..(28)
<223> OTHER INFORMATION: Xaa is Beta-3 Leu
<220> FEATURE:
<221> NAME/KEY: MISC_FEATURE
<222> LOCATION: (32)..(32)
<223> OTHER INFORMATION: Xaa is Beta-3 Gln

<400> SEQUENCE: 6

Ser Val Ser Glu Ile Gln Leu Met His Asn Leu Gly Lys His Leu Xaa
1               5                   10                  15

Ser Met Glu Xaa Val Glu Trp Xaa Arg Lys Lys Xaa Gln Asp Val Xaa
                20                  25                  30

Asn Phe

<210> SEQ ID NO 7
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (17)..(17)
<223> OTHER INFORMATION: Xaa is Beta-3 Ser
<220> FEATURE:
<221> NAME/KEY: MISC_FEATURE
<222> LOCATION: (21)..(21)
<223> OTHER INFORMATION: Xaa is Beta-3 Val
<220> FEATURE:
<221> NAME/KEY: MISC_FEATURE
<222> LOCATION: (25)..(25)
<223> OTHER INFORMATION: Xaa is Beta-3 Arg
<220> FEATURE:
<221> NAME/KEY: MISC_FEATURE
<222> LOCATION: (29)..(29)
<223> OTHER INFORMATION: Xaa is Beta-3 Gln
<220> FEATURE:
<221> NAME/KEY: MISC_FEATURE
<222> LOCATION: (33)..(33)
<223> OTHER INFORMATION: Xaa is Beta-3 Asn

<400> SEQUENCE: 7

Ser Val Ser Glu Ile Gln Leu Met His Asn Leu Gly Lys His Leu Asn
1               5                   10                  15

Xaa Met Glu Arg Xaa Glu Trp Leu Xaa Lys Lys Leu Xaa Asp Val His
                20                  25                  30

Xaa Phe

<210> SEQ ID NO 8
<211> LENGTH: 34
<212> TYPE: PRT
<213> ORGANISM: Artificial Sequence
<220> FEATURE:
<223> OTHER INFORMATION: Artificial PTH polypeptide.
```

```
<220> FEATURE:
<221> NAME/KEY: MISC_FEATURE
<222> LOCATION: (18)..(18)
<223> OTHER INFORMATION: Xaa is Beta-3 Met
<220> FEATURE:
<221> NAME/KEY: MISC_FEATURE
<222> LOCATION: (22)..(22)
<223> OTHER INFORMATION: Xaa is Beta-3 Glu
<220> FEATURE:
<221> NAME/KEY: MISC_FEATURE
<222> LOCATION: (26)..(26)
<223> OTHER INFORMATION: Xaa is Beta-3 Lys
<220> FEATURE:
<221> NAME/KEY: MISC_FEATURE
<222> LOCATION: (30)..(30)
<223> OTHER INFORMATION: Xaa is Beta-3 Asp
<220> FEATURE:
<221> NAME/KEY: MISC_FEATURE
<222> LOCATION: (34)..(34)
<223> OTHER INFORMATION: Xaa is Beta-3 Phe

<400> SEQUENCE: 8

Ser Val Ser Glu Ile Gln Leu Met His Asn Leu Gly Lys His Leu Asn
1               5                   10                  15

Ser Xaa Glu Arg Val Xaa Trp Leu Arg Xaa Lys Leu Gln Xaa Val His
            20                  25                  30

Asn Xaa

<210> SEQ ID NO 9
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (14)..(14)
<223> OTHER INFORMATION: Xaa is Beta-3 Trp
<220> FEATURE:
<221> NAME/KEY: MISC_FEATURE
<222> LOCATION: (18)..(18)
<223> OTHER INFORMATION: Xaa is Beta-3 Met
<220> FEATURE:
<221> NAME/KEY: MISC_FEATURE
<222> LOCATION: (22)..(22)
<223> OTHER INFORMATION: Xaa is Beta-3 Glu
<220> FEATURE:
<221> NAME/KEY: MISC_FEATURE
<222> LOCATION: (26)..(26)
<223> OTHER INFORMATION: Xaa is Beta-3 Lys
<220> FEATURE:
<221> NAME/KEY: MISC_FEATURE
<222> LOCATION: (30)..(30)
<223> OTHER INFORMATION: Xaa is Beta-3 Asp
<220> FEATURE:
<221> NAME/KEY: MISC_FEATURE
<222> LOCATION: (34)..(34)
<223> OTHER INFORMATION: Xaa is Beta-3 Phe

<400> SEQUENCE: 9

Ser Val Ser Glu Ile Gln Leu Met His Asn Leu Gly Lys Xaa Leu Asn
1               5                   10                  15

Ser Xaa Glu Arg Val Xaa Trp Leu Arg Xaa Lys Leu Gln Xaa Val His
            20                  25                  30

Asn Xaa

<210> SEQ ID NO 10
<211> LENGTH: 34
<212> TYPE: PRT
<213> ORGANISM: Artificial Sequence
<220> FEATURE:
```

```
<223> OTHER INFORMATION: Artificial PTH polypeptide.
<220> FEATURE:
<221> NAME/KEY: MISC_FEATURE
<222> LOCATION: (10)..(10)
<223> OTHER INFORMATION: Xaa is Beta-3 Asn
<220> FEATURE:
<221> NAME/KEY: MISC_FEATURE
<222> LOCATION: (14)..(14)
<223> OTHER INFORMATION: Xaa is Beta-3 Trp
<220> FEATURE:
<221> NAME/KEY: MISC_FEATURE
<222> LOCATION: (18)..(18)
<223> OTHER INFORMATION: Xaa is Beta-3 Met
<220> FEATURE:
<221> NAME/KEY: MISC_FEATURE
<222> LOCATION: (22)..(22)
<223> OTHER INFORMATION: Xaa is Beta-3 Glu
<220> FEATURE:
<221> NAME/KEY: MISC_FEATURE
<222> LOCATION: (26)..(26)
<223> OTHER INFORMATION: Xaa is Beta-3 Lys
<220> FEATURE:
<221> NAME/KEY: MISC_FEATURE
<222> LOCATION: (30)..(30)
<223> OTHER INFORMATION: Xaa is Beta-3 Asp
<220> FEATURE:
<221> NAME/KEY: MISC_FEATURE
<222> LOCATION: (34)..(34)
<223> OTHER INFORMATION: Xaa is Beta-3 Phe

<400> SEQUENCE: 10

Ser Val Ser Glu Ile Gln Leu Met His Xaa Leu Gly Lys Xaa Leu Asn
1               5                   10                  15

Ser Xaa Glu Arg Val Xaa Trp Leu Arg Xaa Lys Leu Gln Xaa Val His
            20                  25                  30

Asn Xaa

<210> SEQ ID NO 11
<211> LENGTH: 115
<212> TYPE: PRT
<213> ORGANISM: Homo sapiens

<400> SEQUENCE: 11

Met Ile Pro Ala Lys Asp Met Ala Lys Val Met Ile Val Met Leu Ala
1               5                   10                  15

Ile Cys Phe Leu Thr Lys Ser Asp Gly Lys Ser Val Lys Lys Arg Ser
                20                  25                  30

Val Ser Glu Ile Gln Leu Met His Asn Leu Gly Lys His Leu Asn Ser
            35                  40                  45

Met Glu Arg Val Glu Trp Leu Arg Lys Lys Leu Gln Asp Val His Asn
        50                  55                  60

Phe Val Ala Leu Gly Ala Pro Leu Ala Pro Arg Asp Ala Gly Ser Gln
65                  70                  75                  80

Arg Pro Arg Lys Lys Glu Asp Asn Val Leu Val Glu Ser His Glu Lys
                85                  90                  95

Ser Leu Gly Glu Ala Asp Lys Ala Asp Val Asn Val Leu Thr Lys Ala
            100                 105                 110

Lys Ser Gln
        115

<210> SEQ ID NO 12
<211> LENGTH: 84
<212> TYPE: PRT
<213> ORGANISM: Homo sapiens

<400> SEQUENCE: 12
```

```
Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 13
<211> LENGTH: 9
<212> TYPE: PRT
<213> ORGANISM: Artificial Sequence
<220> FEATURE:
<223> OTHER INFORMATION: Artificial PTH polypeptide.

<400> SEQUENCE: 13

Ser Val Ser Glu Ile Gln Leu Met His
1               5

<210> SEQ ID NO 14
<211> LENGTH: 34
<212> TYPE: PRT
<213> ORGANISM: Artificial Sequence
<220> FEATURE:
<223> OTHER INFORMATION: Artificial PTH polypeptide.

<400> SEQUENCE: 14

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe

<210> SEQ ID NO 15
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (1)..(1)
<223> OTHER INFORMATION: Xaa is 2-aminocyclopentane carboxylic acid
<220> FEATURE:
<221> NAME/KEY: MISC_FEATURE
<222> LOCATION: (7)..(7)
<223> OTHER INFORMATION: Xaa is 2-aminocyclopentane carboxylic acid

<400> SEQUENCE: 15

Xaa Val Ser Glu Ile Gln Xaa Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe

<210> SEQ ID NO 16
<211> LENGTH: 34
<212> TYPE: PRT
```

```
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (1)..(1)
<223> OTHER INFORMATION: Xaa is 2-aminocyclopentane carboxylic acid
<220> FEATURE:
<221> NAME/KEY: MISC_FEATURE
<222> LOCATION: (5)..(5)
<223> OTHER INFORMATION: Xaa is 2-aminocyclopentane carboxylic acid
<220> FEATURE:
<221> NAME/KEY: MISC_FEATURE
<222> LOCATION: (7)..(7)
<223> OTHER INFORMATION: Xaa is 2-aminocyclopentane carboxylic acid

<400> SEQUENCE: 16

Xaa Val Ser Glu Xaa Gln Xaa Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 17
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (14)..(14)
<223> OTHER INFORMATION: Xaa is Beta-3 Trp
<220> FEATURE:
<221> NAME/KEY: MISC_FEATURE
<222> LOCATION: (18)..(18)
<223> OTHER INFORMATION: Xaa is Beta-3 Met
<220> FEATURE:
<221> NAME/KEY: MISC_FEATURE
<222> LOCATION: (22)..(22)
<223> OTHER INFORMATION: Xaa is Beta-3 Glu
<220> FEATURE:
<221> NAME/KEY: MISC_FEATURE
<222> LOCATION: (26)..(26)
<223> OTHER INFORMATION: Xaa is Beta-3 Lys
<220> FEATURE:
<221> NAME/KEY: MISC_FEATURE
<222> LOCATION: (30)..(30)
<223> OTHER INFORMATION: Xaa is Beta-3 Asp
<220> FEATURE:
<221> NAME/KEY: MISC_FEATURE
<222> LOCATION: (34)..(34)
<223> OTHER INFORMATION: Xaa is Beta-3 Phe

<400> SEQUENCE: 17

Ser Val Ser Glu Ile Gln Leu Met His Asn Leu Gly Lys Xaa Leu Asn
1               5                   10                  15

Ser Xaa Glu Arg Val Xaa Trp Leu Arg Xaa Lys Leu Gln Xaa Val His
            20                  25                  30

Asn Xaa

<210> SEQ ID NO 18
<211> LENGTH: 34
<212> TYPE: PRT
<213> ORGANISM: Artificial Sequence
<220> FEATURE:
<223> OTHER INFORMATION: Artificial PTH polypeptide
<220> FEATURE:
<221> NAME/KEY: MISC_FEATURE
<222> LOCATION: (14)..(14)
<223> OTHER INFORMATION: Xaa is 2-aminocyclopentane carboxylic acid
```

```
<220> FEATURE:
<221> NAME/KEY: MISC_FEATURE
<222> LOCATION: (18)..(18)
<223> OTHER INFORMATION: Xaa is 2-aminocyclopentane carboxylic acid
<220> FEATURE:
<221> NAME/KEY: MISC_FEATURE
<222> LOCATION: (22)..(22)
<223> OTHER INFORMATION: Xaa is Beta-3 Glu
<220> FEATURE:
<221> NAME/KEY: MISC_FEATURE
<222> LOCATION: (30)..(30)
<223> OTHER INFORMATION: Xaa is Beta-3 Asp
<220> FEATURE:
<221> NAME/KEY: MISC_FEATURE
<222> LOCATION: (34)..(34)
<223> OTHER INFORMATION: Xaa is 2-aminocyclopentane carboxylic acid

<400> SEQUENCE: 18

Ser Val Ser Glu Ile Gln Leu Met His Asn Leu Gly Lys Xaa Leu Asn
1               5                   10                  15

Ser Xaa Glu Arg Val Xaa Trp Leu Arg Glx Lys Leu Gln Xaa Val His
            20                  25                  30

Asn Xaa

<210> SEQ ID NO 19
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (14)..(14)
<223> OTHER INFORMATION: Xaa is 2-aminocyclopentane carboxylic acid
<220> FEATURE:
<221> NAME/KEY: MISC_FEATURE
<222> LOCATION: (18)..(18)
<223> OTHER INFORMATION: Xaa is 2-aminocyclopentane carboxylic acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: MISC_FEATURE
<222> LOCATION: (31)..(31)
<223> OTHER INFORMATION: Xaa is 2-aminocyclopentane carboxylic acid
<220> FEATURE:
<221> NAME/KEY: MISC_FEATURE
<222> LOCATION: (34)..(34)
<223> OTHER INFORMATION: Xaa is 2-aminocyclopentane carboxylic acid

<400> SEQUENCE: 19

Ser Val Ser Glu Ile Gln Leu Met His Asn Leu Gly Lys Xaa Leu Asn
1               5                   10                  15

Ser Xaa Glu Arg Val Glx Trp Leu Arg Glx Lys Leu Gln Xaa Val His
            20                  25                  30

Asn Xaa

<210> SEQ ID NO 20
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (1)..(1)
<223> OTHER INFORMATION: Xaa is 2-aminocyclopentane carboxylic acid
<220> FEATURE:
<221> NAME/KEY: MISC_FEATURE
<222> LOCATION: (7)..(7)
```

```
<223> OTHER INFORMATION: Xaa is 2-aminocyclopentane carboxylic acid
<220> FEATURE:
<221> NAME/KEY: MISC_FEATURE
<222> LOCATION: (14)..(14)
<223> OTHER INFORMATION: Xaa is Beta-3 Trp
<220> FEATURE:
<221> NAME/KEY: MISC_FEATURE
<222> LOCATION: (18)..(18)
<223> OTHER INFORMATION: Xaa is Beta-3 Met
<220> FEATURE:
<221> NAME/KEY: MISC_FEATURE
<222> LOCATION: (22)..(22)
<223> OTHER INFORMATION: Xaa is Beta-3 Glu
<220> FEATURE:
<221> NAME/KEY: MISC_FEATURE
<222> LOCATION: (26)..(26)
<223> OTHER INFORMATION: Xaa is Beta-3 Lys
<220> FEATURE:
<221> NAME/KEY: MISC_FEATURE
<222> LOCATION: (30)..(30)
<223> OTHER INFORMATION: Xaa is Beta-3 Asp
<220> FEATURE:
<221> NAME/KEY: MISC_FEATURE
<222> LOCATION: (34)..(34)
<223> OTHER INFORMATION: Xaa is 2-aminocyclopentane carboxylic acid

<400> SEQUENCE: 20

Xaa Val Ser Glu Ile Gln Xaa Met His Asn Leu Gly Lys Xaa Leu Asn
1               5                   10                  15

Ser Xaa Glu Arg Val Xaa Trp Leu Arg Xaa Lys Leu Gln Xaa Val His
            20                  25                  30

Asn Xaa

<210> SEQ ID NO 21
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (1)..(1)
<223> OTHER INFORMATION: Xaa is 2-aminocyclopentane carboxylic acid
<220> FEATURE:
<221> NAME/KEY: MISC_FEATURE
<222> LOCATION: (7)..(7)
<223> OTHER INFORMATION: Xaa is 2-aminocyclopentane carboxylic acid
<220> FEATURE:
<221> NAME/KEY: MISC_FEATURE
<222> LOCATION: (14)..(14)
<223> OTHER INFORMATION: Xaa is 2-aminocyclopentane carboxylic acid
<220> FEATURE:
<221> NAME/KEY: MISC_FEATURE
<222> LOCATION: (18)..(18)
<223> OTHER INFORMATION: Xaa is 2-aminocyclopentane carboxylic acid
<220> FEATURE:
<221> NAME/KEY: MISC_FEATURE
<222> LOCATION: (22)..(22)
<223> OTHER INFORMATION: Xaa is Beta-3 Glu
<220> FEATURE:
<221> NAME/KEY: MISC_FEATURE
<222> LOCATION: (30)..(30)
<223> OTHER INFORMATION: Xaa is Beta-3 Asp
<220> FEATURE:
<221> NAME/KEY: MISC_FEATURE
<222> LOCATION: (34)..(34)
<223> OTHER INFORMATION: Xaa is 2-aminocyclopentane carboxylic acid

<400> SEQUENCE: 21

Xaa Val Ser Glu Ile Gln Xaa Met His Asn Leu Gly Lys Xaa Leu Asn
1               5                   10                  15

Ser Xaa Glu Arg Val Xaa Trp Leu Arg Glx Lys Leu Gln Xaa Val His
            20                  25                  30
```

Asn Xaa

```
<210> SEQ ID NO 22
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (1)..(1)
<223> OTHER INFORMATION: Xaa is 2-aminocyclopentane carboxylic acid
<220> FEATURE:
<221> NAME/KEY: MISC_FEATURE
<222> LOCATION: (7)..(7)
<223> OTHER INFORMATION: Xaa is 2-aminocyclopentane carboxylic acid
<220> FEATURE:
<221> NAME/KEY: MISC_FEATURE
<222> LOCATION: (14)..(14)
<223> OTHER INFORMATION: Xaa is 2-aminocyclopentane carboxylic acid
<220> FEATURE:
<221> NAME/KEY: MISC_FEATURE
<222> LOCATION: (18)..(18)
<223> OTHER INFORMATION: Xaa is 2-aminocyclopentane carboxylic acid
<220> FEATURE:
<221> NAME/KEY: MISC_FEATURE
<222> LOCATION: (30)..(30)
<223> OTHER INFORMATION: Xaa is 2-aminocyclopentane carboxylic acid
<220> FEATURE:
<221> NAME/KEY: MISC_FEATURE
<222> LOCATION: (34)..(34)
<223> OTHER INFORMATION: Xaa is 2-aminocyclopentane carboxylic acid

<400> SEQUENCE: 22

Xaa Val Ser Glu Ile Gln Xaa Met His Asn Leu Gly Lys Xaa Leu Asn
1               5                   10                  15

Ser Xaa Glu Arg Val Glx Trp Leu Arg Glx Lys Leu Gln Xaa Val His
            20                  25                  30

Asn Xaa

<210> SEQ ID NO 23
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (1)..(1)
<223> OTHER INFORMATION: Xaa is 2-aminocyclopentane carboxylic acid
<220> FEATURE:
<221> NAME/KEY: MISC_FEATURE
<222> LOCATION: (5)..(5)
<223> OTHER INFORMATION: Xaa is 2-aminocyclopentane carboxylic acid
<220> FEATURE:
<221> NAME/KEY: MISC_FEATURE
<222> LOCATION: (7)..(7)
<223> OTHER INFORMATION: Xaa is 2-aminocyclopentane carboxylic acid
<220> FEATURE:
<221> NAME/KEY: MISC_FEATURE
<222> LOCATION: (14)..(14)
<223> OTHER INFORMATION: Xaa is Beta-3 Trp
<220> FEATURE:
<221> NAME/KEY: MISC_FEATURE
<222> LOCATION: (18)..(18)
<223> OTHER INFORMATION: Xaa is Beta-3 Met
<220> FEATURE:
<221> NAME/KEY: MISC_FEATURE
<222> LOCATION: (22)..(22)
<223> OTHER INFORMATION: Xaa is Beta-3 Glu
<220> FEATURE:
<221> NAME/KEY: MISC_FEATURE
<222> LOCATION: (26)..(26)
```

```
<223> OTHER INFORMATION: Xaa is Beta-3 Lys
<220> FEATURE:
<221> NAME/KEY: MISC_FEATURE
<222> LOCATION: (30)..(30)
<223> OTHER INFORMATION: Xaa is Beta-3 Asp
<220> FEATURE:
<221> NAME/KEY: MISC_FEATURE
<222> LOCATION: (34)..(34)
<223> OTHER INFORMATION: Xaa is Beta-3 Phe

<400> SEQUENCE: 23

Xaa Val Ser Glu Xaa Gln Xaa Met His Asn Leu Gly Lys Xaa Leu Asn
1               5                   10                  15

Ser Xaa Glu Arg Val Xaa Trp Leu Arg Xaa Lys Leu Gln Xaa Val His
            20                  25                  30

Asn Xaa

<210> SEQ ID NO 24
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (1)..(1)
<223> OTHER INFORMATION: Xaa is 2-aminocyclopentane carboxylic acid
<220> FEATURE:
<221> NAME/KEY: MISC_FEATURE
<222> LOCATION: (5)..(5)
<223> OTHER INFORMATION: Xaa is 2-aminocyclopentane carboxylic acid
<220> FEATURE:
<221> NAME/KEY: MISC_FEATURE
<222> LOCATION: (7)..(7)
<223> OTHER INFORMATION: Xaa is 2-aminocyclopentane carboxylic acid
<220> FEATURE:
<221> NAME/KEY: MISC_FEATURE
<222> LOCATION: (14)..(14)
<223> OTHER INFORMATION: Xaa is 2-aminocyclopentane carboxylic acid
<220> FEATURE:
<221> NAME/KEY: MISC_FEATURE
<222> LOCATION: (18)..(18)
<223> OTHER INFORMATION: Xaa is 2-aminocyclopentane carboxylic acid
<220> FEATURE:
<221> NAME/KEY: MISC_FEATURE
<222> LOCATION: (22)..(22)
<223> OTHER INFORMATION: Xaa is Beta-3 Glu
<220> FEATURE:
<221> NAME/KEY: MISC_FEATURE
<222> LOCATION: (30)..(30)
<223> OTHER INFORMATION: Xaa is Beta-3 Asp
<220> FEATURE:
<221> NAME/KEY: MISC_FEATURE
<222> LOCATION: (34)..(34)
<223> OTHER INFORMATION: Xaa is 2-aminocyclopentane carboxylic acid

<400> SEQUENCE: 24

Xaa Val Ser Glu Xaa Gln Xaa Met His Asn Leu Gly Lys Xaa Leu Asn
1               5                   10                  15

Ser Xaa Glu Arg Val Xaa Trp Leu Arg Glx Lys Leu Gln Xaa Val His
            20                  25                  30

Asn Xaa

<210> SEQ ID NO 25
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
```

```
<222> LOCATION: (1)..(1)
<223> OTHER INFORMATION: Xaa is 2-aminocyclopentane carboxylic acid
<220> FEATURE:
<221> NAME/KEY: MISC_FEATURE
<222> LOCATION: (5)..(5)
<223> OTHER INFORMATION: Xaa is 2-aminocyclopentane carboxylic acid
<220> FEATURE:
<221> NAME/KEY: MISC_FEATURE
<222> LOCATION: (7)..(7)
<223> OTHER INFORMATION: Xaa is 2-aminocyclopentane carboxylic acid
<220> FEATURE:
<221> NAME/KEY: MISC_FEATURE
<222> LOCATION: (14)..(14)
<223> OTHER INFORMATION: Xaa is 2-aminocyclopentane carboxylic acid
<220> FEATURE:
<221> NAME/KEY: MISC_FEATURE
<222> LOCATION: (18)..(18)
<223> OTHER INFORMATION: Xaa is 2-aminocyclopentane carboxylic acid
<220> FEATURE:
<221> NAME/KEY: MISC_FEATURE
<222> LOCATION: (30)..(30)
<223> OTHER INFORMATION: Xaa is 2-aminocyclopentane carboxylic acid
<220> FEATURE:
<221> NAME/KEY: MISC_FEATURE
<222> LOCATION: (34)..(34)
<223> OTHER INFORMATION: Xaa is 2-aminocyclopentane carboxylic acid

<400> SEQUENCE: 25

Xaa Val Ser Glu Xaa Gln Xaa Met His Asn Leu Gly Lys Xaa Leu Asn
1               5                   10                  15

Ser Xaa Glu Arg Val Glx Trp Leu Arg Glx Lys Leu Gln Xaa Val His
            20                  25                  30

Asn Xaa

<210> SEQ ID NO 26
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (11)..(11)
<223> OTHER INFORMATION: Xaa is 2-amino-6-guanidinohexanoic acid

<400> SEQUENCE: 26

Ala Val Ala Glu Ile Gln Leu Met His Gln Xaa Ala Lys Trp Leu Asn
1               5                   10                  15

Ser Met Arg Arg Val Glu Trp Leu Arg Lys Lys Leu Gln Asp Val His
            20                  25                  30

Asn Phe

<210> SEQ ID NO 27
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (1)..(1)
<223> OTHER INFORMATION: Xaa is 2-aminocyclopentane carboxylic acid
<220> FEATURE:
<221> NAME/KEY: MOD_RES
<222> LOCATION: (3)..(3)
<223> OTHER INFORMATION: Aib
<220> FEATURE:
<221> NAME/KEY: MISC_FEATURE
<222> LOCATION: (7)..(7)
<223> OTHER INFORMATION: Xaa is 2-aminocyclopentane carboxylic acid
<220> FEATURE:
```

<221> NAME/KEY: MISC_FEATURE
<222> LOCATION: (11)..(11)
<223> OTHER INFORMATION: Xaa is 2-amino-6-guanidinohexanoic acid

<400> SEQUENCE: 27

Xaa Val Xaa Glu Ile Gln Xaa Met His Gln Xaa Ala Lys Trp Leu Asn
1               5                   10                  15

Ser Met Arg Arg Val Glu Trp Leu Arg Lys Lys Leu Gln Asp Val His
            20                  25                  30

Asn Phe

<210> SEQ ID NO 28
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (1)..(1)
<223> OTHER INFORMATION: Xaa is 2-aminocyclopentane carboxylic acid
<220> FEATURE:
<221> NAME/KEY: MOD_RES
<222> LOCATION: (3)..(3)
<223> OTHER INFORMATION: Aib
<220> FEATURE:
<221> NAME/KEY: MISC_FEATURE
<222> LOCATION: (5)..(5)
<223> OTHER INFORMATION: Xaa is 2-aminocyclopentane carboxylic acid
<220> FEATURE:
<221> NAME/KEY: MISC_FEATURE
<222> LOCATION: (7)..(7)
<223> OTHER INFORMATION: Xaa is 2-aminocyclopentane carboxylic acid
<220> FEATURE:
<221> NAME/KEY: MISC_FEATURE
<222> LOCATION: (11)..(11)
<223> OTHER INFORMATION: Xaa is 2-amino-6-guanidinohexanoic acid

<400> SEQUENCE: 28

Xaa Val Xaa Glu Xaa Gln Xaa Met His Gln Xaa Ala Lys Trp Leu Asn
1               5                   10                  15

Ser Met Arg Arg Val Glu Trp Leu Arg Lys Lys Leu Gln Asp Val His
            20                  25                  30

Asn Phe

<210> SEQ ID NO 29
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (1)..(1)
<223> OTHER INFORMATION: Xaa is 2-aminocyclopentane carboxylic acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: Xaa is 2-amino-6-guanidinohexanoic acid
<220> FEATURE:
<221> NAME/KEY: MISC_FEATURE
<222> LOCATION: (14)..(14)
<223> OTHER INFORMATION: Xaa is Beta-3 Trp
<220> FEATURE:
<221> NAME/KEY: MISC_FEATURE
<222> LOCATION: (18)..(18)
<223> OTHER INFORMATION: Xaa is Beta-3 Met

```
<220> FEATURE:
<221> NAME/KEY: MISC_FEATURE
<222> LOCATION: (22)..(22)
<223> OTHER INFORMATION: Xaa is Beta-3 Glu
<220> FEATURE:
<221> NAME/KEY: MISC_FEATURE
<222> LOCATION: (26)..(26)
<223> OTHER INFORMATION: Xaa is Beta-3 Lys
<220> FEATURE:
<221> NAME/KEY: MISC_FEATURE
<222> LOCATION: (30)..(30)
<223> OTHER INFORMATION: Xaa is Beta-3 Asp
<220> FEATURE:
<221> NAME/KEY: MISC_FEATURE
<222> LOCATION: (34)..(34)
<223> OTHER INFORMATION: Xaa is Beta-3 Phe

<400> SEQUENCE: 29

Ala Val Ala Glu Ile Gln Xaa Met His Gln Xaa Ala Lys Xaa Leu Asn
1               5                   10                  15

Ser Xaa Arg Arg Val Xaa Trp Leu Arg Xaa Lys Leu Gln Xaa Val His
            20                  25                  30

Asn Xaa

<210> SEQ ID NO 30
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (7)..(7)
<223> OTHER INFORMATION: Xaa is 2-aminocyclopentane carboxylic acid
<220> FEATURE:
<221> NAME/KEY: MISC_FEATURE
<222> LOCATION: (11)..(11)
<223> OTHER INFORMATION: Xaa is 2-amino-6-guanidinohexanoic acid
<220> FEATURE:
<221> NAME/KEY: MISC_FEATURE
<222> LOCATION: (14)..(14)
<223> OTHER INFORMATION: Xaa is 2-aminocyclopentane carboxylic acid
<220> FEATURE:
<221> NAME/KEY: MISC_FEATURE
<222> LOCATION: (18)..(18)
<223> OTHER INFORMATION: Xaa is 2-aminocyclopentane carboxylic acid
<220> FEATURE:
<221> NAME/KEY: MISC_FEATURE
<222> LOCATION: (22)..(22)
<223> OTHER INFORMATION: Xaa is Beta-3 Glu
<220> FEATURE:
<221> NAME/KEY: MISC_FEATURE
<222> LOCATION: (30)..(30)
<223> OTHER INFORMATION: Xaa is Beta-3 Asp
<220> FEATURE:
<221> NAME/KEY: MISC_FEATURE
<222> LOCATION: (34)..(34)
<223> OTHER INFORMATION: Xaa is 2-aminocyclopentane carboxylic acid

<400> SEQUENCE: 30

Ala Val Ala Glu Ile Gln Xaa Met His Gln Xaa Ala Lys Xaa Leu Asn
1               5                   10                  15

Ser Xaa Arg Arg Val Xaa Trp Leu Arg Glx Lys Leu Gln Xaa Val His
            20                  25                  30

Asn Xaa

<210> SEQ ID NO 31
<211> LENGTH: 34
<212> TYPE: PRT
<213> ORGANISM: Artificial Sequence
<220> FEATURE:
```

```
<223> OTHER INFORMATION: Artificial PTH polypeptide.
<220> FEATURE:
<221> NAME/KEY: MISC_FEATURE
<222> LOCATION: (7)..(7)
<223> OTHER INFORMATION: Xaa is 2-aminocyclopentane carboxylic acid
<220> FEATURE:
<221> NAME/KEY: MISC_FEATURE
<222> LOCATION: (11)..(11)
<223> OTHER INFORMATION: Xaa is 2-amino-6-guanidinohexanoic acid
<220> FEATURE:
<221> NAME/KEY: MISC_FEATURE
<222> LOCATION: (14)..(14)
<223> OTHER INFORMATION: Xaa is 2-aminocyclopentane carboxylic acid
<220> FEATURE:
<221> NAME/KEY: MISC_FEATURE
<222> LOCATION: (18)..(18)
<223> OTHER INFORMATION: Xaa is 2-aminocyclopentane carboxylic acid
<220> FEATURE:
<221> NAME/KEY: MISC_FEATURE
<222> LOCATION: (30)..(30)
<223> OTHER INFORMATION: Xaa is 2-aminocyclopentane carboxylic acid
<220> FEATURE:
<221> NAME/KEY: MISC_FEATURE
<222> LOCATION: (34)..(34)
<223> OTHER INFORMATION: Xaa is 2-aminocyclopentane carboxylic acid

<400> SEQUENCE: 31

Ala Val Ala Glu Ile Gln Xaa Met His Gln Xaa Ala Lys Xaa Leu Asn
1               5                   10                  15

Ser Xaa Arg Arg Val Glx Trp Leu Arg Glx Lys Leu Gln Xaa Val His
            20                  25                  30

Asn Xaa

<210> SEQ ID NO 32
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (1)..(1)
<223> OTHER INFORMATION: Xaa is 2-aminocyclopentane carboxylic acid
<220> FEATURE:
<221> NAME/KEY: MOD_RES
<222> LOCATION: (3)..(3)
<223> OTHER INFORMATION: Aib
<220> FEATURE:
<221> NAME/KEY: MISC_FEATURE
<222> LOCATION: (7)..(7)
<223> OTHER INFORMATION: Xaa is 2-aminocyclopentane carboxylic acid
<220> FEATURE:
<221> NAME/KEY: MISC_FEATURE
<222> LOCATION: (11)..(11)
<223> OTHER INFORMATION: Xaa is 2-amino-6-guanidinohexanoic acid
<220> FEATURE:
<221> NAME/KEY: MISC_FEATURE
<222> LOCATION: (14)..(14)
<223> OTHER INFORMATION: Xaa is Beta-3 Trp
<220> FEATURE:
<221> NAME/KEY: MISC_FEATURE
<222> LOCATION: (18)..(18)
<223> OTHER INFORMATION: Xaa is Beta-3 Met
<220> FEATURE:
<221> NAME/KEY: MISC_FEATURE
<222> LOCATION: (22)..(22)
<223> OTHER INFORMATION: Xaa is Beta-3 Glu
<220> FEATURE:
<221> NAME/KEY: MISC_FEATURE
<222> LOCATION: (26)..(26)
<223> OTHER INFORMATION: Xaa is Beta-3 Lys
<220> FEATURE:
<221> NAME/KEY: MISC_FEATURE
<222> LOCATION: (30)..(30)
<223> OTHER INFORMATION: Xaa is Beta-3 Asp
```

```
<220> FEATURE:
<221> NAME/KEY: MISC_FEATURE
<222> LOCATION: (34)..(34)
<223> OTHER INFORMATION: Xaa is Beta-3 Phe

<400> SEQUENCE: 32

Xaa Val Xaa Glu Ile Gln Xaa Met His Gln Xaa Ala Lys Xaa Leu Asn
1               5                   10                  15

Ser Xaa Arg Arg Val Xaa Trp Leu Arg Xaa Lys Leu Gln Xaa Val His
            20                  25                  30

Asn Xaa

<210> SEQ ID NO 33
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (1)..(1)
<223> OTHER INFORMATION: Xaa is 2-aminocyclopentane carboxylic acid
<220> FEATURE:
<221> NAME/KEY: MOD_RES
<222> LOCATION: (3)..(3)
<223> OTHER INFORMATION: Aib
<220> FEATURE:
<221> NAME/KEY: MISC_FEATURE
<222> LOCATION: (7)..(7)
<223> OTHER INFORMATION: Xaa is 2-aminocyclopentane carboxylic acid
<220> FEATURE:
<221> NAME/KEY: MISC_FEATURE
<222> LOCATION: (11)..(11)
<223> OTHER INFORMATION: Xaa is 2-amino-6-guanidinohexanoic acid
<220> FEATURE:
<221> NAME/KEY: MISC_FEATURE
<222> LOCATION: (14)..(14)
<223> OTHER INFORMATION: Xaa is 2-aminocyclopentane carboxylic acid
<220> FEATURE:
<221> NAME/KEY: MISC_FEATURE
<222> LOCATION: (18)..(18)
<223> OTHER INFORMATION: Xaa is 2-aminocyclopentane carboxylic acid
<220> FEATURE:
<221> NAME/KEY: MISC_FEATURE
<222> LOCATION: (22)..(22)
<223> OTHER INFORMATION: Xaa is Beta-3 Glu
<220> FEATURE:
<221> NAME/KEY: MISC_FEATURE
<222> LOCATION: (30)..(30)
<223> OTHER INFORMATION: Xaa is Beta-3 Asp
<220> FEATURE:
<221> NAME/KEY: MISC_FEATURE
<222> LOCATION: (34)..(34)
<223> OTHER INFORMATION: Xaa is 2-aminocyclopentane carboxylic acid

<400> SEQUENCE: 33

Xaa Val Xaa Glu Ile Gln Xaa Met His Gln Xaa Ala Lys Xaa Leu Asn
1               5                   10                  15

Ser Xaa Arg Arg Val Xaa Trp Leu Arg Glx Lys Leu Gln Xaa Val His
            20                  25                  30

Asn Xaa

<210> SEQ ID NO 34
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (1)..(1)
```

```
<223> OTHER INFORMATION: Xaa is 2-aminocyclopentane carboxylic acid
<220> FEATURE:
<221> NAME/KEY: MOD_RES
<222> LOCATION: (3)..(3)
<223> OTHER INFORMATION: Aib
<220> FEATURE:
<221> NAME/KEY: MISC_FEATURE
<222> LOCATION: (7)..(7)
<223> OTHER INFORMATION: Xaa is 2-aminocyclopentane carboxylic acid
<220> FEATURE:
<221> NAME/KEY: MISC_FEATURE
<222> LOCATION: (11)..(11)
<223> OTHER INFORMATION: Xaa is 2-amino-6-guanidinohexanoic acid
<220> FEATURE:
<221> NAME/KEY: MISC_FEATURE
<222> LOCATION: (14)..(14)
<223> OTHER INFORMATION: Xaa is 2-aminocyclopentane carboxylic acid
<220> FEATURE:
<221> NAME/KEY: MISC_FEATURE
<222> LOCATION: (18)..(18)
<223> OTHER INFORMATION: Xaa is 2-aminocyclopentane carboxylic acid
<220> FEATURE:
<221> NAME/KEY: MISC_FEATURE
<222> LOCATION: (30)..(30)
<223> OTHER INFORMATION: Xaa is 2-aminocyclopentane carboxylic acid
<220> FEATURE:
<221> NAME/KEY: MISC_FEATURE
<222> LOCATION: (34)..(34)
<223> OTHER INFORMATION: Xaa is 2-aminocyclopentane carboxylic acid

<400> SEQUENCE: 34

Xaa Val Xaa Glu Ile Gln Xaa Met His Gln Xaa Ala Lys Xaa Leu Asn
1               5                   10                  15

Ser Xaa Arg Arg Val Glx Trp Leu Arg Glx Lys Leu Gln Xaa Val His
            20                  25                  30

Asn Xaa

<210> SEQ ID NO 35
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (1)..(1)
<223> OTHER INFORMATION: Xaa is 2-aminocyclopentane carboxylic acid
<220> FEATURE:
<221> NAME/KEY: MOD_RES
<222> LOCATION: (3)..(3)
<223> OTHER INFORMATION: Aib
<220> FEATURE:
<221> NAME/KEY: MISC_FEATURE
<222> LOCATION: (5)..(5)
<223> OTHER INFORMATION: Xaa is 2-aminocyclopentane carboxylic acid
<220> FEATURE:
<221> NAME/KEY: MISC_FEATURE
<222> LOCATION: (7)..(7)
<223> OTHER INFORMATION: Xaa is 2-aminocyclopentane carboxylic acid
<220> FEATURE:
<221> NAME/KEY: MISC_FEATURE
<222> LOCATION: (11)..(11)
<223> OTHER INFORMATION: Xaa is 2-amino-6-guanidinohexanoic acid
<220> FEATURE:
<221> NAME/KEY: MISC_FEATURE
<222> LOCATION: (14)..(14)
<223> OTHER INFORMATION: Xaa is Beta-3 Trp
<220> FEATURE:
<221> NAME/KEY: MISC_FEATURE
<222> LOCATION: (18)..(18)
<223> OTHER INFORMATION: Xaa is Beta-3 Met
<220> FEATURE:
<221> NAME/KEY: MISC_FEATURE
<222> LOCATION: (22)..(22)
<223> OTHER INFORMATION: Xaa is Beta-3 Glu
```

-continued

```
<220> FEATURE:
<221> NAME/KEY: MISC_FEATURE
<222> LOCATION: (26)..(26)
<223> OTHER INFORMATION: Xaa is Beta-3 Lys
<220> FEATURE:
<221> NAME/KEY: MISC_FEATURE
<222> LOCATION: (30)..(30)
<223> OTHER INFORMATION: Xaa is Beta-3 Asp
<220> FEATURE:
<221> NAME/KEY: MISC_FEATURE
<222> LOCATION: (34)..(34)
<223> OTHER INFORMATION: Xaa is Beta-3 Phe

<400> SEQUENCE: 35

Xaa Val Xaa Glu Xaa Gln Xaa Met His Gln Xaa Ala Lys Xaa Leu Asn
1               5                   10                  15

Ser Xaa Arg Arg Val Xaa Trp Leu Arg Xaa Lys Leu Gln Xaa Val His
            20                  25                  30

Asn Xaa

<210> SEQ ID NO 36
<211> LENGTH: 35
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (2)..(2)
<223> OTHER INFORMATION: Xaa is 2-aminocyclopentane carboxylic acid
<220> FEATURE:
<221> NAME/KEY: MOD_RES
<222> LOCATION: (4)..(4)
<223> OTHER INFORMATION: Aib
<220> FEATURE:
<221> NAME/KEY: MISC_FEATURE
<222> LOCATION: (6)..(6)
<223> OTHER INFORMATION: Xaa is 2-aminocyclopentane carboxylic acid
<220> FEATURE:
<221> NAME/KEY: MISC_FEATURE
<222> LOCATION: (8)..(8)
<223> OTHER INFORMATION: Xaa is 2-aminocyclopentane carboxylic acid
<220> FEATURE:
<221> NAME/KEY: MISC_FEATURE
<222> LOCATION: (12)..(12)
<223> OTHER INFORMATION: Xaa is 2-amino-6-guanidinohexanoic acid
<220> FEATURE:
<221> NAME/KEY: MISC_FEATURE
<222> LOCATION: (15)..(15)
<223> OTHER INFORMATION: Xaa is 2-aminocyclopentane carboxylic acid
<220> FEATURE:
<221> NAME/KEY: MISC_FEATURE
<222> LOCATION: (19)..(19)
<223> OTHER INFORMATION: Xaa is 2-aminocyclopentane carboxylic acid
<220> FEATURE:
<221> NAME/KEY: MISC_FEATURE
<222> LOCATION: (23)..(32)
<223> OTHER INFORMATION: Xaa is Beta-3 Glu
<220> FEATURE:
<221> NAME/KEY: MISC_FEATURE
<222> LOCATION: (31)..(31)
<223> OTHER INFORMATION: Xaa is Beta-3 Asp
<220> FEATURE:
<221> NAME/KEY: MISC_FEATURE
<222> LOCATION: (35)..(35)
<223> OTHER INFORMATION: Xaa is 2-aminocyclopentane carboxylic acid

<400> SEQUENCE: 36

His Xaa Val Xaa Glu Xaa Gln Xaa Met His Gln Xaa Ala Lys Xaa Leu
1               5                   10                  15

Asn Ser Xaa Arg Arg Val Xaa Trp Leu Arg Glx Lys Leu Gln Xaa Val
            20                  25                  30
```

His Asn Xaa
         35

<210> SEQ ID NO 37
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (1)..(1)
<223> OTHER INFORMATION: Xaa is 2-aminocyclopentane carboxylic acid
<220> FEATURE:
<221> NAME/KEY: MOD_RES
<222> LOCATION: (3)..(3)
<223> OTHER INFORMATION: Aib
<220> FEATURE:
<221> NAME/KEY: MISC_FEATURE
<222> LOCATION: (5)..(5)
<223> OTHER INFORMATION: Xaa is 2-aminocyclopentane carboxylic acid
<220> FEATURE:
<221> NAME/KEY: MISC_FEATURE
<222> LOCATION: (7)..(7)
<223> OTHER INFORMATION: Xaa is 2-aminocyclopentane carboxylic acid
<220> FEATURE:
<221> NAME/KEY: MISC_FEATURE
<222> LOCATION: (11)..(11)
<223> OTHER INFORMATION: Xaa is 2-amino-6-guanidinohexanoic acid
<220> FEATURE:
<221> NAME/KEY: MISC_FEATURE
<222> LOCATION: (14)..(14)
<223> OTHER INFORMATION: Xaa is 2-aminocyclopentane carboxylic acid
<220> FEATURE:
<221> NAME/KEY: MISC_FEATURE
<222> LOCATION: (18)..(18)
<223> OTHER INFORMATION: Xaa is 2-aminocyclopentane carboxylic acid
<220> FEATURE:
<221> NAME/KEY: MISC_FEATURE
<222> LOCATION: (30)..(30)
<223> OTHER INFORMATION: Xaa is 2-aminocyclopentane carboxylic acid
<220> FEATURE:
<221> NAME/KEY: MISC_FEATURE
<222> LOCATION: (34)..(34)
<223> OTHER INFORMATION: Xaa is 2-aminocyclopentane carboxylic acid

<400> SEQUENCE: 37

Xaa Val Xaa Glu Xaa Gln Xaa Met His Gln Xaa Ala Lys Xaa Leu Asn
1               5                  10                  15

Ser Xaa Arg Arg Val Glx Trp Leu Arg Glx Lys Leu Gln Xaa Val His
            20                  25                  30

Asn Xaa

<210> SEQ ID NO 38
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (1)..(1)
<223> OTHER INFORMATION: Xaa is Beta-3 Ser
<220> FEATURE:
<221> NAME/KEY: MISC_FEATURE
<222> LOCATION: (5)..(5)
<223> OTHER INFORMATION: Xaa is 2-aminocyclopentane carboxylic acid
<220> FEATURE:
<221> NAME/KEY: MISC_FEATURE
<222> LOCATION: (7)..(7)
<223> OTHER INFORMATION: Xaa is 2-aminocyclopentane carboxylic acid
<220> FEATURE:
<221> NAME/KEY: MISC_FEATURE
<222> LOCATION: (14)..(14)

<223> OTHER INFORMATION: Xaa is 2-aminocyclopentane carboxylic acid
<220> FEATURE:
<221> NAME/KEY: MISC_FEATURE
<222> LOCATION: (18)..(18)
<223> OTHER INFORMATION: Xaa is 2-aminocyclopentane carboxylic acid
<220> FEATURE:
<221> NAME/KEY: MISC_FEATURE
<222> LOCATION: (30)..(30)
<223> OTHER INFORMATION: Xaa is 2-aminocyclopentane carboxylic acid
<220> FEATURE:
<221> NAME/KEY: MISC_FEATURE
<222> LOCATION: (34)..(34)
<223> OTHER INFORMATION: Xaa is 2-aminocyclopentane carboxylic acid

<400> SEQUENCE: 38

Xaa Val Ser Glu Xaa Gln Xaa Met His Asn Leu Gly Lys Xaa Leu Asn
1               5                   10                  15

Ser Xaa Glu Arg Val Glx Trp Leu Arg Glx Lys Leu Gln Xaa Val His
            20                  25                  30

Asn Xaa

<210> SEQ ID NO 39
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (1)..(1)
<223> OTHER INFORMATION: Xaa is Beta-3 Ser
<220> FEATURE:
<221> NAME/KEY: MOD_RES
<222> LOCATION: (3)..(3)
<223> OTHER INFORMATION: Aib
<220> FEATURE:
<221> NAME/KEY: MISC_FEATURE
<222> LOCATION: (5)..(5)
<223> OTHER INFORMATION: Xaa is 2-aminocyclopentane carboxylic acid
<220> FEATURE:
<221> NAME/KEY: MISC_FEATURE
<222> LOCATION: (7)..(7)
<223> OTHER INFORMATION: Xaa is 2-aminocyclopentane carboxylic acid
<220> FEATURE:
<221> NAME/KEY: MISC_FEATURE
<222> LOCATION: (14)..(14)
<223> OTHER INFORMATION: Xaa is 2-aminocyclopentane carboxylic acid
<220> FEATURE:
<221> NAME/KEY: MISC_FEATURE
<222> LOCATION: (18)..(18)
<223> OTHER INFORMATION: Xaa is 2-aminocyclopentane carboxylic acid
<220> FEATURE:
<221> NAME/KEY: MISC_FEATURE
<222> LOCATION: (30)..(30)
<223> OTHER INFORMATION: Xaa is 2-aminocyclopentane carboxylic acid
<220> FEATURE:
<221> NAME/KEY: MISC_FEATURE
<222> LOCATION: (34)..(34)
<223> OTHER INFORMATION: Xaa is 2-aminocyclopentane carboxylic acid

<400> SEQUENCE: 39

Xaa Val Xaa Glu Ile Gln Xaa Met His Asn Leu Gly Lys Xaa Leu Asn
1               5                   10                  15

Ser Xaa Glu Arg Val Glx Trp Leu Arg Glx Lys Leu Gln Xaa Val His
            20                  25                  30

Asn Xaa

<210> SEQ ID NO 40
<211> LENGTH: 34
<212> TYPE: PRT
<213> ORGANISM: Artificial Sequence

```
<220> FEATURE:
<223> OTHER INFORMATION: Artificial PTH polypeptide.
<220> FEATURE:
<221> NAME/KEY: MOD_RES
<222> LOCATION: (29)..(29)
<223> OTHER INFORMATION: Aib

<400> SEQUENCE: 40

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Xaa Lys Leu His
            20                  25                  30

Thr Ala

<210> SEQ ID NO 41
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (14)..(14)
<223> OTHER INFORMATION: Xaa is Beta-3 Ser
<220> FEATURE:
<221> NAME/KEY: MISC_FEATURE
<222> LOCATION: (18)..(18)
<223> OTHER INFORMATION: Xaa is Beta-3 Leu
<220> FEATURE:
<221> NAME/KEY: MISC_FEATURE
<222> LOCATION: (22)..(22)
<223> OTHER INFORMATION: Xaa is Beta-3 Glu
<220> FEATURE:
<221> NAME/KEY: MISC_FEATURE
<222> LOCATION: (26)..(26)
<223> OTHER INFORMATION: Xaa is Beta-3 Lys
<220> FEATURE:
<221> NAME/KEY: MOD_RES
<222> LOCATION: (29)..(29)
<223> OTHER INFORMATION: Aib
<220> FEATURE:
<221> NAME/KEY: MISC_FEATURE
<222> LOCATION: (30)..(30)
<223> OTHER INFORMATION: Xaa is Beta-3 Lys
<220> FEATURE:
<221> NAME/KEY: MISC_FEATURE
<222> LOCATION: (34)..(34)
<223> OTHER INFORMATION: Xaa is Beta-3 Ala

<400> SEQUENCE: 41

Ala Val Ser Glu His Gln Leu Leu His Asp Lys Gly Lys Xaa Ile Gln
1               5                   10                  15

Asp Xaa Arg Arg Arg Xaa Leu Leu Glu Xaa Leu Leu Xaa Xaa Leu His
            20                  25                  30

Thr Xaa

<210> SEQ ID NO 42
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (14)..(14)
<223> OTHER INFORMATION: Xaa is 2-aminocyclopentane carboxylic acid
<220> FEATURE:
<221> NAME/KEY: MISC_FEATURE
<222> LOCATION: (18)..(18)
<223> OTHER INFORMATION: Xaa is 2-aminocyclopentane carboxylic acid
<220> FEATURE:
```

```
<221> NAME/KEY: MOD_RES
<222> LOCATION: (29)..(29)
<223> OTHER INFORMATION: Aib
<220> FEATURE:
<221> NAME/KEY: MISC_FEATURE
<222> LOCATION: (30)..(30)
<223> OTHER INFORMATION: Xaa is 2-aminocyclopentane carboxylic acid
<220> FEATURE:
<221> NAME/KEY: MISC_FEATURE
<222> LOCATION: (34)..(34)
<223> OTHER INFORMATION: Xaa is 2-aminocyclopentane carboxylic acid

<400> SEQUENCE: 42

Ala Val Ser Glu His Gln Leu Leu His Asp Lys Gly Lys Xaa Ile Gln
1               5                   10                  15

Asp Xaa Arg Arg Arg Glx Leu Leu Glu Glx Leu Leu Xaa Xaa Leu His
            20                  25                  30

Thr Xaa

<210> SEQ ID NO 43
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (1)..(1)
<223> OTHER INFORMATION: Xaa is 2-aminocyclopentane carboxylic acid
<220> FEATURE:
<221> NAME/KEY: MISC_FEATURE
<222> LOCATION: (7)..(7)
<223> OTHER INFORMATION: Xaa is 2-aminocyclopentane carboxylic acid
<220> FEATURE:
<221> NAME/KEY: MOD_RES
<222> LOCATION: (29)..(29)
<223> OTHER INFORMATION: Aib

<400> SEQUENCE: 43

Xaa Val Ser Glu His Gln Xaa Leu His Asp Lys Gly Lys Ser Ile Gln
1               5                   10                  15

Asp Leu Arg Arg Arg Glu Leu Leu Glu Lys Leu Leu Xaa Lys Leu His
            20                  25                  30

Thr Ala

<210> SEQ ID NO 44
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (1)..(1)
<223> OTHER INFORMATION: Xaa is 2-aminocyclopentane carboxylic acid
<220> FEATURE:
<221> NAME/KEY: MISC_FEATURE
<222> LOCATION: (7)..(7)
<223> OTHER INFORMATION: Xaa is 2-aminocyclopentane carboxylic acid
<220> FEATURE:
<221> NAME/KEY: MISC_FEATURE
<222> LOCATION: (14)..(14)
<223> OTHER INFORMATION: Xaa is Beta-3 Ser
<220> FEATURE:
<221> NAME/KEY: MISC_FEATURE
<222> LOCATION: (18)..(18)
<223> OTHER INFORMATION: Xaa is Beta-3 Leu
<220> FEATURE:
<221> NAME/KEY: MISC_FEATURE
<222> LOCATION: (22)..(22)
<223> OTHER INFORMATION: Xaa is Beta-3 Glu
```

```
<220> FEATURE:
<221> NAME/KEY: MISC_FEATURE
<222> LOCATION: (26)..(26)
<223> OTHER INFORMATION: Xaa is Beta-3 Lys
<220> FEATURE:
<221> NAME/KEY: MOD_RES
<222> LOCATION: (29)..(29)
<223> OTHER INFORMATION: Aib
<220> FEATURE:
<221> NAME/KEY: MISC_FEATURE
<222> LOCATION: (30)..(30)
<223> OTHER INFORMATION: Xaa is Beta-3 Lys
<220> FEATURE:
<221> NAME/KEY: MISC_FEATURE
<222> LOCATION: (34)..(34)
<223> OTHER INFORMATION: Xaa is 2-aminocyclopentane carboxylic acid

<400> SEQUENCE: 44

Xaa Val Ser Glu His Gln Xaa Leu His Asp Lys Gly Lys Xaa Ile Gln
1               5                   10                  15

Asp Xaa Arg Arg Arg Xaa Leu Leu Glu Xaa Leu Leu Xaa Xaa Leu His
            20                  25                  30

Thr Xaa

<210> SEQ ID NO 45
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (1)..(1)
<223> OTHER INFORMATION: Xaa is 2-aminocyclopentane carboxylic acid
<220> FEATURE:
<221> NAME/KEY: MISC_FEATURE
<222> LOCATION: (7)..(7)
<223> OTHER INFORMATION: Xaa is 2-aminocyclopentane carboxylic acid
<220> FEATURE:
<221> NAME/KEY: MISC_FEATURE
<222> LOCATION: (14)..(14)
<223> OTHER INFORMATION: Xaa is 2-aminocyclopentane carboxylic acid
<220> FEATURE:
<221> NAME/KEY: MISC_FEATURE
<222> LOCATION: (18)..(18)
<223> OTHER INFORMATION: Xaa is 2-aminocyclopentane carboxylic acid
<220> FEATURE:
<221> NAME/KEY: MOD_RES
<222> LOCATION: (29)..(29)
<223> OTHER INFORMATION: Aib
<220> FEATURE:
<221> NAME/KEY: MISC_FEATURE
<222> LOCATION: (30)..(30)
<223> OTHER INFORMATION: Xaa is 2-aminocyclopentane carboxylic acid
<220> FEATURE:
<221> NAME/KEY: MISC_FEATURE
<222> LOCATION: (34)..(34)
<223> OTHER INFORMATION: Xaa is 2-aminocyclopentane carboxylic acid

<400> SEQUENCE: 45

Xaa Val Ser Glu His Gln Xaa Leu His Asp Lys Gly Lys Xaa Ile Gln
1               5                   10                  15

Asp Xaa Arg Arg Arg Glx Leu Leu Glu Glx Leu Leu Xaa Xaa Leu His
            20                  25                  30

Thr Xaa

<210> SEQ ID NO 46
<211> LENGTH: 34
<212> TYPE: PRT
<213> ORGANISM: Artificial Sequence
<220> FEATURE:
```

```
<223> OTHER INFORMATION: Artificial PTH polypeptide.
<220> FEATURE:
<221> NAME/KEY: MISC_FEATURE
<222> LOCATION: (1)..(1)
<223> OTHER INFORMATION: Xaa is 2-aminocyclopentane carboxylic acid
<220> FEATURE:
<221> NAME/KEY: MISC_FEATURE
<222> LOCATION: (5)..(5)
<223> OTHER INFORMATION: Xaa is 2-aminocyclopentane carboxylic acid
<220> FEATURE:
<221> NAME/KEY: MISC_FEATURE
<222> LOCATION: (7)..(7)
<220> FEATURE:
<221> NAME/KEY: MOD_RES
<222> LOCATION: (29)..(29)
<223> OTHER INFORMATION: Aib

<400> SEQUENCE: 46

Xaa Val Ser Glu Xaa Gln Xaa Leu His Asp Lys Gly Lys Ser Ile Gln
1               5                   10                  15

Asp Leu Arg Arg Arg Glu Leu Leu Glu Lys Leu Leu Xaa Lys Leu His
            20                  25                  30

Thr Ala

<210> SEQ ID NO 47
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (1)..(1)
<223> OTHER INFORMATION: Xaa is 2-aminocyclopentane carboxylic acid
<220> FEATURE:
<221> NAME/KEY: MISC_FEATURE
<222> LOCATION: (5)..(5)
<223> OTHER INFORMATION: Xaa is 2-aminocyclopentane carboxylic acid
<220> FEATURE:
<221> NAME/KEY: MISC_FEATURE
<222> LOCATION: (7)..(7)
<223> OTHER INFORMATION: Xaa is 2-aminocyclopentane carboxylic acid
<220> FEATURE:
<221> NAME/KEY: MISC_FEATURE
<222> LOCATION: (14)..(14)
<223> OTHER INFORMATION: Xaa is Beta-3 Ser
<220> FEATURE:
<221> NAME/KEY: MISC_FEATURE
<222> LOCATION: (18)..(18)
<223> OTHER INFORMATION: Xaa is Beta-3 Leu
<220> FEATURE:
<221> NAME/KEY: MISC_FEATURE
<222> LOCATION: (22)..(22)
<223> OTHER INFORMATION: Xaa is Beta-3 Glu
<220> FEATURE:
<221> NAME/KEY: MISC_FEATURE
<222> LOCATION: (26)..(26)
<223> OTHER INFORMATION: Xaa is Beta-3 Lys
<220> FEATURE:
<221> NAME/KEY: MOD_RES
<222> LOCATION: (29)..(29)
<223> OTHER INFORMATION: Aib
<220> FEATURE:
<221> NAME/KEY: MISC_FEATURE
<222> LOCATION: (30)..(30)
<223> OTHER INFORMATION: Xaa is Beta-3 Lys
<220> FEATURE:
<221> NAME/KEY: MISC_FEATURE
<222> LOCATION: (34)..(34)
<223> OTHER INFORMATION: Xaa is 2-aminocyclopentane carboxylic acid

<400> SEQUENCE: 47

Xaa Val Ser Glu Xaa Gln Xaa Leu His Asp Lys Gly Lys Xaa Ile Gln
1               5                   10                  15
```

```
Asp Xaa Arg Arg Arg Xaa Leu Leu Glu Xaa Leu Leu Xaa Xaa Leu His
            20                  25                  30

Thr Xaa

<210> SEQ ID NO 48
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (1)..(1)
<223> OTHER INFORMATION: Xaa is 2-aminocyclopentane carboxylic acid
<220> FEATURE:
<221> NAME/KEY: MISC_FEATURE
<222> LOCATION: (5)..(5)
<223> OTHER INFORMATION: Xaa is 2-aminocyclopentane carboxylic acid
<220> FEATURE:
<221> NAME/KEY: MISC_FEATURE
<222> LOCATION: (7)..(7)
<223> OTHER INFORMATION: Xaa is 2-aminocyclopentane carboxylic acid
<220> FEATURE:
<221> NAME/KEY: MISC_FEATURE
<222> LOCATION: (14)..(14)
<223> OTHER INFORMATION: Xaa is 2-aminocyclopentane carboxylic acid
<220> FEATURE:
<221> NAME/KEY: MISC_FEATURE
<222> LOCATION: (18)..(18)
<223> OTHER INFORMATION: Xaa is 2-aminocyclopentane carboxylic acid
<220> FEATURE:
<221> NAME/KEY: MOD_RES
<222> LOCATION: (29)..(29)
<223> OTHER INFORMATION: Aib
<220> FEATURE:
<221> NAME/KEY: MISC_FEATURE
<222> LOCATION: (30)..(30)
<223> OTHER INFORMATION: Xaa is 2-aminocyclopentane carboxylic acid
<220> FEATURE:
<221> NAME/KEY: MISC_FEATURE
<222> LOCATION: (34)..(34)
<223> OTHER INFORMATION: Xaa is 2-aminocyclopentane carboxylic acid

<400> SEQUENCE: 48

Xaa Val Ser Glu Xaa Gln Xaa Leu His Asp Lys Gly Lys Xaa Ile Gln
1               5                   10                  15

Asp Xaa Arg Arg Arg Glx Leu Leu Glu Glx Leu Leu Xaa Xaa Leu His
            20                  25                  30

Thr Xaa

<210> SEQ ID NO 49
<211> LENGTH: 34
<212> TYPE: PRT
<213> ORGANISM: Artificial Sequence
<220> FEATURE:
<223> OTHER INFORMATION: Artificial PTH polypeptide.

<400> SEQUENCE: 49

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 50
<211> LENGTH: 34
<212> TYPE: PRT
<213> ORGANISM: Artificial Sequence
```

```
<220> FEATURE:
<223> OTHER INFORMATION: Artificial PTH polypeptide.

<400> SEQUENCE: 50

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala

<210> SEQ ID NO 51
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (14)..(14)
<223> OTHER INFORMATION: Xaa is Beta-3 Ser
<220> FEATURE:
<221> NAME/KEY: MISC_FEATURE
<222> LOCATION: (18)..(18)
<223> OTHER INFORMATION: Xaa is Beta-3 Leu
<220> FEATURE:
<221> NAME/KEY: MISC_FEATURE
<222> LOCATION: (22)..(22)
<223> OTHER INFORMATION: Xaa is Beta-3 Phe
<220> FEATURE:
<221> NAME/KEY: MISC_FEATURE
<222> LOCATION: (26)..(26)
<223> OTHER INFORMATION: Xaa is Beta-3 Lys
<220> FEATURE:
<221> NAME/KEY: MISC_FEATURE
<222> LOCATION: (30)..(30)
<223> OTHER INFORMATION: Xaa is Beta-3 Glu
<220> FEATURE:
<221> NAME/KEY: MISC_FEATURE
<222> LOCATION: (34)..(34)
<223> OTHER INFORMATION: Xaa is Beta-3 Ala

<400> SEQUENCE: 51

Ala Val Ser Glu His Gln Leu Leu His Asp Lys Gly Lys Xaa Ile Gln
1               5                   10                  15

Asp Xaa Arg Arg Arg Xaa Phe Leu His Xaa Leu Ile Ala Xaa Ile His
            20                  25                  30

Thr Xaa

<210> SEQ ID NO 52
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (14)..(14)
<223> OTHER INFORMATION: Xaa is 2-aminocyclopentane carboxylic acid
<220> FEATURE:
<221> NAME/KEY: MISC_FEATURE
<222> LOCATION: (18)..(18)
<223> OTHER INFORMATION: Xaa is 2-aminocyclopentane carboxylic acid
<220> FEATURE:
<221> NAME/KEY: MISC_FEATURE
<222> LOCATION: (30)..(30)
<223> OTHER INFORMATION: Xaa is 2-aminocyclopentane carboxylic acid
<220> FEATURE:
<221> NAME/KEY: MISC_FEATURE
<222> LOCATION: (34)..(34)
<223> OTHER INFORMATION: Xaa is 2-aminocyclopentane carboxylic acid
```

<400> SEQUENCE: 52

Ala Val Ser Glu His Gln Leu Leu His Asp Lys Gly Lys Xaa Ile Gln
1               5                   10                  15

Asp Xaa Arg Arg Arg Glx Phe Leu His Glx Leu Ile Ala Xaa Ile His
                20                  25                  30

Thr Xaa

<210> SEQ ID NO 53
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (1)..(1)
<223> OTHER INFORMATION: Xaa is 2-aminocyclopentane carboxylic acid
<220> FEATURE:
<221> NAME/KEY: MISC_FEATURE
<222> LOCATION: (5)..(5)
<223> OTHER INFORMATION: Xaa is 2-aminocyclopentane carboxylic acid
<220> FEATURE:
<221> NAME/KEY: MISC_FEATURE
<222> LOCATION: (7)..(7)
<223> OTHER INFORMATION: Xaa is 2-aminocyclopentane carboxylic acid
<220> FEATURE:
<221> NAME/KEY: MISC_FEATURE
<222> LOCATION: (14)..(14)
<223> OTHER INFORMATION: Xaa is Beta-3 Ser
<220> FEATURE:
<221> NAME/KEY: MISC_FEATURE
<222> LOCATION: (18)..(18)
<223> OTHER INFORMATION: Xaa is Beta-3 Leu
<220> FEATURE:
<221> NAME/KEY: MISC_FEATURE
<222> LOCATION: (22)..(22)
<223> OTHER INFORMATION: Xaa is Beta-3 Phe
<220> FEATURE:
<221> NAME/KEY: MISC_FEATURE
<222> LOCATION: (26)..(26)
<223> OTHER INFORMATION: Xaa is Beta-3 Lys
<220> FEATURE:
<221> NAME/KEY: MISC_FEATURE
<222> LOCATION: (30)..(30)
<223> OTHER INFORMATION: Xaa is Beta-3 Glu
<220> FEATURE:
<221> NAME/KEY: MISC_FEATURE
<222> LOCATION: (34)..(34)
<223> OTHER INFORMATION: Xaa is Beta-3 Ala

<400> SEQUENCE: 53

Xaa Val Ser Glu Xaa Gln Xaa Leu His Asp Lys Gly Lys Xaa Ile Gln
1               5                   10                  15

Asp Xaa Arg Arg Arg Xaa Phe Leu His Xaa Leu Ile Ala Xaa Ile His
                20                  25                  30

Thr Xaa

<210> SEQ ID NO 54
<211> LENGTH: 34
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (1)..(1)
<223> OTHER INFORMATION: Xaa is 2-aminocyclopentane carboxylic acid
<220> FEATURE:
<221> NAME/KEY: MISC_FEATURE
<222> LOCATION: (5)..(5)
<223> OTHER INFORMATION: Xaa is 2-aminocyclopentane carboxylic acid

```
<220> FEATURE:
<221> NAME/KEY: MISC_FEATURE
<222> LOCATION: (7)..(7)
<223> OTHER INFORMATION: Xaa is 2-aminocyclopentane carboxylic acid
<220> FEATURE:
<221> NAME/KEY: MISC_FEATURE
<222> LOCATION: (14)..(14)
<223> OTHER INFORMATION: Xaa is 2-aminocyclopentane carboxylic acid
<220> FEATURE:
<221> NAME/KEY: MISC_FEATURE
<222> LOCATION: (18)..(18)
<223> OTHER INFORMATION: Xaa is 2-aminocyclopentane carboxylic acid
<220> FEATURE:
<221> NAME/KEY: MISC_FEATURE
<222> LOCATION: (30)..(30)
<223> OTHER INFORMATION: Xaa is 2-aminocyclopentane carboxylic acid
<220> FEATURE:
<221> NAME/KEY: MISC_FEATURE
<222> LOCATION: (34)..(34)
<223> OTHER INFORMATION: Xaa is 2-aminocyclopentane carboxylic acid

<400> SEQUENCE: 54

Xaa Val Ser Glu Xaa Gln Xaa Leu His Asp Lys Gly Lys Xaa Ile Gln
1               5                   10                  15

Asp Xaa Arg Arg Arg Glx Phe Leu His Glx Leu Ile Ala Xaa Ile His
            20                  25                  30

Thr Xaa

<210> SEQ ID NO 55
<211> LENGTH: 28
<212> TYPE: PRT
<213> ORGANISM: Artificial Sequence
<220> FEATURE:
<223> OTHER INFORMATION: Artificial PTH polypeptide.

<400> SEQUENCE: 55

Leu Met His Asn Leu Gly Lys His Leu Asn Ser Met Glu Arg Val Glu
1               5                   10                  15

Trp Leu Arg Lys Lys Leu Gln Asp Val His Asn Phe
            20                  25

<210> SEQ ID NO 56
<211> LENGTH: 28
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (1)..(1)
<223> OTHER INFORMATION: Xaa is Beta-3 Phe
<220> FEATURE:
<221> NAME/KEY: MISC_FEATURE
<222> LOCATION: (10)..(10)
<223> OTHER INFORMATION: Xaa is Beta-3 Ser

<400> SEQUENCE: 56

Xaa Met His Asn Leu Gly Lys His Leu Xaa Ser Met Glu Arg Val Glu
1               5                   10                  15

Trp Leu Arg Lys Lys Leu Gln Asp Val His Asn Phe
            20                  25

<210> SEQ ID NO 57
<211> LENGTH: 28
<212> TYPE: PRT
<213> ORGANISM: Artificial Sequence
<220> FEATURE:
<223> OTHER INFORMATION: Artificial PTH polypeptide.
<220> FEATURE:
```

```
<221> NAME/KEY: MISC_FEATURE
<222> LOCATION: (1)..(1)
<223> OTHER INFORMATION: Xaa is Beta-3 Phe
<220> FEATURE:
<221> NAME/KEY: MISC_FEATURE
<222> LOCATION: (10)..(10)
<223> OTHER INFORMATION: Xaa is Beta-3 Ser

<400> SEQUENCE: 57

Xaa Met His Asn Leu Trp Lys His Leu Xaa Ser Met Glu Arg Val Glu
1               5                   10                  15

Trp Leu Arg Lys Lys Leu Gln Asp Val His Asn Phe
            20                  25

<210> SEQ ID NO 58
<211> LENGTH: 28
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (1)..(1)
<223> OTHER INFORMATION: Xaa is Beta-3 Phe
<220> FEATURE:
<221> NAME/KEY: MISC_FEATURE
<222> LOCATION: (8)..(8)
<223> OTHER INFORMATION: Xaa is Beta-3 Trp
<220> FEATURE:
<221> NAME/KEY: MISC_FEATURE
<222> LOCATION: (10)..(10)
<223> OTHER INFORMATION: Xaa is Beta-3 Ser
<220> FEATURE:
<221> NAME/KEY: MISC_FEATURE
<222> LOCATION: (12)..(12)
<223> OTHER INFORMATION: Xaa is Beta-3 Met
<220> FEATURE:
<221> NAME/KEY: MISC_FEATURE
<222> LOCATION: (16)..(16)
<223> OTHER INFORMATION: Xaa is Beta-3 Glu
<220> FEATURE:
<221> NAME/KEY: MISC_FEATURE
<222> LOCATION: (20)..(20)
<223> OTHER INFORMATION: Xaa is Beta-3 Lys
<220> FEATURE:
<221> NAME/KEY: MISC_FEATURE
<222> LOCATION: (24)..(24)
<223> OTHER INFORMATION: Xaa is Beta-3 Asp
<220> FEATURE:
<221> NAME/KEY: MISC_FEATURE
<222> LOCATION: (28)..(28)
<223> OTHER INFORMATION: Xaa is Beta-3 Phe

<400> SEQUENCE: 58

Xaa Met His Asn Leu Trp Lys Xaa Leu Xaa Ser Xaa Glu Arg Val Xaa
1               5                   10                  15

Trp Leu Arg Xaa Lys Leu Gln Xaa Val His Asn Xaa
            20                  25

<210> SEQ ID NO 59
<211> LENGTH: 28
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (1)..(1)
<223> OTHER INFORMATION: Xaa is 2-aminocyclopentane carboxylic acid
<220> FEATURE:
<221> NAME/KEY: MISC_FEATURE
<222> LOCATION: (8)..(8)
<223> OTHER INFORMATION: Xaa is Beta-3 Trp
```

```
<220> FEATURE:
<221> NAME/KEY: MISC_FEATURE
<222> LOCATION: (10)..(10)
<223> OTHER INFORMATION: Xaa is Beta-3 Ser
<220> FEATURE:
<221> NAME/KEY: MISC_FEATURE
<222> LOCATION: (12)..(12)
<223> OTHER INFORMATION: Xaa is Beta-3 Met
<220> FEATURE:
<221> NAME/KEY: MISC_FEATURE
<222> LOCATION: (16)..(16)
<223> OTHER INFORMATION: Xaa is Beta-3 Glu
<220> FEATURE:
<221> NAME/KEY: MISC_FEATURE
<222> LOCATION: (20)..(20)
<223> OTHER INFORMATION: Xaa is Beta-3 Lys
<220> FEATURE:
<221> NAME/KEY: MISC_FEATURE
<222> LOCATION: (24)..(24)
<223> OTHER INFORMATION: Xaa is Beta-3 Asp
<220> FEATURE:
<221> NAME/KEY: MISC_FEATURE
<222> LOCATION: (28)..(28)
<223> OTHER INFORMATION: Xaa is Beta-3 Phe

<400> SEQUENCE: 59

Xaa Met His Asn Leu Trp Lys Xaa Leu Xaa Ser Xaa Glu Arg Val Xaa
1               5                   10                  15

Trp Leu Arg Xaa Lys Leu Gln Xaa Val His Asn Xaa
            20                  25

<210> SEQ ID NO 60
<211> LENGTH: 28
<212> TYPE: PRT
<213> ORGANISM: Artificial Sequence
<220> FEATURE:
<223> OTHER INFORMATION: Artificial PTH polypeptide.
<220> FEATURE:
<221> NAME/KEY: MISC_FEATURE
<222> LOCATION: (1)..(1)
<223> OTHER INFORMATION: Xaa is 2-aminocyclopentane carboxylic acid
<220> FEATURE:
<221> NAME/KEY: MISC_FEATURE
<222> LOCATION: (8)..(8)
<223> OTHER INFORMATION: Xaa is 2-aminocyclopentane carboxylic acid
<220> FEATURE:
<221> NAME/KEY: MISC_FEATURE
<222> LOCATION: (10)..(10)
<223> OTHER INFORMATION: Xaa is Beta-3 Ser
<220> FEATURE:
<221> NAME/KEY: MISC_FEATURE
<222> LOCATION: (12)..(12)
<223> OTHER INFORMATION: Xaa is 2-aminocyclopentane carboxylic acid
<220> FEATURE:
<221> NAME/KEY: MISC_FEATURE
<222> LOCATION: (24)..(24)
<223> OTHER INFORMATION: Xaa is 2-aminocyclopentane carboxylic acid
<220> FEATURE:
<221> NAME/KEY: MISC_FEATURE
<222> LOCATION: (28)..(28)
<223> OTHER INFORMATION: Xaa is 2-aminocyclopentane carboxylic acid

<400> SEQUENCE: 60

Xaa Met His Asn Leu Trp Lys Xaa Leu Xaa Ser Xaa Glu Arg Val Glx
1               5                   10                  15

Trp Leu Arg Glx Lys Leu Gln Xaa Val His Asn Xaa
            20                  25
```